US010391094B2

(12) United States Patent
Jayan et al.

(10) Patent No.: US 10,391,094 B2
(45) Date of Patent: Aug. 27, 2019

(54) COMPOSITIONS AND METHODS FOR TREATING MYELOFIBROSIS

(71) Applicant: Impact Biomedicines, Inc., San Diego, CA (US)

(72) Inventors: Arvind Jayan, La Jolla, CA (US); Janice Cacace, Miami, FL (US)

(73) Assignee: Impact Biomedicines, Inc., Summit, NJ (US)

( * ) Notice: Subject to any disclaimer, the term of this patent is extended or adjusted under 35 U.S.C. 154(b) by 204 days.

(21) Appl. No.: 13/888,096

(22) Filed: May 6, 2013

(65) Prior Publication Data

US 2013/0243853 A1 Sep. 19, 2013

Related U.S. Application Data

(63) Continuation of application No. PCT/US2011/059643, filed on Nov. 7, 2011.

(60) Provisional application No. 61/410,924, filed on Nov. 7, 2010.

(51) Int. Cl.
*A61K 31/506* (2006.01)
*A61K 9/48* (2006.01)

(52) U.S. Cl.
CPC ............. *A61K 31/506* (2013.01); *A61K 9/48* (2013.01); *A61K 9/4866* (2013.01)

(58) Field of Classification Search
CPC ....... A61K 31/506; A61K 9/48; A61K 9/4866
USPC ......................................................... 424/452
See application file for complete search history.

(56) References Cited

U.S. PATENT DOCUMENTS

| | | |
|---|---|---|
| 2,001,051 A | 5/1935 | Bruno |
| 2,002,165 A | 5/1935 | Winslow |
| 2,003,060 A | 5/1935 | Thomas |
| 2,003,065 A | 5/1935 | Boyce |
| 2,003,149 A | 5/1935 | Johnson |
| 2,003,166 A | 5/1935 | Zancan |
| 2,003,187 A | 5/1935 | Good |
| 2,003,199 A | 5/1935 | Johnson et al. |
| 2,004,092 A | 6/1935 | Chaney |
| 2,004,102 A | 6/1935 | Dickey |
| 2,004,138 A | 6/1935 | Story et al. |
| 2,667,486 A | 1/1954 | Cain |
| 4,160,833 A | 7/1979 | Diel |
| 4,309,211 A | 1/1982 | Serban et al. |
| 5,214,059 A | 5/1993 | Tegeler et al. |
| 5,231,097 A | 7/1993 | Klausener et al. |
| 5,332,745 A | 7/1994 | Carter et al. |
| 5,527,763 A | 6/1996 | Miyazaki et al. |
| 5,530,000 A | 6/1996 | Sanfilippo et al. |
| 5,597,826 A | 1/1997 | Howard et al. |
| 5,597,901 A | 1/1997 | Stern |
| 5,665,724 A | 9/1997 | Sanfilippo et al. |
| 5,776,502 A | 7/1998 | Foulkes et al. |
| 5,830,880 A | 11/1998 | Sedlacek et al. |
| 5,849,738 A | 12/1998 | Lee et al. |
| 5,935,383 A | 8/1999 | Sun et al. |
| 5,958,935 A | 9/1999 | Davis et al. |
| 5,965,761 A | 10/1999 | Buchecker et al. |
| 5,972,580 A | 10/1999 | Fukui et al. |
| 6,048,675 A | 4/2000 | Hirano et al. |
| 6,070,126 A | 5/2000 | Kokolus et al. |
| 6,093,838 A | 7/2000 | Vasudevan et al. |
| 6,121,434 A | 9/2000 | Peyman et al. |
| 6,127,382 A | 10/2000 | Beard et al. |
| 6,136,779 A | 10/2000 | Foulkes et al. |
| 6,136,971 A | 10/2000 | Harrington et al. |
| 6,153,752 A | 11/2000 | Bauer et al. |
| 6,194,191 B1 | 2/2001 | Zhang et al. |
| 6,197,779 B1 | 3/2001 | Andries et al. |
| 6,204,260 B1 | 3/2001 | Bruns, Jr. et al. |
| 6,235,746 B1 | 5/2001 | Davis et al. |
| 6,277,502 B1 | 8/2001 | Buchecker et al. |
| 6,288,082 B1 | 9/2001 | Wissner et al. |
| 6,297,258 B1 | 10/2001 | Wissner et al. |
| 6,326,487 B1 | 12/2001 | Peyman et al. |
| 6,348,312 B1 | 2/2002 | Peyman et al. |
| 6,378,526 B1 | 4/2002 | Bowman et al. |
| 6,432,963 B1 | 8/2002 | Hisamichi et al. |
| 6,471,968 B1 | 10/2002 | Baker, Jr. et al. |
| 6,489,328 B2 | 12/2002 | Snow et al. |
| 6,506,769 B2 | 1/2003 | Snow et al. |
| 6,605,615 B2 | 8/2003 | Medina et al. |
| 6,613,773 B2 | 9/2003 | Clough et al. |

(Continued)

FOREIGN PATENT DOCUMENTS

| | | |
|---|---|---|
| AU | 38554/93 A | 11/1993 |
| CA | 2375982 A1 | 2/2001 |

(Continued)

OTHER PUBLICATIONS

Carbuccia, N. et al. (Nov. 2009, e-pub. Jul. 16, 2009). "Mutations of ASXL1 Gene in Myeloproliferative Neoplasms," *Leukemia* 23(11):2183-2186.
Cervantes, F. (Oct. 2007). "Myelofibrosis: Biology and Treatment Options," *Eur. J. Haematol. Suppl.* 79(Suppl. 68):13-17.
Cervantes, F et al. (Mar. 26, 2009, e-pub. Nov. 6, 2008). "New Prognostic Scoring System For Primary Myelofibrosis Based on a Study of the International Working Group for Myelofibrosis Research and Treatment," *Blood* 113(13):2895-2901.
Delhommeau, F. et al. (May 28, 2009). "Mutations in TET2 in Myeloid Cancers," *N. Engl. J. Med.* 360(22):2289-2301.
Ernst, T et al. (Aug. 2010, e-pub. Jul. 4, 2010). "Inactivating Mutations of the Histone Methyltransferase Gene EZH2 in Myeloid Disorders," *Nat. Genet.* 42(8):722-726.

(Continued)

*Primary Examiner* — Mina Haghighatian
*Assistant Examiner* — Mei Ping Chui
(74) *Attorney, Agent, or Firm* — Choate, Hall & Stewart LLP; Kristen C. Buteau; Michael A. Shinall

(57) ABSTRACT

Provided herein are compositions and methods for treating myelofibrosis in a subject. The methods comprise administering to the subject an effective amount of compound which is which is N-tert-butyl-3-[(5-methyl-2-{[4-(2-pyrrolidin-1-ylethoxy)phenyl]amino}pyrimidin-4-yl)amino]benzenesulfonamide or a pharmaceutical salt thereof or a hydrate thereof.

26 Claims, 25 Drawing Sheets

(56) References Cited

U.S. PATENT DOCUMENTS

| | | |
|---|---|---|
| 6,635,626 B1 | 10/2003 | Barrish et al. |
| 6,649,608 B2 | 11/2003 | Pease et al. |
| 6,685,938 B1 | 2/2004 | Cheresh et al. |
| 6,689,778 B2 | 2/2004 | Bemis et al. |
| 6,777,412 B2 | 8/2004 | Clough et al. |
| 6,794,378 B2 | 9/2004 | Iino et al. |
| 6,838,464 B2 | 1/2005 | Pease et al. |
| 7,067,522 B2 | 6/2006 | Pease et al. |
| 7,087,597 B1 | 8/2006 | Miwa et al. |
| 7,208,493 B2 | 4/2007 | Wrasidlo et al. |
| 7,208,614 B2 | 4/2007 | Meudt |
| 7,282,504 B2 | 10/2007 | Armistead et al. |
| 7,452,911 B2 | 11/2008 | Stenkamp et al. |
| 7,528,143 B2 | 5/2009 | Noronha et al. |
| 7,652,051 B2 | 1/2010 | Wrasidlo et al. |
| 7,691,858 B2 | 4/2010 | Doukas et al. |
| 7,825,246 B2 | 11/2010 | Noronha et al. |
| 8,133,900 B2 | 3/2012 | Hood et al. |
| 8,138,199 B2 | 3/2012 | Noronha et al. |
| 8,604,042 B2 | 12/2013 | Noronha et al. |
| 2001/0051620 A1 | 12/2001 | Berger et al. |
| 2002/0052386 A1 | 5/2002 | Armistead et al. |
| 2002/0165244 A1 | 11/2002 | Zhou et al. |
| 2003/0060626 A1 | 3/2003 | Clough et al. |
| 2003/0065180 A1 | 4/2003 | Tsou et al. |
| 2003/0096816 A1 | 5/2003 | Cao et al. |
| 2003/0134838 A1 | 7/2003 | Bornemann et al. |
| 2003/0149061 A1 | 8/2003 | Nishihara et al. |
| 2003/0149064 A1 | 8/2003 | Pease et al. |
| 2003/0166932 A1 | 9/2003 | Beard et al. |
| 2003/0199511 A1 | 10/2003 | Li et al. |
| 2004/0029902 A1 | 2/2004 | Singh et al. |
| 2004/0092746 A1 | 5/2004 | Clough et al. |
| 2004/0102630 A1 | 5/2004 | Brumby et al. |
| 2004/0106615 A1 | 6/2004 | Cochran et al. |
| 2004/0138257 A1 | 7/2004 | Bouchard et al. |
| 2005/0001333 A1 | 1/2005 | Wehle et al. |
| 2005/0234049 A1 | 10/2005 | Singh et al. |
| 2005/0234083 A1 | 10/2005 | Chamberlain et al. |
| 2005/0239852 A1 | 10/2005 | Ciufolini et al. |
| 2005/0245524 A1 | 11/2005 | Noronha et al. |
| 2005/0282814 A1 | 12/2005 | Wrasidlo et al. |
| 2006/0079526 A1 | 4/2006 | Wrasidlo et al. |
| 2006/0100227 A1 | 5/2006 | Baenteli et al. |
| 2006/0131762 A1 | 6/2006 | Meudt et al. |
| 2006/0131835 A1 | 6/2006 | Simpson |
| 2006/0247250 A1 | 11/2006 | Cao et al. |
| 2006/0292203 A1 | 12/2006 | Dellamary et al. |
| 2006/0293311 A1 | 12/2006 | Li et al. |
| 2007/0027120 A1 | 2/2007 | Whitehouse et al. |
| 2007/0032493 A1 | 2/2007 | Foley et al. |
| 2007/0060603 A1 | 3/2007 | Singh et al. |
| 2007/0072682 A1 | 3/2007 | Crawford et al. |
| 2007/0149508 A1 | 6/2007 | Noronha et al. |
| 2007/0161645 A1 | 7/2007 | Noronha et al. |
| 2007/0203162 A1 | 8/2007 | Li et al. |
| 2007/0208019 A1 | 9/2007 | Wrasidlo et al. |
| 2007/0259876 A1 | 11/2007 | Doukas et al. |
| 2007/0264330 A1* | 11/2007 | Ragnar-Tolf et al. ........ 424/464 |
| 2007/0299095 A1 | 12/2007 | Singh et al. |
| 2008/0021013 A1 | 1/2008 | Dobrzanski et al. |
| 2008/0027070 A1 | 1/2008 | Noronha et al. |
| 2008/0039622 A1 | 2/2008 | Singh et al. |
| 2009/0088410 A1 | 4/2009 | Zeldis |
| 2009/0197869 A1 | 8/2009 | Arvanitis et al. |
| 2009/0286789 A1* | 11/2009 | Hood et al. ................ 514/235.8 |
| 2010/0016218 A1 | 1/2010 | Lichter et al. |
| 2010/0022522 A1 | 1/2010 | Rodgers et al. |
| 2010/0278811 A1 | 11/2010 | Wrasidlo et al. |
| 2010/0278921 A1 | 11/2010 | Fisher et al. |
| 2010/0330030 A1 | 12/2010 | Wrasidlo et al. |
| 2011/0269721 A1 | 11/2011 | Hood |
| 2012/0190806 A1 | 7/2012 | Jakel et al. |
| 2013/0252988 A1 | 9/2013 | Jayan et al. |

FOREIGN PATENT DOCUMENTS

| | | |
|---|---|---|
| DE | 3205638 A1 | 8/1983 |
| DE | 10024622 A1 | 11/2001 |
| EP | 444769 A1 | 9/1991 |
| EP | 1 054 004 A1 | 11/2000 |
| EP | 1170353 A2 | 1/2002 |
| EP | 1562938 A1 | 8/2005 |
| JP | H02-064553 A | 3/1990 |
| JP | H03-127790 A | 5/1991 |
| JP | H03-240066 A | 10/1991 |
| JP | H07-041461 A | 2/1995 |
| JP | H07-082183 A | 3/1995 |
| JP | H09-274290 A | 10/1997 |
| JP | H10-153838 A | 6/1998 |
| JP | H10-207019 A | 8/1998 |
| JP | H10-213820 A | 8/1998 |
| JP | H10-260512 A | 9/1998 |
| JP | H10-310583 A | 11/1998 |
| JP | 2001/89412 | 4/2001 |
| JP | 2001247411 A | 9/2001 |
| JP | 2002221770 A | 8/2002 |
| JP | 2005527529 A | 9/2005 |
| WO | WO-91/04031 A1 | 4/1991 |
| WO | WO-9118887 A1 | 12/1991 |
| WO | WO-9201675 A2 | 2/1992 |
| WO | WO-9415622 A1 | 7/1994 |
| WO | WO-9709315 A1 | 3/1997 |
| WO | WO-9724122 A1 | 7/1997 |
| WO | WO-9824974 A1 | 6/1998 |
| WO | WO-9828282 A2 | 7/1998 |
| WO | WO-9841512 A1 | 9/1998 |
| WO | WO-9909016 A1 | 2/1999 |
| WO | WO-9924404 A1 | 5/1999 |
| WO | WO-99/31073 A1 | 6/1999 |
| WO | WO-9932454 A1 | 7/1999 |
| WO | WO-9941253 A1 | 8/1999 |
| WO | WO-99/50250 A1 | 10/1999 |
| WO | WO-001874 A1 | 1/2000 |
| WO | WO-0018740 A1 | 4/2000 |
| WO | WO-0018761 A1 | 4/2000 |
| WO | WO-0039101 A1 | 7/2000 |
| WO | WO-0039108 A1 | 7/2000 |
| WO | WO-00/046203 A2 | 8/2000 |
| WO | WO-2000/62778 A1 | 10/2000 |
| WO | WO-00/71536 A1 | 11/2000 |
| WO | WO-0066583 A1 | 11/2000 |
| WO | WO-0076438 A2 | 12/2000 |
| WO | WO-0107027 A2 | 2/2001 |
| WO | WO-0107401 A1 | 2/2001 |
| WO | WO-0112227 A1 | 2/2001 |
| WO | WO-117995 A1 | 3/2001 |
| WO | WO-0121597 A1 | 3/2001 |
| WO | WO-0127105 A1 | 4/2001 |
| WO | WO-0132628 A1 | 5/2001 |
| WO | WO-0144194 A2 | 6/2001 |
| WO | WO-0147892 A1 | 7/2001 |
| WO | WO-0155116 A2 | 8/2001 |
| WO | WO-0162233 A2 | 8/2001 |
| WO | WO-01/064655 A1 | 9/2001 |
| WO | WO-0164646 A2 | 9/2001 |
| WO | WO-0164656 A1 | 9/2001 |
| WO | WO-0164674 A1 | 9/2001 |
| WO | WO-0168186 A2 | 9/2001 |
| WO | WO-0170668 A2 | 9/2001 |
| WO | WO-0172758 A1 | 10/2001 |
| WO | WO-0176582 A1 | 10/2001 |
| WO | WO-0222608 A1 | 3/2002 |
| WO | WO-2002/30358 A2 | 4/2002 |
| WO | WO-0236570 A1 | 5/2002 |
| WO | WO-0242272 A2 | 5/2002 |
| WO | WO-0244166 A2 | 6/2002 |
| WO | WO-02053101 A2 | 7/2002 |
| WO | WO-02053160 A1 | 7/2002 |
| WO | WO-02064096 A2 | 8/2002 |
| WO | WO-02068409 A1 | 9/2002 |
| WO | WO-02076438 A2 | 10/2002 |
| WO | WO-02083667 A2 | 10/2002 |
| WO | WO-02090347 A1 | 11/2002 |

(56) References Cited

FOREIGN PATENT DOCUMENTS

| WO | WO-02092087 A1 | 11/2002 | | |
|---|---|---|---|---|
| WO | WO-02094766 A1 | 11/2002 | | |
| WO | WO-02096905 A1 | 12/2002 | | |
| WO | WO-02097116 A2 | 12/2002 | | |
| WO | WO-03004018 A1 | 1/2003 | | |
| WO | WO-03/016306 A1 | 2/2003 | | |
| WO | WO-03024448 A2 | 3/2003 | | |
| WO | WO-03/030909 A1 | 4/2003 | | |
| WO | WO-03032994 A2 | 4/2003 | | |
| WO | WO-03033503 A2 | 4/2003 | | |
| WO | WO-03033504 A1 | 4/2003 | | |
| WO | WO-03033505 A1 | 4/2003 | | |
| WO | WO-03/037891 A1 | 5/2003 | | |
| WO | WO-03037869 A1 | 5/2003 | | |
| WO | WO-03045921 A1 | 6/2003 | | |
| WO | WO-03050090 A1 | 6/2003 | | |
| WO | WO-03051366 A2 | 6/2003 | | |
| WO | WO-03057165 A2 | 7/2003 | | |
| WO | WO-03/063794 A2 | 8/2003 | | |
| WO | WO-03/066601 A1 | 8/2003 | | |
| WO | WO-03066575 A1 | 8/2003 | | |
| WO | WO-03078404 A1 | 9/2003 | | |
| WO | WO-03/099771 A2 | 12/2003 | | |
| WO | WO-04000833 A1 | 12/2003 | | |
| WO | WO-2004005283 A1 | 1/2004 | | |
| WO | WO-2004005418 A2 | 1/2004 | | |
| WO | WO-2004/014382 A1 | 2/2004 | | |
| WO | WO-2004018433 A1 | 3/2004 | | |
| WO | WO-2004024663 A1 | 3/2004 | | |
| WO | WO-2004032709 A2 | 4/2004 | | |
| WO | WO-2004037176 A2 | 5/2004 | | |
| WO | WO-2004037814 A1 | 5/2004 | | |
| WO | WO-2004039780 A1 | 5/2004 | | |
| WO | WO-2004046118 A2 | 6/2004 | | |
| WO | WO-2004052373 A1 | 6/2004 | | |
| WO | WO-2004054186 A1 | 6/2004 | | |
| WO | WO-2004/056786 A2 | 7/2004 | | |
| WO | WO-2004/060305 A2 | 7/2004 | | |
| WO | WO-2004058254 A1 | 7/2004 | | |
| WO | WO-2004058782 A1 | 7/2004 | | |
| WO | WO-2004060376 A1 | 7/2004 | | |
| WO | WO-2004/069812 A1 | 8/2004 | | |
| WO | WO-2004071426 A2 | 8/2004 | | |
| WO | WO-2004/080980 A1 | 9/2004 | | |
| WO | WO-2004074261 A1 | 9/2004 | | |
| WO | WO-2004074262 A1 | 9/2004 | | |
| WO | WO-2004074266 A1 | 9/2004 | | |
| WO | WO 2004/091585 A1 * | 10/2004 | ............... | A61K 9/20 |
| WO | WO-2004097504 A1 | 11/2004 | | |
| WO | WO-2005/016894 A1 | 2/2005 | | |
| WO | WO-2005/026130 A1 | 3/2005 | | |
| WO | WO-2005/026158 A1 | 3/2005 | | |
| WO | WO-2006/074057 A2 | 7/2006 | | |
| WO | WO-2006/101977 A2 | 9/2006 | | |
| WO | WO-2006/128129 A2 | 11/2006 | | |
| WO | WO-2006/133426 A2 | 12/2006 | | |
| WO | WO-2006131835 A2 | 12/2006 | | |
| WO | WO-2006137658 A1 | 12/2006 | | |
| WO | WO-2007/000778 A2 | 1/2007 | | |
| WO | WO-2007008541 A2 | 1/2007 | | |
| WO | WO-2007022380 A2 | 2/2007 | | |
| WO | WO-2007/053452 A1 | 5/2007 | | |
| WO | WO-2007053776 A1 | 5/2007 | | |
| WO | WO-2007058627 A1 | 5/2007 | | |
| WO | WO-2007058628 A1 | 5/2007 | | |
| WO | WO 2007089768 A2 * | 8/2007 | | |
| WO | WO-2007/115305 A2 | 10/2007 | | |
| WO | WO-2008/009458 A1 | 1/2008 | | |
| WO | WO-2008/057233 A2 | 7/2008 | | |
| WO | WO-2008157208 A2 | 12/2008 | | |
| WO | WO-2009/046416 A1 | 4/2009 | | |
| WO | WO-2009/073575 A2 | 6/2009 | | |
| WO | WO-2009/073575 A2 | 2/2010 | | |
| WO | WO-2010/017122 A2 | 2/2010 | | |
| WO | WO-2010/017122 A3 | 2/2010 | | |
| WO | WO-2010068182 A1 | 6/2010 | | |
| WO | WO-2011025685 A1 | 3/2011 | | |
| WO | WO-2012/060847 A1 | 5/2012 | | |
| WO | WO-2012/061833 A1 | 5/2012 | | |
| WO | WO-2013/013195 A1 | 1/2013 | | |
| WO | WO-2013/059548 A1 | 4/2013 | | |

OTHER PUBLICATIONS

Flockhart et al. (2009). Located at http://medicine.iupui.edu/clinpharm/ddis/clinical-table/.

Grand, F. H. et al. (Jun. 11, 2009; e-pub. Apr. 22, 2009). "Frequent CBL Mutations Associated With 11q Acquired Uniparental Disomy In Myeloproliferative Neoplasms," Blood 113(24):6182-6192.

Green, A. et al. (Jan. 28, 2010). "Somatic Mutations of IDH1 and IDH2 in the Leukemic Transformation of Myeloproliferative Neoplasms," N. Engl. J. Med. 362(4):369-370.

Hussein, K. et al. (Jan. 21, 2010; e-pub. Nov. 9, 2009). "International Prognostic Scoring System-Independent Cytogenetic Risk Categorization In Primary Myelofibrosis," Blood 115(3):496-499.

Jäger, R. et al. (Jul. 2010; e-pub. May 27, 2010). "Deletions of the Transcription Factor Ikaros in Myeloproliferative Neoplasms," Leukemia 24(7):1290-1298.

James, C. et al. (Apr. 28, 2005). "A Unique Clonal JAK2 Mutation Leading to Constitutive Signalling Causes Polycythaemia Vera," Nature 434(7037):1144-1148.

Kantarjian, H. M. et al. (Nov. 15, 2007; e-pub. Aug. 22, 2007). "Nilotinib (formerly AMN 107), A Highly Selective BCR-ABL Tyrosine Kinase Inhibitor, Is Effective in Patients With Philadelphia Chromosome-Positive Chronic Myelogenous Leukemia in Chronic Phase Following Imatinib Resistance And Intolerance," Blood 110(10):3540-3546.

Kittur, J. et al. (Jun. 1, 2007). "Clinical Correlates of JAK2V617F Allele Burden in Essential Thrombocythemia," Cancer 109(11):2279-2284.

McLorman, D. et al. (May 2006). "JAK2 V617F: A Single Mutation in the Myeloproliferative Group of Disorders," Ulster Med. J. 75(2):112-119.

Oh. S. T. et al. (Aug. 12, 2010). "Novel Mutations in the Inhibitory Adaptor Protein LNK Drive JAK-STAT Signaling in Patients With Myeloproliferative Neoplasms," Blood 116(6):988-992.

Pardanani, A. D. et al. (Nov. 15, 2006; e-pub. Jul. 25, 2006). "MPL515 Mutations in Myeloproliferative And Other Myeloid Disorders: A Study of 1182 Patients," Blood 108(10):3472-3476.

Pardanani, A. et al. (2010; e.pub. Aug. 19, 2010). "LNK Mutation Studies in Blast-Phase Myeloproliferative Neoplasms, And in Chronic-Phase Disease With TET2, IDH, JAK2 or MPL Mutations," Leukemia 24:1713-1718.

Patnaik, M. M. et al. (Feb. 1, 2010). "Age and Platelet Count Are IPSS-Independent Prognostic Factors in Young Patients With Primary Myelofibrosis and Complement IPSS in Predicting Very Long or Very Short Survival," Eur. J. Haematol. 84(2):105-108.

Pikman, Y. et al. (Jul. 18, 2006). "MPLW515L is a Novel Somatic Activating Mutation in Myelofibrosis With Myeloid Metaplasia," PLoS Med. 3(7):1140-1151 (e270).

Scott, L. M. et al. (Feb. 1, 2007). "JAK2 Exon 12 Mutations in Polycythemia Vera and Idiopathic Erythrocytosis," N. Engl. J. Med. 356(5):459-468.

Tefferi, A. (Apr. 27, 2000). "Myelofibrosis With Myeloid Metaplasia," N. Engl. J. Med. 342(17):1255-1265.

Tefferi, A. et al. (Sep. 1, 2006, e-pub. May 4, 2006). "International Working Group (IWG) Consensus Criteria For Treatment Response In Myelofibrosis With Myeloid Metaplasia, For The IWG For Myelofibrosis Research And Treatment (IWG-MRT)," Blood 108(5):1497-1503.

Tefferi, A. et al. (Jan. 2008). "Classification And Diagnosis of Myeloproliferative Neoplasms: The 2008 World Health Organization Criteria And Point-of-Care Diagnostic Algorithms," Leukemia 22(1):14-22.

Tefferi, A. et al. (Jul. 2010). "IDH1 and IDH2 Mutation Studies in 1473 Patients With Chronic-, Fibrotic- or Blast-Phase Essential Thrombocythemia, Polycythemia Vera or Myelofibrosis," Leukemia 24(7):1302-1309.

(56) References Cited

OTHER PUBLICATIONS

Verstovsek, S. (2009). "Therapeutic Potential of JAK2 Inhibitors," *Hematology Am Soc. Hematol. Educ. Program* pp. 636-642.

Wadleigh, M. et al. (Aug. 2010). "Preclinical and Clinical Activity of ATP Mimetic JAK2 Inhibitors," *Clinical Advances in Hematology & Oncology* 8(8):557-563.

Committee Orphan Medicinal Products (Oct. 12, 2010). "Public Summary of Opinion on Orphan Designation (EU/3/10/794) N-tert-butyl-3-[(5-methyl-2-{[4-(2-pyrrolidin-1-ylethoxy)phenyl]amino}pyrimidin-4-yl)amino] benzenesulfonamide dihydrocholoride monohydrate for the Treatment of Primary Myelofibrosis," European Medicines Agency database, under Human Medicines, further under Rare Disease Designations, located at <URL: http://www.ema.europa.eu/docs/en_GB/document_library/Orphan_designation/2010/10/WC500097767.pdf>, last retrieved Feb. 2, 2011, EMA/COMP/477791/2010, 5 pages.

Lasho, T. L. et al. (Sep. 2008, Epub: Mar. 20, 2008). "TG101348, a JAK2-Selective Antagonist, Inhibits Primary Hematopoietic Cells Derived From Myeloproliferative Disorder Patients with JAK2V617F, MPLW515K, or JAK2 Exon 12 Mutations as Well as Mutation Negative Patients," *Leukemia* 22(9):1790-1792. (XP055108559).

Pardanani, A. D. et al. (Dec. 7, 2009). "A Phase I Evaluation of TG101348, a Selective JAK2 Inhibitor, in Myelofibrosis: Clinical Response is Accompanied by Significant Reduction in JAK2V617F Allele Burden," *51$^{st}$ Annual American Society of Hematology (ASH) Annual Meeting and Exposition*, New Orleans, Dec. 5-8, 2009, Posters, online Abstract No. 755, located at http://ash.confex.com/ash/2009/webprogram/Paper20584.html, last visited on Nov. 29, 2010, 2 pages.

International Search Report dated Dec. 12, 2011, for PCT Patent Application No. PCT/US11/059643, filed on Nov. 7, 2011, 4 pages.

Written Opinion dated Dec. 12, 2011, for PCT Patent Application No. PCT/US11/059643, filed on Nov. 7, 2011, 5 pages.

International Search Report dated Mar. 28, 2007, for PCT Patent Application No. PCT/US06/042044, filed on Oct. 26, 2006, 2 pages.

Written Opinion dated Mar. 28, 2007, for PCT Patent Application No. PCT/US06/042044, filed on Oct. 26, 2006, 5 pages.

International Search Report dated Feb. 3, 2009, for PCT Patent Application No. PCT/US2008/078932, filed on Apr. 9, 2009, 3 pages.

Written Opinion dated Feb. 3, 2009, for PCT Patent Application No. PCT/US2008/078932, filed on Apr. 9, 2009, 4 pages.

International Search Report dated Feb. 12, 2010, for PCT Patent Application No. PCT/US2009/052544, filed on Aug. 3, 2009, 4 pages.

Written Opinion dated Feb. 12, 2010, for PCT Patent Application No. PCT/US2009/052544, filed on Aug. 3, 2009, 5 pages.

International Search Report dated Jan. 21, 2011, for PCT Patent Application No. PCT/US2010/56280, filed on Nov. 10, 2010, 4 pages.

Written Opinion dated Jan. 21, 2011, for PCT Patent Application No. PCT/US2010/56280, filed on Nov. 10, 2010, 7 pages.

U.S. Appl. No. 12/846,702, filed Jul. 29, 2010, by Noronha et al.
U.S. Appl. No. 13/357,500, filed Jan. 24, 2012, for Noronha et al.
U.S. Appl. No. 14/072,365, filed Nov. 5, 2013, for Noronha et al.
U.S. Appl. No. 60/353,333, filed Feb. 1, 2002, by Singh et al.

Banker, G. S. et al. Modern Pharmaceutics, 3.sup.rd edition, Revised and Expanded, Marcel Dekker, Inc., New York, New York, p. 596 (1996).

Barosi, G. et al. A Unified Definition of Clinical Resistance and Intolerance to Hydroxycarbamide in Polycythaemia Vera and Primary Myelofibrosis: Results of a European LeukemiaNet (ELN) Consensus Process,British Journal of Haematology 148(6):961-963 (2010).

Barosi, G. et al. A Unified Definition of Clinical Resistance/ Intolerance to Hydroxyurea in Essential Thrombocythemia: Results of a Consensus Process by an International Working Group, Leukemia, 21(2):277-280 (2007).

Bolen et al., "Expression and Interaction of the SRC family of Tyrosine Protein Kinases in T Lymphocytes", Adv. Cancer Res., vol. 57., 103-149, PMID 1950702, 1991.

Borisy, A. A. et al. Systematic Discovery of Multicomponent Therapeutics, Proc. Natl. Acad. Sci. USA100(13):7977-7982 (2003).

Cao, J. et al. (Mar. 2007). "MEDI 119—Design, Syntheses and SAR of Low nM Inhibitors Targeting JAK2," 233.sup.rd ACS National Meeting, Chicago, IL, Mar. 25-29, 2007, located at http://oasys2.confex.com/acs/233nm/techprogram/P1064195.htm, lastvisited Oct. 27, 2010, 1 page.

Chawla, G. et al. (Jan.-Mar. 2004). "Challenges in Polymorphism of Pharmaceuticals", CRIPS 5(1):12-15. [Current Research & Information on Pharmaceutical Science].

Chen, M.L. et al., Impact of osmotically active excipients on bioavailability and bioequivalence of BCS class III drugs, The AAPS Journal, 15(4): 1043-1050 (2013).

ClinicalTrials.Gov, A Dose-Escalation Study of the Safety and Tolerability of Orally Administered TG101348 in Patients With Myelofibrosis, TargeGen, ClinicalTrials.gov Identifier: NCT00631462, 7 pages (last updated Oct. 22, 2009). URL: http://clinicaltrials.gov/ct2/show/study/NCT00631462 [Retrieved Jan. 10, 2011].

ClinicalTrials.Gov, A Long-Term Study of the Effects of Orally Administered TG101348 in Patients With Myelofibrosis, TargeGen, ClinicalTrials.gov Identifier: NCT00724334, 13 pages (last updated Dec. 9, 2009). URL: http://clinicaltrials.gov/ct2/show/study/NCT00724334 [Retrieved Jan. 10, 2011].

Cotto, M. et al. (Jun. 2010). "Epigenetic Therapy of Lymphoma Using Histone Deacetylase Inhibitors," Clin. Transl. Oncol. 12(6):401-409.

Dörwald, F. Z. (2005). Side Reactions in Organic Synthesis, A Guide to Successful Synthesis Design, Wiley-VCH Verlag GmbH & Co. KGaA, Weinheim, p. IX-X of Preface.

eMedicineHealth, Acute Respiratory Distress Syndrome, 3 pages. URL: http://www.emedicinehealth.com/acute_respiratory_distress_syndrome/page2_em.htm [Retrieved Dec. 10, 2007].

Epstein, J., Hematology—Myeloproliferative Neoplasms, Highlights of the 2009 Meeting of the American Society of Hematology Myeloproliferative Neoplasms, OncoFact, Abstract 755: 7 pages (2010). URL: http://oncofacts.com/archives/highlights-of-the-2009-meeting-of-the-ameri- can-society-of-hematology-myeloproliferative-neoplasms/. [Retrieved Jan. 10, 2011].

FDA.Gov, FDA Application Results for Orphan Drug Product Designations Search, Treatment of Secondary and Primary Myelofibrosis, Sponsored by TargeGen, Inc., 1 page (May 18, 2009). URL: http://www.accessdata.fda.gov/scripts/opdlisting/oopd/OOPD_Results_2.cf . . . [Retrieved Nov. 2, 2010].

Frohlich et al., "Inhibition of Neuronal Nitric Oxide Synthase by 4-Amino Pteridine Derivatives: Structures-Activity Relationship of Antagonists of (6R)-5,6,7,8-Tetrahydrobiopterin Cofactor", J. Med. Chem., vol. 42, 4108-4121, 1999.

Geron, I. et al. (Apr. 2008). "Selective Inhibition of JAK2-Driven Erythroid Differentiation of Polycythemia Vera Progenitors," Cancer Cell 13(4):321-330.

Ghobadi, A. (Feb. 5, 2010). "JAK2 Inhibitors," Oral Presentation presented at Washington University in St Louis, located at <hematology.wust.edu/conferences/presentations/Ghobadi20100205.ppt>—, 34 pages total.

Ghosh, D. et. al. (Sep. 1967). "2,4-Bis(arylamino)-5-Methylpyrimidines as Antimicrobial Agents," J. Med. Chem. 10(5): 974-975.

Granelli-Piperno, A. SRC-Related Proto-Oncogenes and Transcription Factors in Primary Human T Cells: Modulation by Cyclosporine A and FK506, J. Autoimmun. 5(A):145-158 (1992).

Guy, E. et al. Accelerated Proliferation and Limited Differentiation, Mediated through Jak2, Exacerbate Ineffective Erythropoiesis in β-Thalassemia, Blood (ASH Annual Meeting Abstracts), 110(Abstract275): 2 pages (2007). URL: http://abstracts.hematologylibrary.org/cgi/content/abstract/ashmtg;11-0/11/275?maxtoshow=&hits= . . . [Retrieved Nov. 9, 2010].

Hood, J. et al., TG101348, A Potent, Highly Selective JAK2 Inhibitor, Inhibits Colony Formation in Stem Cells From Polycythemia Vera Patients and Prevents JAK2V617F-Mediated Splenomegaly and Death in a Mouse Model, 2007 ASCO Annual Meeting,

(56) References Cited

OTHER PUBLICATIONS

Abstract 7031: 3 pages (2007). URL: http://www.asco.org/ascov2/Meetings/Abstracts?&vmview=abst_detail_view&confID=47 . . . [Retrieved Mar. 14, 2011].

Jacobson, J. R. et al. Simvastatin Attenuates Vascular Leak and Inflammation in Murine Inflammatory Lung Injury, Am. J. Physiol. Lung. Cell. Mol. Physiol. 288(6):L1026-L1032 (2005).

Kobayashi et al., Functional coupling of the src-family protein tyrosine kinases p59fyn and p53/61yn with the interleukin 2 receptor: implications for redundancy and pleiotropism in cytokine signal transduction, Proc. Natl. Acad. Sci. USA, 90:4201-4205 (1993).

Lasho, T. et al. Inhibition of JAK-Stat Signaling by TG101348: A Novel Mechanism for Inhibition of KITD816V-Dependent Growth in Mast Cell Leukemia Cells, Leukemia 24(7):1378-1380 (2010).

Libani, I. V. et al., Decreased Differentiation of Erythroid Cells Exacerbates Ineffective Erythropoiesis in β-Thalassemia, Blood 112(3):875-885 (2008).

Ma, A. C. H. et al. (Dec. 2009, e-pub. Sep. 20, 2009). "A Novel Zebrafish jak2a.sup.V581F Model Shared Features of Human JAK2.sup.V617F Polycythemia Vera," Exp. Hematol. 37(12):1379-1386.

Mak, C.-C. et al., MEDI 118—A novel series of low nM JAK2 selective inhibitors exhibit potent in vitro activities with favorable preclinical properties, The 233rd ACS National Meeting, Chicago, IL, Mar. 25-29, 2007, 1 page. URL: athttp://oasys2.confex.com/acs/233nm/techprogram/P1064196.htm [Retrieved Oct. 27, 2010].

MayoClinic.com, Stroke:Treatment, 4 pages (Jul. 5, 2006). URL: http://www.mayoclinic.com/health/stroke/DS00150/DSECTIOn=7 [Retrieved Dec. 10, 2007].

McPherson, A. et al. (Mar. 2007). "MEDI 120—Development of Novel and Potent Inhibitors of JAK2: Structure Activity Relationship Studies for Optimization of JAK2 Potency while Minimizing JAK3 Activity," 233.sup.rd ACS National Meeting, Chicago, IL, Mar. 25-29, 2007, located at http://oasys2.confex.com/acs/233nm/techprogram/P1064173.htm, last visited Oct. 27, 2010, 1 page.

Medscape, VEGF Manipulation Ameliorates Murine Asthma Symptoms, 1 page (2006). URL: http://www.medscape.com/viewarticle/544205_print [Retrieved Dec. 10, 2007].

Mesa, R. A. et al. (Sep. 2009). "Emerging Drugs for the Therapy of Primary and Post Essential Thrombocythemia, Post Polycythemia Vera Myelofibrosis," Expert Opin. Emerg. Drugs 14(3):471-479.

Mullally, A. et al. (Jun. 15, 2010). "Physiological Jak2V617F Expression Causes a Lethal Myeloproliferative Neoplasm With Differential Effects on Hematopoietic Stem and Progenitor Cells," Cancer Cell 17(6):584-596.

New Mexico Department of Health, Interleukin-2, New Mexico AIDS InfoNet, Fact Sheet No. 622: 1 page (Apr. 30, 2002). URL: http://www.aidsinfonet.org.

Newman, A. W. et al. Solid-State Analysis of the Active Pharmaceutical Ingredient in Drug Products, Drug Discovery Today 8(19):898-905 (2003).

O'Shea et al., "Expression of v-src in a Murine T-cell Hybridoma Results in Constitutive T-cell Receptor Phosphorylation and Interleukin 2 Production", Proc. Natl. Acad. Sci., 88:1741-1745 (1991).

Pardanani, A. D. et al. A Phase I Study of TG101348, An Orally Bioavailable JAK2-Selective Inhibitor, in Patients With Myelofibrosis, 50th ASH Annual Meeting and Exposition, Abstract 97: 2 pages (Dec. 7, 2008). URL: http://ash.confex.com/ash/2008/webprogram/Paper10141.html [Retrieved Nov. 30, 2010].

Pardanani, A. et al. Longer-Term Follow up With TG101348 Therapy in Myelofibrosis Confirms Sustained Improvement in Splenomegaly, Disease-Related Symptoms, and JAK2V617F Allele Burden, 52nd ASH Annual Meeting and Exposition, Abstract 459: 2 pages (Dec. 6, 2010). URL: http://ash.confex.com/ash/2010/webprogram/Paper28895.html. [Retrieved Nov. 29, 2010].

Pardanani, A. et al. Safety and Efficacy of TG101348, A Selective JAK2 Inhibitor, in Myelofibrosis, J. Clin. Oncol. 29(7):789-796 (2011).

Pardanani, A. et al. TG101209, a Small Molecule JAK-2 Selective Kinase Inhibitor Potently Inhibits Myeloproliferative Disorder-Associated JAK2V617F and MPLW515L/K Mutations, Leukemia 21(8):1658-1668 (2007).

Pardanani, A. et al. TG101348, a JAK2-Selective Inhibitor, is Well Tolerated in Patients With Myelofibrosis and Shows Substantial Therapeutic Activity Accompanied by a Reduction in JAK2V617F Allele Burden, 14th Congress of the EHA, Berlin, Germany, Abstract 1088:1 page (Jun. 4-7, 2009). URL: http://www.eventure-online.com/eventure/publicAbstractView.do?id=1027-69&congressId=2432. [Retrieved Nov. 30, 2010].

Quintas-Cardama, A. et al. (Apr. 15, 2010, e-pub. Feb. 3, 2010). "Preclinical Characterization of the Selective JAK1/2 Inhibitor INCB018424: Therapeutic Implications for the Treatment of Myeloproliferative Neoplasms," Blood 115(15):3109-3117.

Ramakrishnan, V. et al. (Sep. 2010). "TG101209, A Novel JAK2 Inhibitor, Has Significant in Vitro Activity in Multiple Myeloma and Displays Preferential Cytotoxicity for CD45+ Myeloma Cells," Am. J. Hematol. 85(9):675-686.

Rivella, S. et al, A Novel Murine Model of Cooley Anemia and its Rescue by Lentiviral Mediated Human .beta.-Globin Gene Transfer, Blood 101(8): 2932-2939 (2003).

Samanta, A. et al. (Mar. 2011, e-pub. Dec. 24, 2010). "Janus Kinase 2 Regulates Bcr-Abl Signaling in Chronic Myeloid Leukemia," Leukemia 25(3):463-472.

Savjani, K.T. et al., Drug solubility: importance and enhancement techniques, ISRN Pharmaceutics, vol. 2012(Article ID 195727): 10 pages (2012).

Sun, Y. et al. (Feb. 15, 2011). "Inhibition of JAK2 Signaling by TG101209 Enhances Radiotherapy in Lung Cancer Models," J. Thorac. Oncol. 6:699-706.

Taghavi-Moghadam et al., A New, General and Regioselective Method for the Synthesis of 2,6-Disubstituted 4-Aminopteridines, Elsevier Science Ltd., Pergamon, 6835-6836 (1997).

Tam, C. S. et al. (Sep. 1, 2008, e-pub. Jun. 19, 2008). "The Natural History and Treatment Outcome of Blast Phase BCR-ABL-Myeloproliferative Neoplasms," Blood 112(5):1628-1637.

Tanaka et al., "novel human tyrosine kinase gene inducible in T cells by interleukin 2", FEBS Lett., vol. 7:324, No. 1, 1-5, PMID 9504851, Jun. 1993.

Torigoe, T. et al. Regulation of SRC-Family Protein Tyrosine Kinases by Interleukins, IL-2, and IL-3, Leukemia 6(Sup. 3):945-975 (1992).

Verstovsek, S. et al. Characterization of JAK2 V617F Allele Burden in Advanced Myelofibrosis (MF) Patients: No Change in V617F:WT JAK2 Ratio in Patients With High Allele Burdens Despite Profound Clinical Improvement Following TreatmentWith the JAK Inhibitor, INCB018424, Blood (Ash Annual Meeting Abstracts), 112(Abstract 2802): 2 pages (2008). URL: http://abstracts.hematologylibrary.org/cgi/content/abstract/112/Nov. 2802?maxtosho . . . [Retrieved Nov. 2, 2010].

Verstovsek, S. et al. Safety and Efficacy of INCB018424, a JAK1 and JAK2 Inhibitor, in Myelofibrosis, N. Eng. J. Med. 363(12):1117-1127 (2010).

Verstovsek, S. Therapeutic Potential of Janus-Activated Kinase-2-Inhibitors for the Management of Myelofibrosis, Clin. Cancer Res. 16(7):1988-1996 (2010).

Vippagunta, S. R. et. al. Crystalline Solids, Adv. Drug Deliv. Rev. us 48(1) 3-26 (2001).

Wadleigh, M. et al. Classification and Diagnosis of Myeloproliferative Neoplasms According to the 2008 World Health Organization Criteria, Int. J. Hematol. 91(2):174-179 (2010).

Weber, T. Molecular Approaches to Study Cellular Roadblocks to Transfection and Transduction (Non-Viral Vectors and AAV-Based Vectors for Gene Therapy, 1-8 (2002). URL: http://www.mssm.edu/genetherapy/weber.htm.

Wernig, G. et al. Efficacy of TG101348, a Selective JAK2 Inhibitor, in Treatment of a Murine Model of JAK2V617F-Induced Polycythemia Vera, Cancer Cell, 13(4):311-320 (2008).

Wikipedia, Acute respiratory distress syndrome, 11 pages. URL: http://en.wikipedia.org/wiki/Acute_respiratory_distress_syndrome [Retrieved Dec. 10, 2007].

(56) References Cited

OTHER PUBLICATIONS

Wikipedia, Leukemia, 10 pages (last modified on Jan. 6, 2011). URL: http://en.wikipedia.org/wiki/Leukemia [Retrieved Jan. 7, 2011].

Wills, B. A. et al. (Sep. 1, 2005). "Comparison of Three Fluid Solutions for Resuscitation in Dengue Shock Syndrome," The New England Journal of Medicine 353(9):877-889.

Wolff, M.E. et. al., Burger's Medicinal Chemistry and Drug Discovery, A Wiley-Interscience Publication, 5th Edition, vol. I: Principles and Practice: 975-982 (1995).

Yamamoto et al., "Role of src-like protooncogenes in lymphocotye proliferation", Princess Takamastu Symp., vol. 22, 293-305 Review, PMID 1668889, 1991.

Zimmermann, J. et al. (Jul. 1996). "Phenylamino-Pyrimidine (PAP) Derivatives: A New Class of Potent and Selective Inhibitors of Protein Kinase C (PKC)," Arch. Der Pharm., Pharmaceutical and Medicinal Chemistry 329(7):371-376.

Harrison, C.N. et al., Janus kinase-2 inhibitor fedratinib in patients with myelofibrosis previously treated with ruxolitinib(JAKARTA-2): a single-arm, open-label, non-randomised, phase 2, multicentre study, Lancet Haematol, 4: e317-324 (2017).

Hirani, J.J. et al., Orally Disintegrating Tablets: A Review, Tropical Journal of Pharmaceutical Research, 8(2): 161-172 (2009).

U.S. Department of Health and Human Services Food and Drug Administration Center for Drug Evaluation and Research (CDER), Guidance for Industry Orally Disintegrating Tablets, 6 pages (Dec. 2008).

Wernig, G. et al., Efficacy of TG101348, a Selective JAK2 Inhibitor, in Treatment of a Murine Model of JAK2V617F-Induced Polycythemia Vera, Cancer Cell, 13: 311-320 (2008).

\* cited by examiner

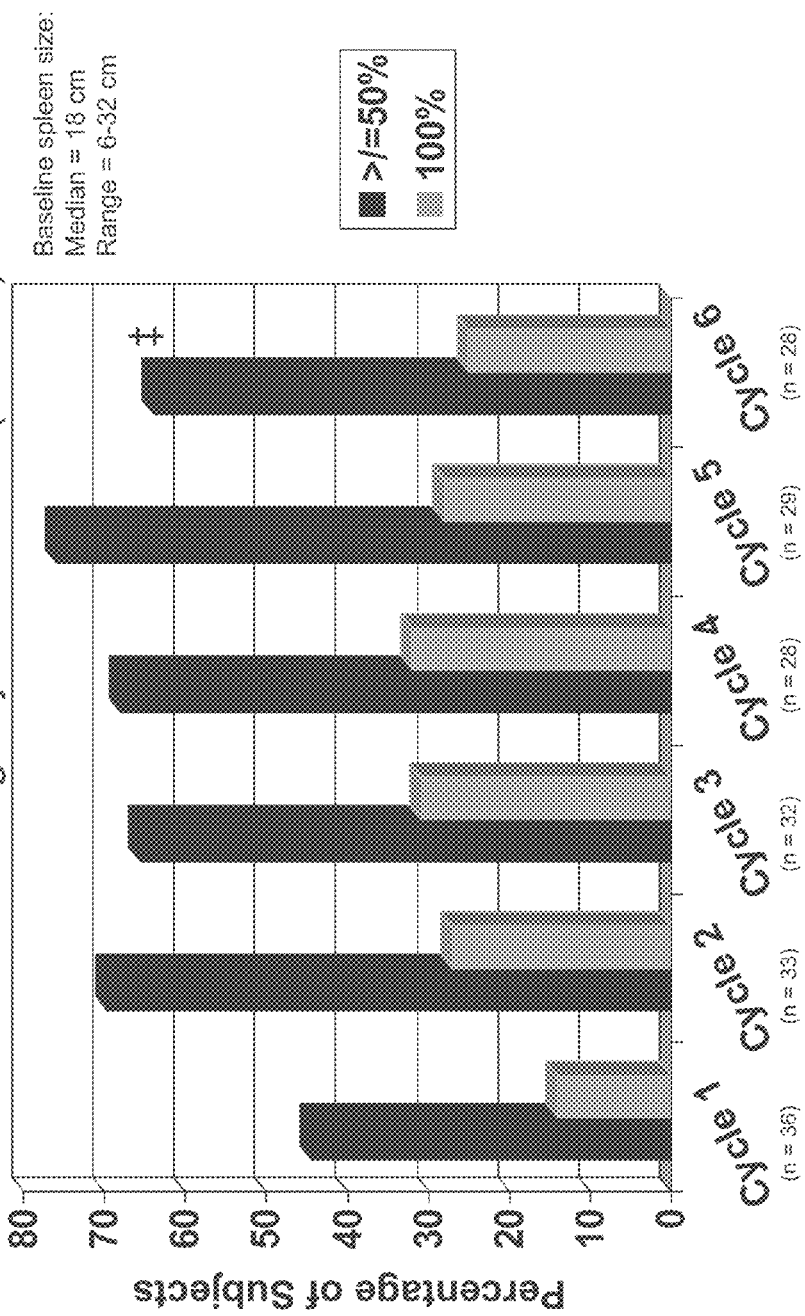

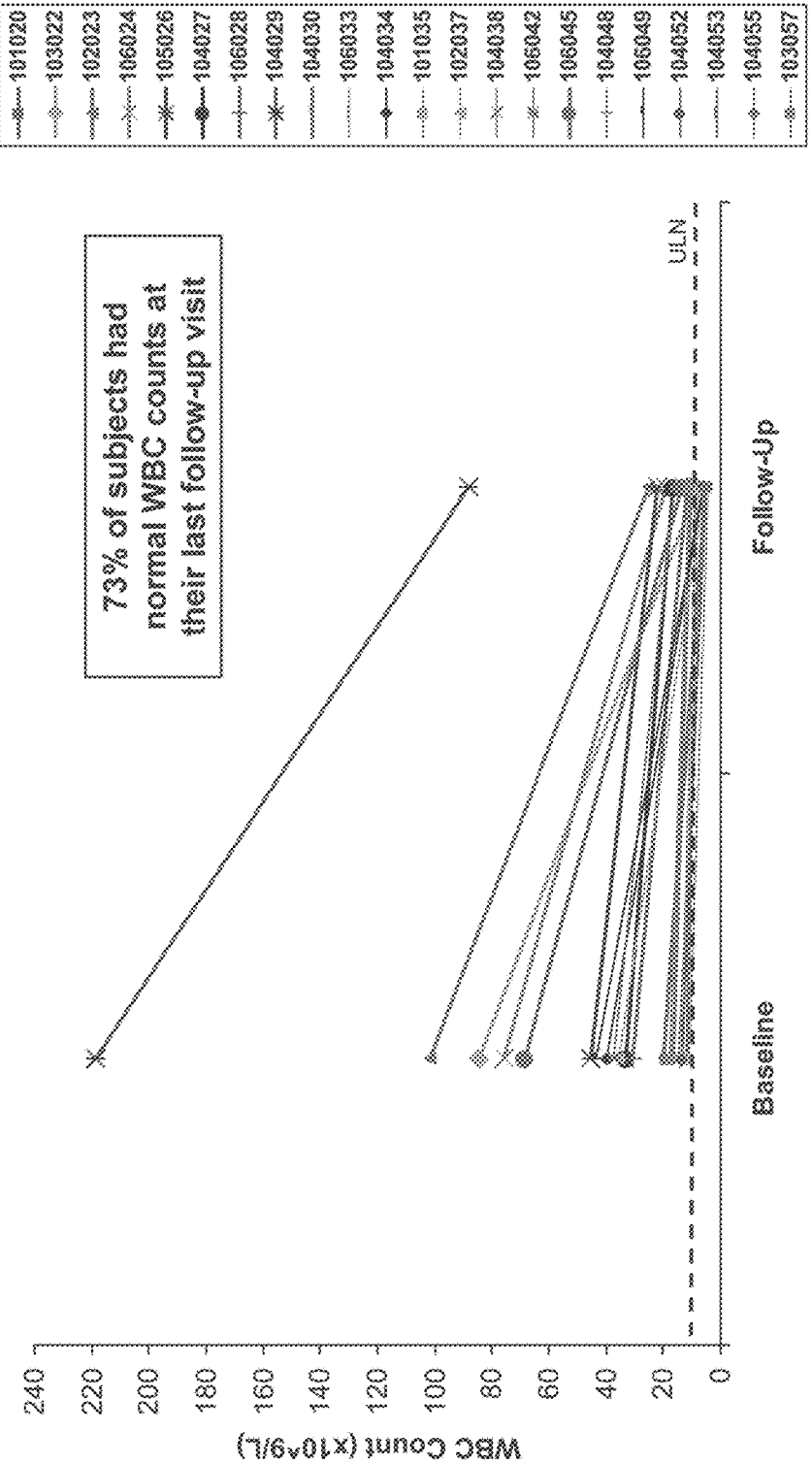

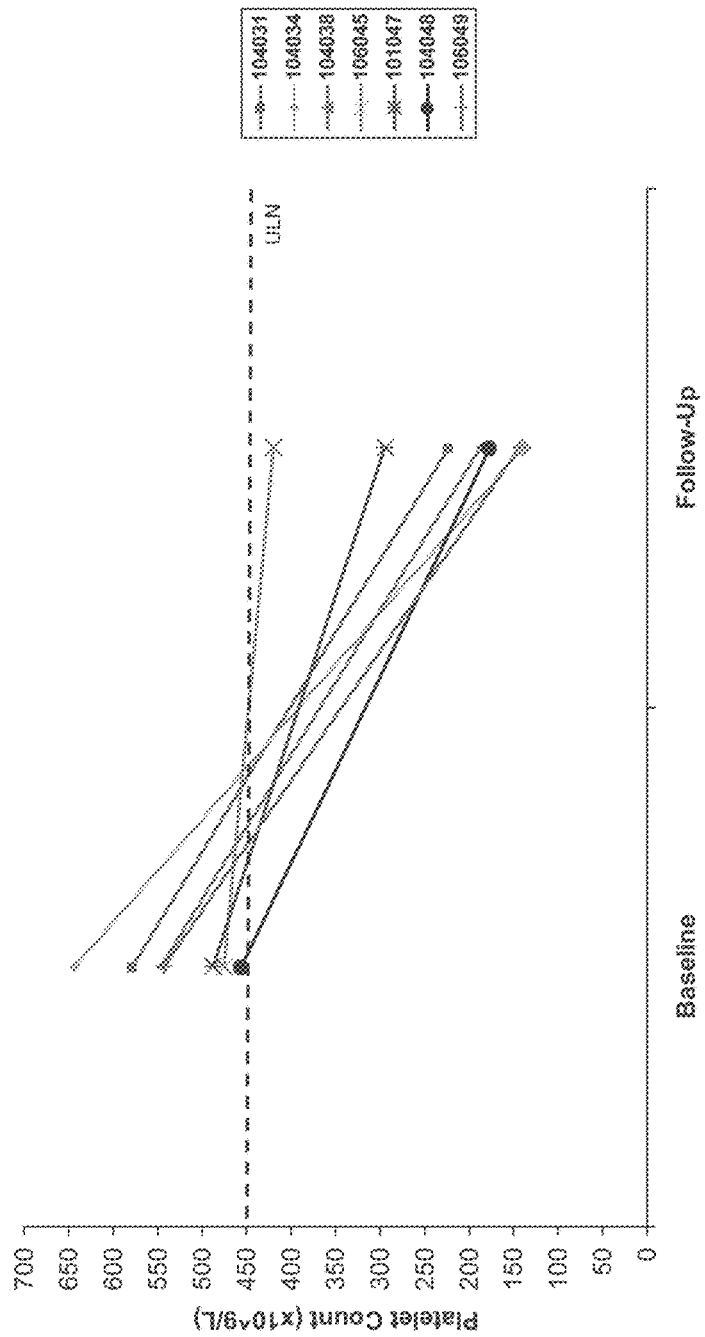

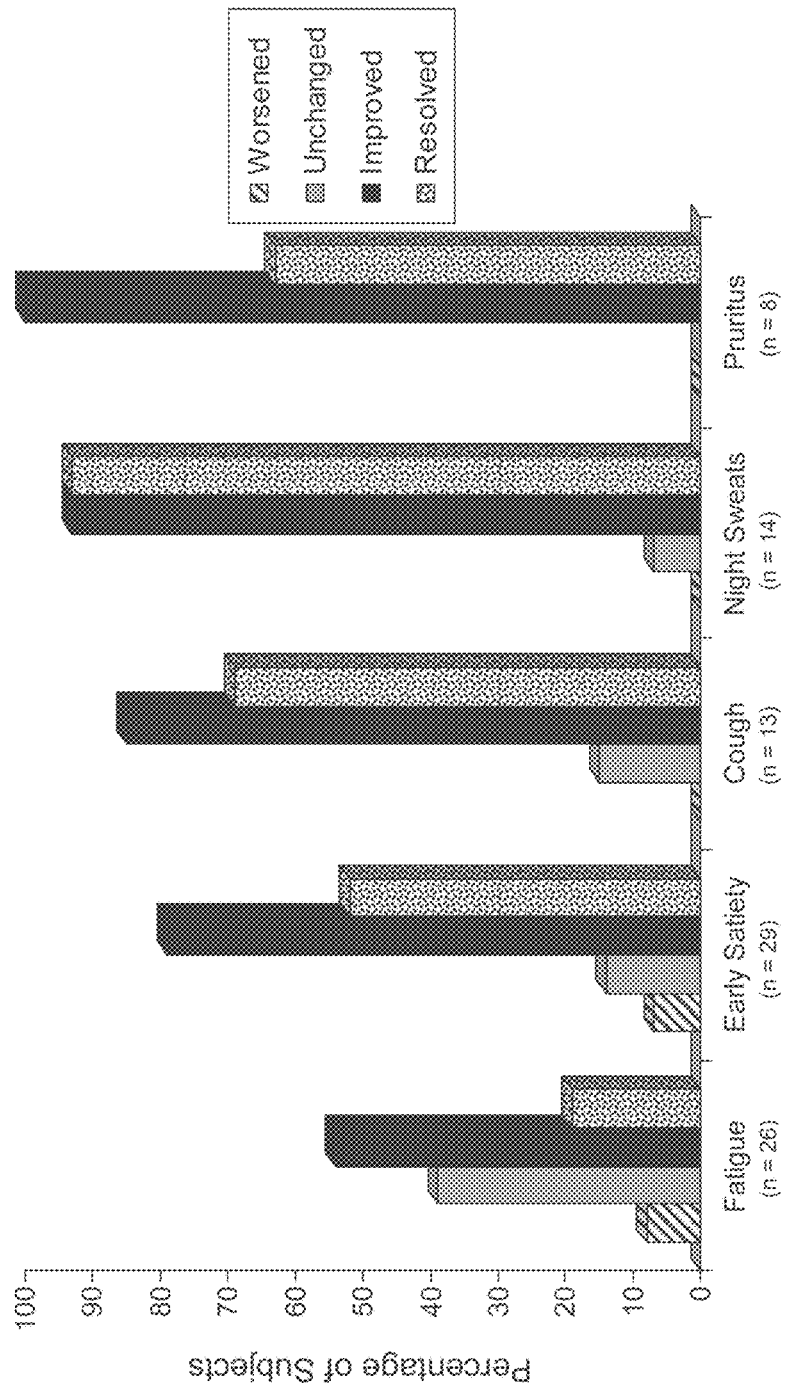

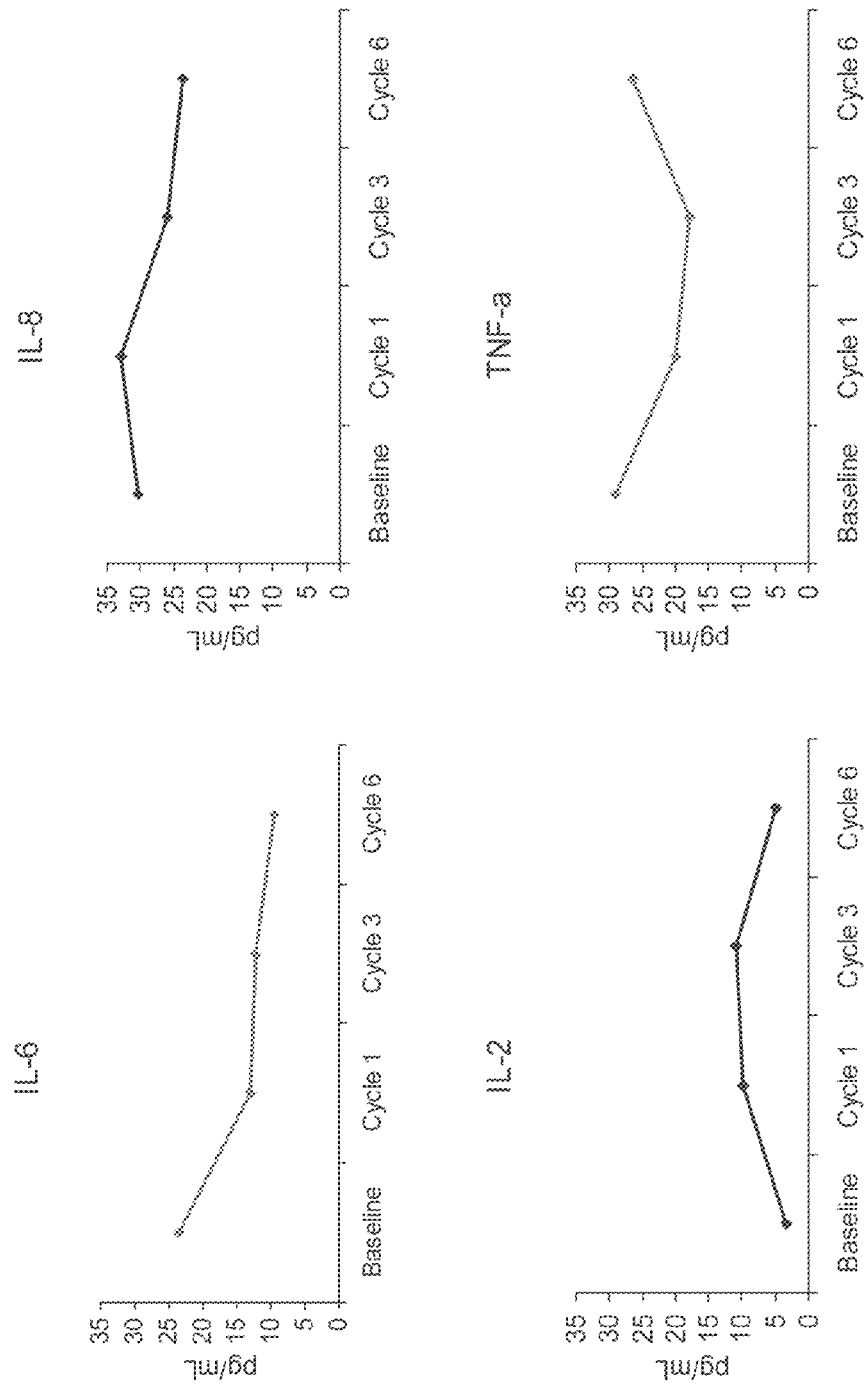

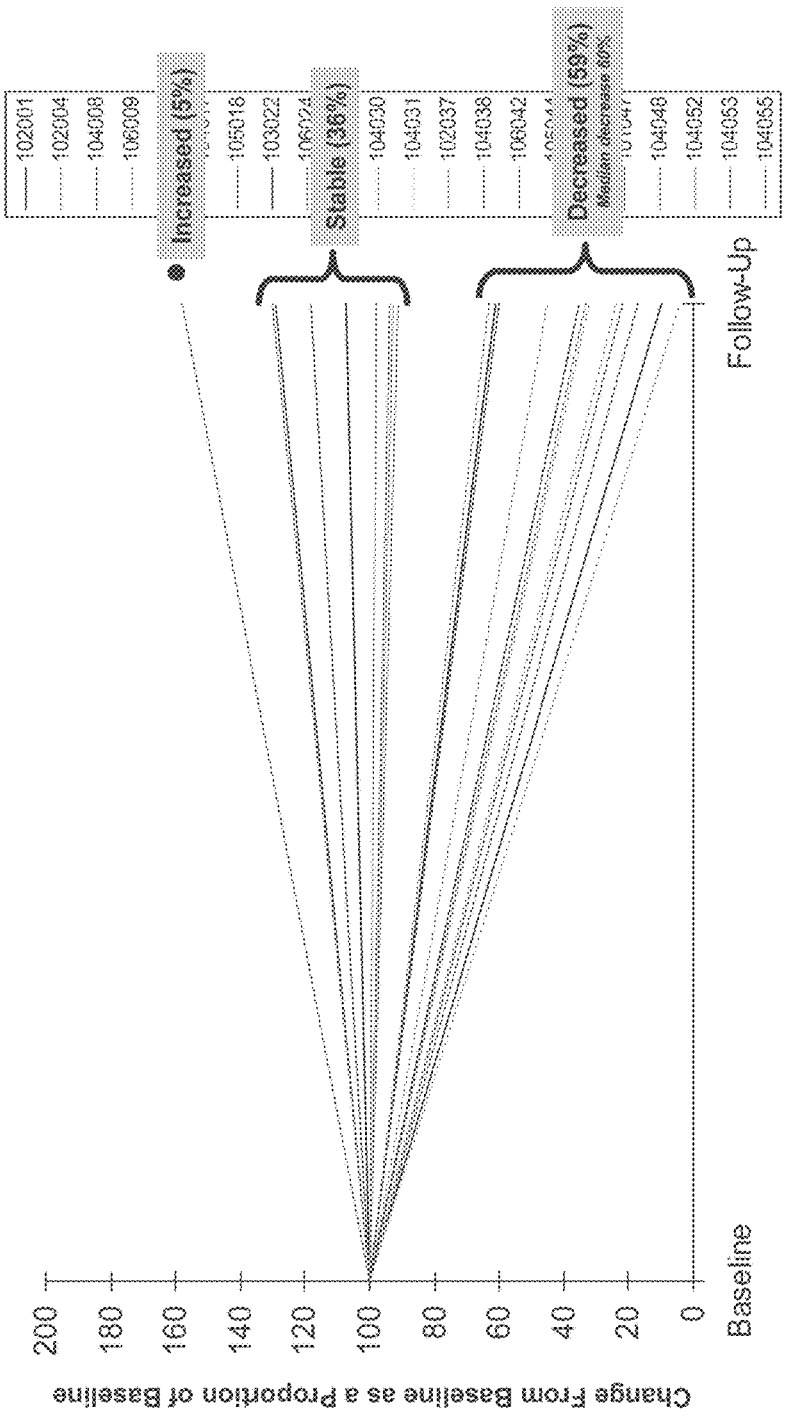
Figure 6 TG101348 Effect on V617F Allele Burden in Subjects With Baseline > 20% (N = 22)*

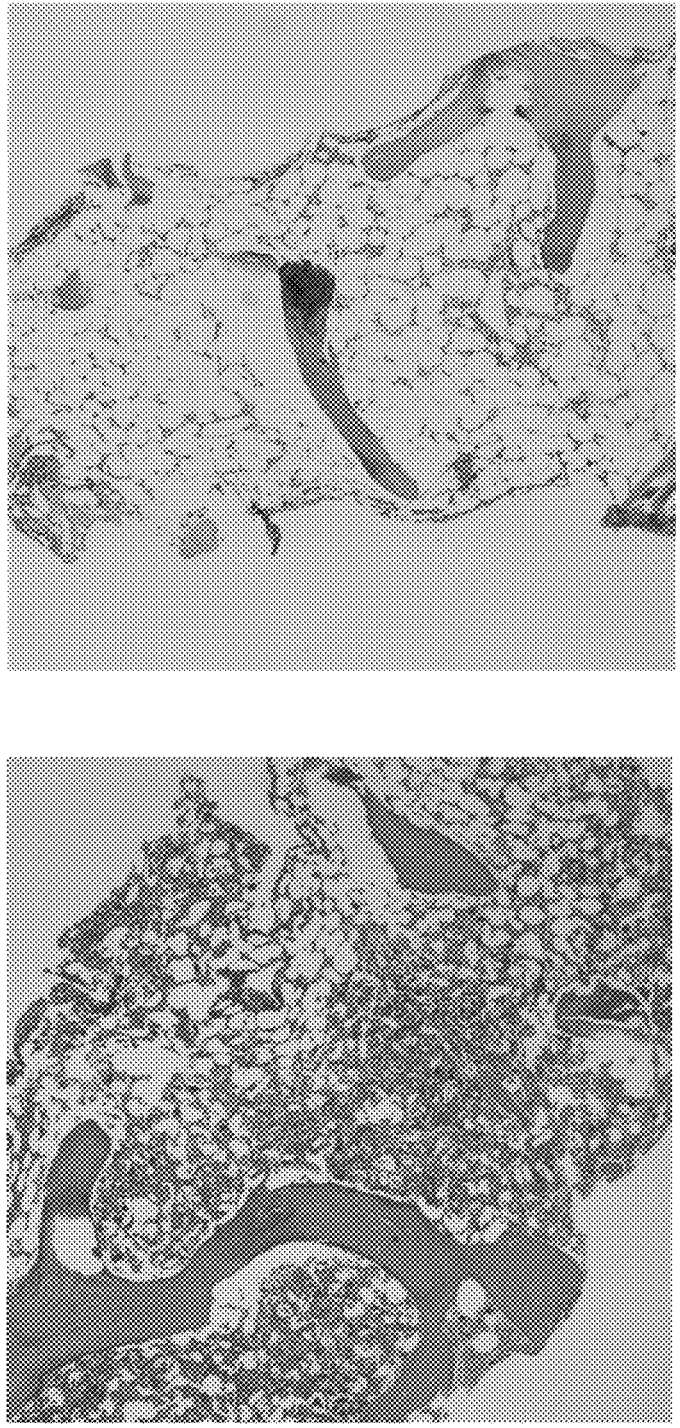
Figure 7 Effect on BM Cellularity
Baseline: 60% cellularity
After 18 cycles: 5-10% cellularity
76-year-old male, V617F negative PMF; starting dose, 30 mg/day; dose at follow-up, 520 mg/day.

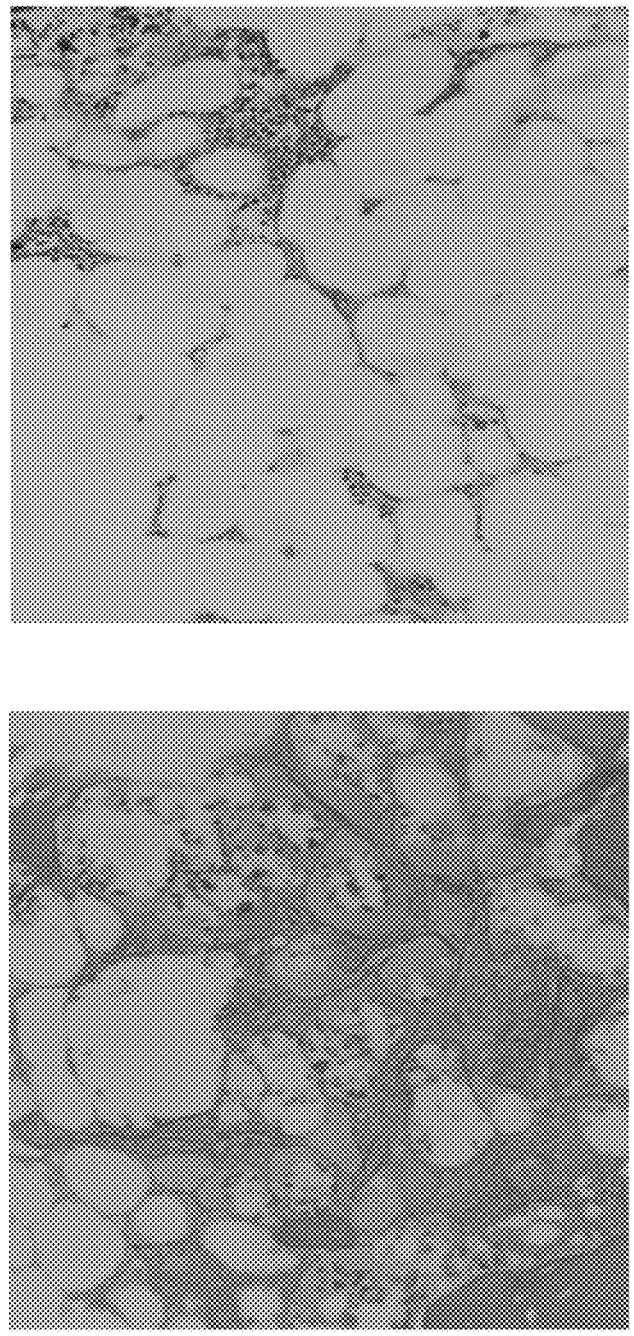
Figure 8 Effect on BM Fibrosis
Baseline: 3+    After 18 cycles: 0
56-year-old male, V617F negative PMF; starting dose, 240 mg/day; dose at follow-up, 440 mg/day.

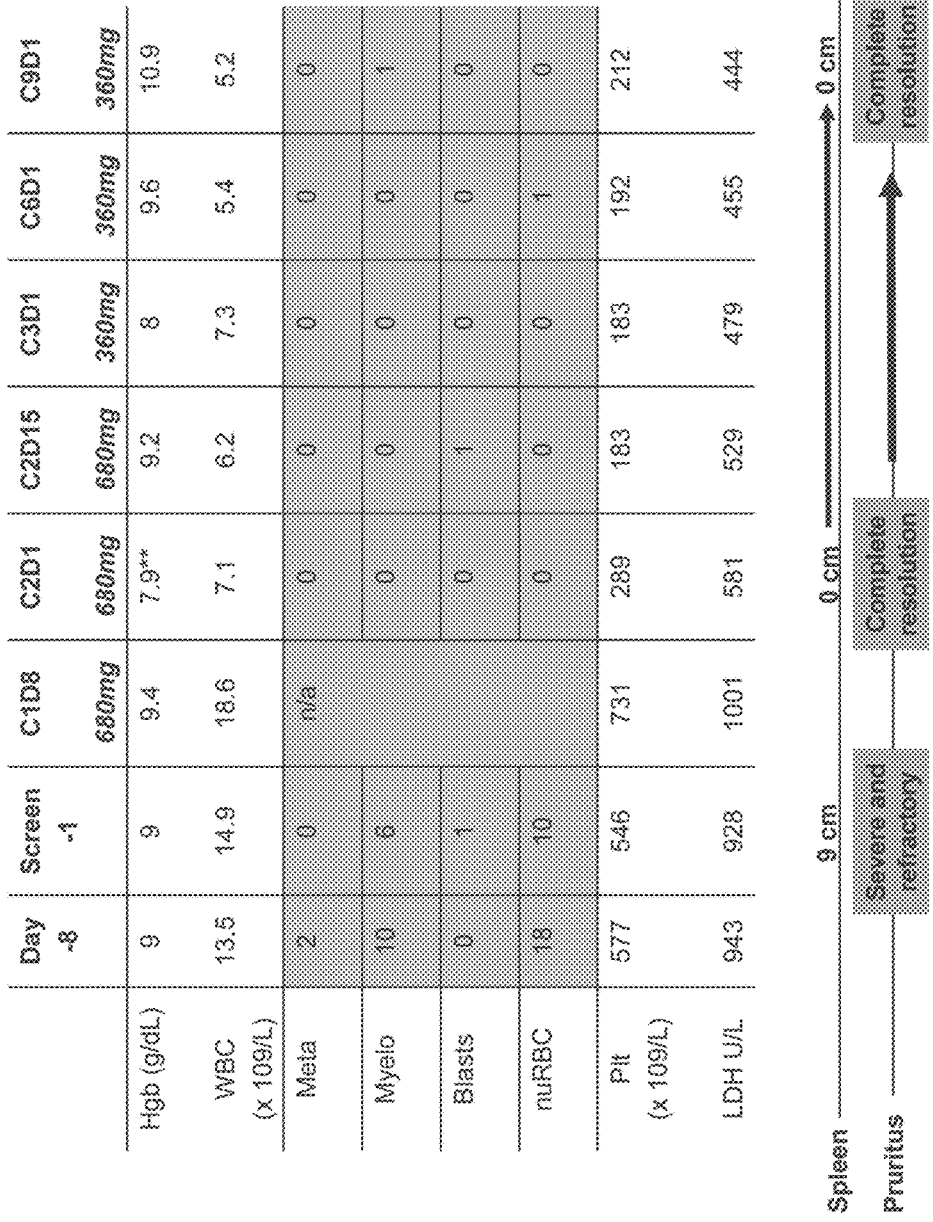
Figure 9 A subject with JAK2V617F-positive PMF started at 680 mg/day (TG101348)

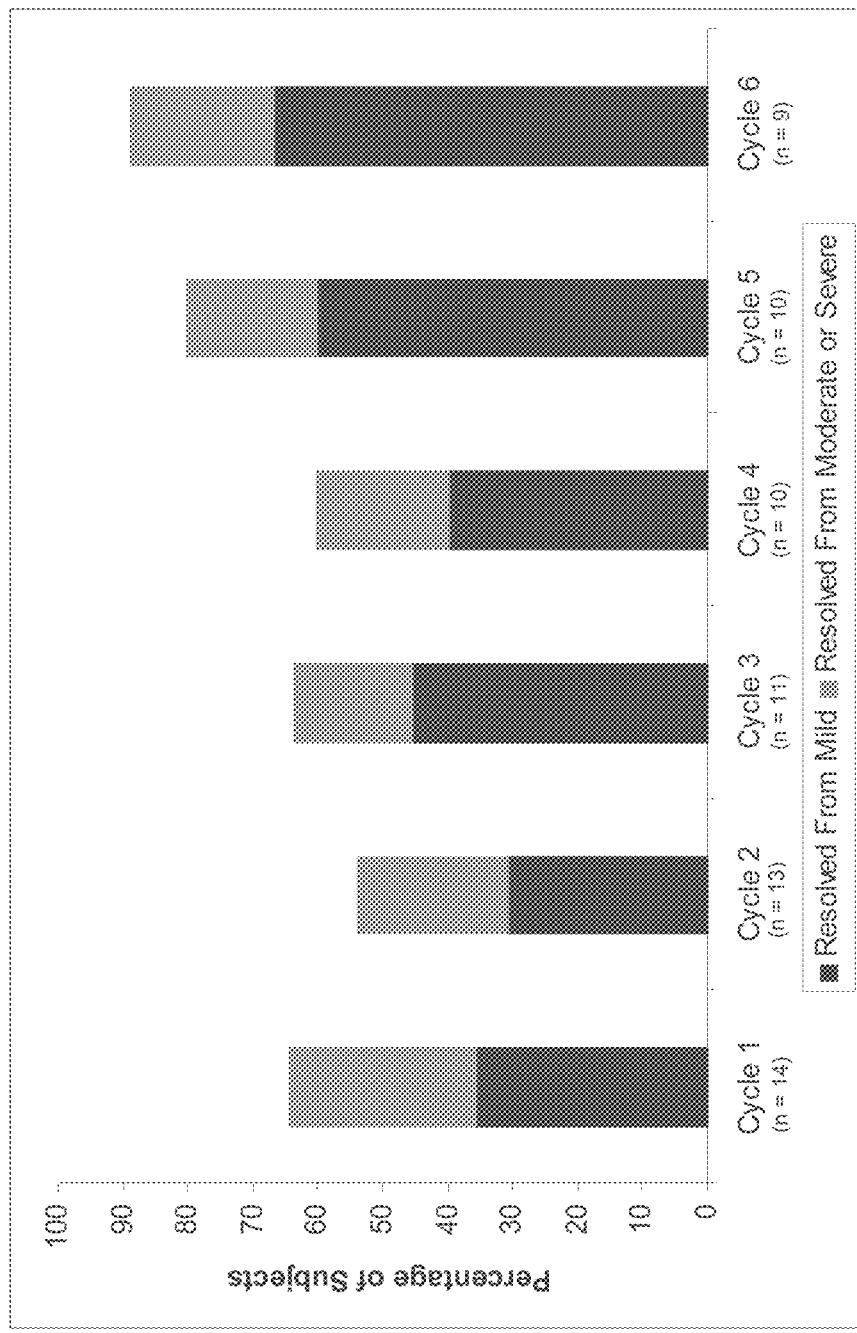

ion application of International Application Number PCT/US2011/059643, filed Nov. 7, 2011, which claims the priority benefit of U.S. provisional application Ser. No. 61/410,924, filed Nov. 7, 2010, the disclosures of which are incorporated herein by reference in their entirety.

TECHNICAL FIELD

Provided herein are compositions and methods for treating myelofibrosis. The compositions and methods provided herein relate to treatment of myelofibrosis with compounds that inhibit JAK2 or a pharmaceutically acceptable salt thereof or a hydrate thereof.

BACKGROUND

Myelofibrosis ("MF") is a rare disease mainly affecting people of older age. MF is a BCR-ABL1-negative myeloproliferative neoplasm ("MPN") that presents de novo (primary) or may be preceded by polycythemia vera ("PV") or essential thrombocythemia ("ET"). Clinical features include progressive anemia, marked splenomegaly, constitutional symptoms (e.g. fatigue, night sweats, bone pain, pruritus, and cough) and weight loss (Tefferi A, N Engl J Med 342:1255-1265, 2000). Median survival ranges from less than 2 years to over 15 years based on currently identified prognostic factors (Cervantes F et al., Blood 113:2895-2901, 2009; Hussein K et al. Blood 115:496-499, 2010; Patnaik M M et al., Eur J Haematol 84:105-108, 2010). Mutations involving JAK2 (James C et al., Nature 434:1144-1148, 2005; Scott L M et al., N Engl J Med 356:459-468, 2007), MPL (Pikman Y et al., PLoS Med 3:e270, 2006), TET2 (Delhommeau F et al., N Engl J Med 360:2289-2301, 2009), ASXLI (Carbuccia N et al., Leukemia 23:2183-2186, 2009), IDH1/IDH2 (Green A et al., N Engl J Med 362:369-370, 2010; Tefferi A et al., Leukemia 24:1302-1309, 2010), CBL (Grand F H et al., Blood 113:6182-6192, 2009), IKZF1 (Jager R et al., Leukemia 24:1290-1298, 2010), LNK (Oh S T et al., Blood 116:988-992, 2010), or EZH2 (Ernst T et al., Nat Genet. 42:722-726) have been described in patients with MPN, including those with MF. Some mutations occur at high frequency in MF (e.g. JAK2 mutations in ~50% patients), and either directly (e.g. JAK2 or MPL mutations) or indirectly (e.g. LNK or CBL mutations) induce JAK-STAT hyperactivation.

The currently available treatments are not effective in reversing the process of MF, be it primary or secondary disease. The only potential for cure of the disease to date is bone marrow transplantation. However, most patients are not suitable bone marrow transplant candidates because of the older median age at diagnosis, in which transplant-related morbidity and mortality tends to be high. Thus management options of MF are currently inadequate to meet the needs of all patients. The main options for active intervention include cyto-reductive therapy, e.g. with hydroxyurea, treatment of anemia with androgens, erythropoietin and splenectomy. These options have not been shown to improve survival and are largely seen as palliative (Cervantes F., Myelofibrosis: Biology and treatment options, European Journal of Haematology, 2007, 79 (suppl. 68) 13-17). Therefore, there is a need to provide additional therapy options for MF patients.

SUMMARY OF THE INVENTION

Provided herein are capsules suitable for oral administration. In some embodiments, the capsule comprises an admixture of (i) a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, (ii) a microcrystalline cellulose, and (iii) sodium stearyl fumarate, wherein the admixture is contained in the capsule.

In some embodiments, the capsule contains about 10 mg to about 680 mg of the compound, wherein the specified weight is the free base moiety weight of the compound. In some embodiments, the capsule contains about 10 mg to about 500 mg of the compound. In some embodiments, the capsule contains about any of 10 mg, 40 mg, 100 mg, 200 mg, 300 mg, 400 mg, 500 mg, or 600 mg of the compound. In some embodiments, the weight ratio of the compound to microcrystalline cellulose in the capsule is between about 1:1.5 to 1:15, wherein the weight for the compound in the weight ratio is the free base moiety weight of the compound. In some embodiments, the weight ratio of the compound to sodium stearyl fumarate in the capsule is between about 5:1 to about 50:1, and wherein the weight for the compound in the weight ratio is the free base moiety weight of the compound. In some embodiments, the microcrystalline cellulose is silicified microcrystalline cellulose. In some embodiments, the silicified microcrystalline cellulose is a combination of 98% microcrystalline cellulose and 2% colloidal silicon dioxide.

Also provided herein are unit dosage forms comprising an admixture of (i) a compound which is N-tert-butyl-3-[(5-methyl-2-{[4-(2-pyrrolidin-1-ylethoxy)phenyl]amino} pyrimidin-4-yl)amino]benzenesulfonamide or a pharmaceutically acceptable salt thereof or a hydrate thereof, (ii) a microcrystalline cellulose, and (iii) sodium stearyl fumarate. In some embodiments, the unit dosage forms are for treatment of myelofibrosis such as treatment of myelofibrosis according to a method described herein.

In some embodiments, the unit dosage form comprises an admixture of (i) about 10 mg to about 680 mg (or about 10 mg to about 500 mg) of a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, wherein the specified weight is the free base moiety weight of the compound, (ii) a microcrystalline cellulose, and (iii) sodium stearyl fumarate. In some embodiments, the unit dosage form is in the form of a capsule, and the admixture is contained in the capsule. In some embodiments, the compound in the admixture is about 10 mg to about 500 mg, wherein the specified weight is the free base moiety weight of the compound. In some embodiments, the admixture comprises (i) about 10 mg (or about any of 40 mg, 100 mg, 200 mg, 300 mg, 400 mg, or 500 mg) of the compound, (ii) a microcrystalline cellulose, and (iii) sodium stearyl fumarate, wherein the specified weight is the free base moiety weight of the compound. In some embodiments, the compound is N-tert-butyl-3-[(5-methyl-2-{[4-(2-pyrrolidin-1-ylethoxy)phenyl]amino}pyrimidin-4-yl)amino]benzenesulfonamide dihydrochloride monohydrate. In some embodiments, the weight ratio of the compound to microcrystalline cellulose in the capsule is between about 1:1.5 to 1:15, wherein the weight for the compound in the weight ratio is the free base moiety weight of the compound. In some embodiments, the weight ratio of the compound to sodium stearyl fumarate in the capsule is between about 5:1 to about 50:1, and wherein the weight for the compound in the weight ratio is the free base moiety weight of the compound. In some embodiments, the microcrystalline cellulose is silicified microcrystalline cellulose. In some embodiments, the silicified microcrystalline cellulose is a combination of 98% microcrystalline cellulose and 2% colloidal silicon dioxide.

In some embodiments, sodium stearyl fumarate is about 1% w/w of capsule fill weight. In some embodiments, the weight ratio of the compound to microcrystalline cellulose such as silicified microcrystalline cellulose is about 40:60 to about 10:90 (e.g., about 40:60 or about 1:1.5, or about 10:90 or about 1:9).

In some embodiments, the compound is N-tert-butyl-3-[(5-methyl-2-{[4-(2-pyrrolidin-1-ylethoxy)phenyl]amino}pyrimidin-4-yl)amino]benzenesulfonamide dihydrochloride monohydrate. In some embodiments, the unit dosage form or capsule contains an admixture of about 12 mg of N-tert-butyl-3-[(5-methyl-2-{[4-(2-pyrrolidin-1-ylethoxy)phenyl]amino}pyrimidin-4-yl)amino]benzenesulfonamide dihydrochloride monohydrate, about 122 mg of silicified microcrystalline cellulose, and about 1 mg of sodium stearyl fumarate. In some embodiments, the unit dosage form or capsule contains an admixture of about 47 mg of N-tert-butyl-3-[(5-methyl-2-{[4-(2-pyrrolidin-1-ylethoxy)phenyl]amino}pyrimidin-4-yl)amino]benzenesulfonamide dihydrochloride monohydrate, about 448 mg of silicified microcrystalline cellulose, and about 5 mg of sodium stearyl fumarate. In some embodiments, the unit dosage form or capsule contains an admixture of about 117 mg of N-tert-butyl-3-[(5-methyl-2-{([4-(2-pyrrolidin-1-ylethoxy)phenyl]amino}pyrimidin-4-yl)amino]benzenesulfonamide dihydrochloride monohydrate. In some embodiments, the unit dosage form or capsule contains an admixture of about 235 mg of N-tert-butyl-3-[(5-methyl-2-{[4-(2-pyrrolidin-1-ylethoxy)phenyl]amino}pyrimidin-4-yl)amino]benzenesulfonamide dihydrochloride monohydrate, about 357 mg of silicified microcrystalline cellulose, and about 6.00 mg of sodium stearyl fumarate. In some embodiments, the capsule is a hard gelatin capsule.

Also provided herein are methods of preparing a capsule drug product comprising a) blending a lubricant with a compound that is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof to generate granules and b) mixing the granules of a) with an excipient. In some embodiments, the lubricant is sodium stearyl fumarate. In some embodiments, the excipient is microcrystalline cellulose such as silicified microcrystalline cellulose. In some embodiments, sodium stearyl fumarate is about 1% w/w of capsule fill weight. In some embodiments, the weight ratio of the compound to silicified microcrystalline cellulose is about 1:1.5 to about 1:9. In some embodiments, the weight ratio of the compound to silicified microcrystalline cellulose is about 1:1.5. In some embodiments, the weight ratio of the compound to silicified microcrystalline cellulose is about 1:9. In some embodiments, the capsule is a hard gelatin capsule.

Also provided herein are methods of treating myelofibrosis in a subject, comprising orally administering a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, and wherein the compound is in an admixture of (i) the compound, (ii) an excipient (e.g., a microcrystalline cellulose), and (iii) a lubricant (e.g., sodium stearyl fumarate). Any of the unit dosage forms or capsules described herein may be used. In some embodiments, there is provided a method of treating myelofibrosis in a subject comprising orally administering a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, and wherein the compound is in a capsule containing an admixture of (i) the compound, (ii) a microcrystalline cellulose (e.g., silicified microcrystalline cellulose), and (iii) sodium stearyl fumarate.

Also provided herein are methods of treating myelofibrosis in a subject, comprising administering to the subject an effective amount of a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, wherein the subject is negative for the valine 617 to phenylalanine mutation of human Janus Kinase 2 (JAK2) or negative for the mutation corresponding to the valine 617 to phenylalanine mutation of human JAK2.

Also provided herein are methods of treating myelofibrosis in a subject, comprising administering to the subject an effective amount of a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, wherein the subject has previously received another myelofibrosis therapy. In some embodiments, the previous therapy is a treatment with a JAK2 inhibitor which is not N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof. In some embodiments, the previous therapy comprises administration of INCB018424 (ruxolitinib). In some embodiments, the subject is unresponsive to the previous therapy. In some embodiments, the previous therapy is a treatment with N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof. In some embodiments, the previous therapy has been discontinued upon indication of elevated levels of amylase, lipase, aspartate aminotransferase ("AST"), alanine aminotransferase ("ALT"), and/or creatinine. In some embodiments, the previous therapy has been discontinued upon indication of a hematologic condition selected from the group consisting of anemia, thrombocytopenia, and neutropenia.

Also provided herein are methods of ameliorating bone marrow cellularity or bone marrow fibrosis associated with myelofibrosis in a subject, comprising administering to the subject an effective amount of a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof.

Also provided herein are methods of improving pruritus associated with myelofibrosis in a subject, comprising administering to the subject an effective amount of a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof.

Also provided herein are methods of monitoring treatment of myelofibrosis in a subject, comprising (a) administering to a subject an effective amount of a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof; (b) monitoring a non-hematologic parameter selected from the group consisting of amylase level, lipase level, aspartate aminotransferase (AST) level, alanine aminotransferase (ALT) level, and creatinine level in the subject; and (c) determining if the subject should continue or discontinue with the treatment. Also provided herein are methods of monitoring treatment of myelofibrosis to a subject, comprising administering to the subject an effective amount of a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, and discontinuing the treatment upon indication of elevated levels of one or more enzymes or molecules selected from the group consisting of amylase, lipase, aspartate aminotransferase (AST), alanine aminotransferase (ALT), and creatinine in the serum of the subject without prior dose reduction. In some embodiments, the one or more of the elevated levels are Grade 4 events.

Also provided herein are methods of monitoring a treatment of myelofibrosis to a subject, comprising (a) administering to the subject an effective amount of a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof; (b) monitoring a hematologic parameter selected from the group consisting of anemia, thrombocytopenia, and neutropenia in the serum of the subject; and (c) determining if the subject should continue or discontinue with the treatment. Also provided herein are methods of monitoring treatment of myelofibrosis to a subject, comprising administering to the subject an effective amount of a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, and discontinuing the treatment upon indication of one or more hematologic conditions selected from the group consisting of anemia, thrombocytopenia, and neutropenia without prior dose reduction. In some embodiments, the one or more hematologic conditions are grade 4 events.

In some embodiments of the methods of monitoring treatment provided herein, the methods further comprise administering to the subject an effective amount of a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof after the subject has been discontinued with the treatment for at least 2 weeks. In some embodiments, the subject has been discontinued with the treatment for at least 3 weeks. In some embodiments, the subject has been discontinued with the treatment for at least 4 weeks. In some embodiments, the treatment has been discontinued without prior dose reduction.

In some embodiments, the compound is administered to the human subject at a dose of about 240 mg per day to about 680 mg per day, and wherein the specified weight is the free base moiety weight of the compound. In some embodiments, the compound is administered at a dose of about 300 mg per day to about 500 mg per day (e.g., about 300 mg per day to about 400 mg per day, or about 400 mg per day to about 500 mg per day), and wherein the specified weight is the free base moiety weight of the compound. In some embodiments, the compound is administered at a dose of about any of 240 mg per day, 250 mg per day, 300 mg per day, 350 mg per day, 400 mg per day, 450 mg per day, 500 mg per day, 550 mg per day, 600 mg per day, 650 mg per day, or 680 mg per day, and wherein the specified weight is the free base moiety weight of the compound. In some embodiments, the compound is administered daily and/or orally. In some embodiments, the compound is administered over a period of at least 1 cycle, at least 2 cycles, at least 3 cycles, at least 4 cycles, at least 5 cycles, or at least 6 cycles (e.g., at least 7 cycles, at least 8 cycles, at least 9 cycles, at least 10 cycles, at least 11 cycles, at least 12 cycles, at least 15 cycles, at least 18 cycles, or at least 24 cycles) of a 28-day treatment cycle. In some embodiments, the compound is in a capsule and administered orally. In some embodiments, the compound is in a unit dosage form. Any of the capsules or unit dosage forms described herein may be administered. In some embodiments of the methods provided herein, the compound is in an admixture of (i) a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, (ii) a microcrystalline cellulose, and (iii) sodium stearyl fumarate. In some embodiments, the weight ratio of the compound to microcrystalline cellulose in the admixture is between about 1:1.5 to 1:15, and wherein the weight for the compound is the free base moiety weight of the compound. In some embodiments, the weight ratio of the compound to sodium stearyl fumarate in the admixture is between about 5:1 to about 50:1, and wherein the weight for the compound is the free base moiety weight of the compound. In some embodiments, the compound is N-tert-butyl-3-[(5-methyl-2-{[4-(2-pyrrolidin-1-ylethoxy)phenyl]amino}pyrimidin-4-yl)amino]benzenesulfonamide dihydrochloride monohydrate. In some embodiments, the microcrystalline cellulose is silicified microcrystalline cellulose. In some embodiments, the subject is a human.

In some embodiments of the compositions and methods provided herein, the subject has primary myelofibrosis. In some embodiments of the compositions and methods provided herein, the subject has post polycythemia vera myelofibrosis. In some embodiments of the compositions and methods provided herein, the subject has post essential thrombocythemia myelofibrosis. In some embodiments, the subject has high risk myelofibrosis. In some embodiments, the subject has intermediate risk myelofibrosis (such as intermediate risk level 2). In some embodiments of the compositions and methods provided herein, the subject is positive for the valine 617 to phenylalanine mutation of human Janus Kinase 2 (JAK2) or positive for the mutation corresponding to the valine 617 to phenylalanine mutation of human JAK2. In some embodiments of the compositions and methods provided herein, the subject is negative for the valine 617 to phenylalanine mutation of human Janus Kinase 2 (JAK2) or negative for the mutation corresponding to the valine 617 to phenylalanine mutation of human JAK2. In some embodiments of the compositions and methods provided herein, the subject has palpable splenomegaly. In some embodiments, the subject with myelofibrosis has spleen of at least 5 cm below costal margin as measured by palpation. In some embodiments of the compositions and methods provided herein, the subject is transfusion dependent. In some embodiments of the compositions and methods provided herein, the subject is not transfusion dependent.

In some embodiments of the methods provided herein, upon administration of the compound to a human subject, the Cmax of the compound is achieved within about 2 to about 4 hours post-dose. In some embodiments, upon administration of the compound to a human subject, the elimination half life of the compound is about 16 to about 34 hours. In some embodiments, the mean AUC of the compound increases more than proportionally with increasing doses ranging from about 30 mg to about 800 mg per day. In some embodiments, the accumulation of the compound is about 1.25 to about 4.0 fold at steady state when the compound is dosed once daily. In some embodiments, the compound is in an admixture of (i) a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, (ii) microcrystalline cellulose, and (iii) sodium stearyl fumarate. In some embodiments, the weight ratio of the compound to microcrystalline cellulose in the admixture is between about 1:1.5 to 1:15, and wherein the weight for the compound is the free base moiety weight of the compound. In some embodiments, the weight ratio of the compound to sodium stearyl fumarate in the admixture is between about 5:1 to about 50:1, and wherein the weight for the compound is the free base moiety weight of the compound. In some embodiments, the compound is N-tert-butyl-3-[(5-methyl-2-{[4-(2-pyrrolidin-1-ylethoxy)phenyl]amino}pyrimidin-4-yl)amino]benzenesulfonamide dihydrochloride monohydrate. In some embodiments, the microcrystalline cellulose is silicified microcrystalline cellulose.

Also provided herein are articles of manufacture or kits comprising (a) any one of the capsules provided herein, and (b) a package insert or a label indicating that the capsule is useful for treating myelofibrosis in a subject. Also provided herein are articles of manufacture or kits comprising (a) any one of the unit dosage forms provided herein, and (b) a package insert or a label indicating that the capsule is useful for treating myelofibrosis in a subject. In some embodiments, there is provided an article of manufacture or kit comprising (a) an admixture of (i) a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, (ii) microcrystalline cellulose, and (iii) sodium stearyl fumarate, and (b) a package insert or a label indicating that the admixture is useful for treating myelofibrosis in a subject.

Also provided herein are articles of manufacture or kits comprising (a) a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutical salt thereof or a hydrate thereof, and (b) a package insert or a label indicating that the compound can be used for treating myelofibrosis in a subject, wherein the subject is negative for the valine 617 to phenylalanine mutation of human Janus Kinase 2 (JAK2) or negative for the mutation corresponding to the valine 617 to phenylalanine mutation of human JAK2.

Also provided herein are articles of manufacture or kits comprising (a) a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutical salt thereof or a hydrate thereof, and (b) a package insert or a label indicating that the compound can be used for treating myelofibrosis in a subject, wherein the subject has previously received another myelofibrosis therapy. In some embodiments, the previous therapy is a treatment with a JAK2 inhibitor which is not N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof.

Also provided herein are articles of manufacture or kits comprising (a) a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutical salt thereof or a hydrate thereof, and (b) a package insert or a label indicating that the compound can be used for ameliorating bone marrow cellularity and/or bone marrow fibrosis.

Also provided herein are articles of manufacture or kits comprising (a) a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutical salt thereof or a hydrate thereof, and (b) a package insert or a label indicating that the compound can be used for improving pruritus associated with myelofibrosis.

Also provided herein are articles of manufacture or kits comprising a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutical salt thereof or a hydrate thereof, and a package insert or a label indicating that the compound can be used for treating myelofibrosis in a subject, and that subject should discontinue the treatment upon indication of elevated levels of one or more enzymes or molecules selected from the group consisting of: amylase, lipase, aspartate aminotransferase (AST), alanine aminotransferase (ALT), and creatinine in the serum of the subject, and/or upon indication of one or more hematologic condition selected from the group consisting of anemia, thrombocytopenia, and neutropenia. In some embodiments, the package insert or the label further indicates that the compound can be discontinued without prior dose reduction. In some embodiments, the one or more of the elevated levels of the enzymes or molecules are Grade 4 events. In some embodiments, the one or more of the hematologic conditions are Grade 4 events.

In some embodiments, the package insert or the label is in a position which is visible to prospective purchasers. In some embodiments, the compound is in a unit dosage form or capsule form.

In some embodiments, the package insert or the label indicates that, upon administration of the admixture to a human subject, the Cmax of the compound is achieved within about 2 to about 4 hours post-dose. In some embodiments, the package insert or the label indicates that, upon administration of the compound to a human subject, the elimination half life of the compound is about 16 to about 34 hours. In some embodiments, the package insert or the label indicates that the mean AUC of the compound increases more than proportionally with increasing doses ranging from about 30 mg to about 800 mg per day. In some embodiments, the package insert or the label indicates that the accumulation of the compound is about 1.25 to about 4.0 fold at steady state when the compound is dosed once daily. In some embodiments, the compound is in an admixture of (i) a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, (ii) a microcrystalline cellulose, and (iii) sodium stearyl fumarate. In some embodiments, the weight ratio of the compound to microcrystalline cellulose in the admixture is between about 1:1.5 to 1:15, and wherein the weight for the compound is the free base moiety weight of the compound. In some embodiments, the weight ratio of the compound to sodium stearyl fumarate in the admixture is between about 5:1 to about 50:1, and wherein the weight for the compound is the free base moiety weight of the compound. In some embodiments, the compound is N-tert-butyl-3-[(5-methyl-2-{[4-(2-pyrrolidin-1-ylethoxy)phenyl]amino}pyrimidin-4-yl)amino]benzenesulfonamide dihydrochloride monohydrate. In some embodiments, the microcrystalline cellulose is silicified microcrystalline cellulose.

In some embodiments, there is provided use of a compound in the manufacture of a medicament for treating myelofibrosis in a subject, wherein the compound is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof. In some embodiments, the compound is in an admixture of (i) the compound, (ii) an excipient (e.g., microcrystalline cellulose such as silicified microcrystalline cellulose), and (iii) a lubricant (e.g., sodium stearyl fumarate). In some embodiments, the compound is administered orally. In some embodiments, the use is according to a method described herein.

In some embodiments, there is provided use of a compound in the manufacture of a medicament for treating myelofibrosis in a subject, wherein the compound is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, wherein the subject is negative for the valine 617 to phenylalanine mutation of human Janus Kinase 2 (JAK2) or negative for the mutation corresponding to the valine 617 to phenylalanine mutation of human JAK2. In some embodiments, there is provided use of a compound in the manufacture of a medicament for treating myelofibrosis in a subject, wherein the compound is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, wherein the subject has previously received another myelofibrosis therapy. In some embodiments, the previous therapy comprises a JAK2 inhibitor which is not N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof. In some embodiments, the use is according to a method described herein.

In some embodiments, there is provided a compound for treating myelofibrosis in a subject, wherein the compound is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof. In some embodiments, the compound is in an admixture of (i) the compound, (ii) an excipient (e.g., microcrystalline cellulose such as silicified microcrystalline cellulose), and (iii) a lubricant (e.g., sodium stearyl fumarate). In some embodiments, the compound is administered orally. In some embodiments, the treatment is according to a method described herein.

In some embodiments, there is provided a compound for treating myelofibrosis in a subject, wherein the compound is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, wherein the subject is negative for the valine 617 to phenylalanine mutation of human Janus Kinase 2 (JAK2) or negative for the mutation corresponding to the valine 617 to phenylalanine mutation of human JAK2. In some embodiments, there is provided a compound for treating myelofibrosis in a subject, wherein the compound is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, wherein the subject has previously received another myelofibrosis therapy. In some embodiments, the previous therapy comprises a JAK2 inhibitor which is not N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof. In some embodiments, the treatment is according to a method described herein.

It is to be understood that one, some, or all of the properties of the various embodiments described herein may be combined to form other embodiments of the compositions and methods provided herein. These and other aspects of the compositions and methods provided herein will become apparent to one of skill in the art.

BRIEF DESCRIPTION OF THE FIGURES

FIG. 1 shows decrease in palpable spleen size by cycle for patients treated with TG101348 680 mg/day (starting dose) (N=37). Doses for cycle 1 were 520-800 mg/day and doses for cycles 2-6 were 360-680 mg/day. For cycle 6≥50% subjects, there was 22-47% increase in 3 subjects with drug held for ~2-3 weeks immediately prior to measurement.

FIG. 2 shows WBC count in subjects treated with TG101348. The baseline WBC count was >11×10$^9$/L. The doses at follow-up ranged from 360 to 680 mg/day. Last follow-up visit ranged from 8 to 24 weeks (median 24 weeks). "ULN" means upper limit of normal.

FIG. 3 shows platelet count in subjects treated with TG 101348. The baseline platelet count>450×10$^9$/L. The doses at follow-up ranged from 360 to 680 mg/day. Last follow-up visit ranged from 12 to 24 weeks (median 24 weeks). "ULN" means upper limit of normal.

FIG. 4 shows the percentages of subjects with worsened, unchanged, improved or resolved constitutional symptoms (fatigue, early satiety, cough, night sweats, and pruritus) in subjects treated with TG101348. Last visit ranged from 4 to 24 weeks (median 20 weeks). The data here reflected changes from symptoms present at baseline. 18 subjects reported new onset of ≥1 symptom during the study; of these, symptoms for 12 subjects were resolved by last follow-up visit. Severity was rated by subjects on a scale of 1-10: 0=absent; 1-3=mild; 4-7=moderate; 8-10=severe. Improved=downgrade to absent or to mild or moderate from more severe rating at baseline.

FIG. 5 shows the cytokine levels (IL-6, IL-8, IL-2 and TNF-α) in subjects treated with TG101348. The values shown are median values.

FIG. 6 shows the change in V617F allele burden from baseline as a proportion of baseline in subjects with baseline>20% (N=22) treated with TG101348. The figure shows the subset of JAK2V617F positive subjects in the overall population (N=48). The doses at follow-up were 360 to 680 mg/day. Last follow-up visit ranged from 20 to 72 weeks (median 24 weeks).

FIG. 7 shows the bone marrow cellularity at baseline (60% cellularity) and after 18 cycles of TG101348 treatment (5-10% cellularity) in a 76-year-old male subject with V617F negative PMF. The starting dose was 30 mg/day and the dose at follow-up was 520 mg/day.

FIG. 8 shows the bone marrow fibrosis at baseline (3+) and after 18 cycles of TG101348 treatment (0) in a 56-year-old male subject with V617F negative PMF. The starting dose was 240 mg/day and the dose at follow-up was 440 mg/day.

FIG. 9 shows various measurements of a subject with JAK2 V617F-positive PMF treated with TG101348 (starting dose at 680 mg/day).

FIGS. 14A-14C show effects of TG101348 on symptoms of myelofibrosis. (A): Proportion of subjects in maximum tolerated dose cohort with complete resolution of early satiety by cycle from a baseline symptom score of "mild" (score=11-3), "moderate" (score=4-7), or "severe" (score=8-10). Twenty-seven (79%) and 19 (56%) patients were evaluable for improvement in early satiety at the end of 1 and 6 cycles, respectively. After 2 cycles of treatment, 56% reported complete resolution of this symptom with durable benefit. (B): Proportion of subjects in maximum tolerated dose cohort with complete resolution of fatigue by cycle from a baseline symptom score of "mild" (score=1-3), or improvement in or complete resolution of fatigue from a baseline score of "moderate" (score=4-7) or "severe" (score=8-10). Twenty-four (71%) and 16 (47%) patients were evaluable for improvement in fatigue at the end of 1 and 6 cycles, respectively. After 6 cycles, 63% reported improvement and 25% had complete resolution of this symptom. (C): Proportion of subjects in maximum tolerated dose cohort with complete resolution of night sweats by cycle from a baseline symptom score of "mild" (score=1-3), "moderate" (score=4-7), or "severe" (score=8-10). Fourteen (40%) and 9 (26%) patients were evaluable for improvement in night sweats at the end of 1 and 6 cycles, respectively. After 1 cycle, 64% of subjects had complete resolution of this symptom; after 6 cycles, this proportion had increased to 89%.

FIGS. 16C and 16D). The y-axis represents the JAK2V617F allele burden from 1.0 (100%) to 0.0 (0%). The change in JAK2V617F allele burden per cycle of treatment (up to end of cycle 12; i.e. C13D1) as compared to pre-study baseline is shown for the 2 groups (FIGS. 16A and 16C); the change at the end of cycle 6 (i.e. C7D1) and cycle 12 is shown in FIGS. 16B and 16D. A significant decrease in JAK2V617F allele burden as compared to pre-study baseline was observed at the end of cycle 6 for the mutation-positive group (FIG. 16B; p=0.04) and the subgroup with baseline allele burden>20% (FIG. 16D; p=0.002); a similar significant decrease was seen at the end of cycle 12 for the former (FIG. 16B; p=0.01) and latter (FIG. 16D; p=0.00$^2$) groups. The Wilcoxon matched-pair signed-rank test was used to compare the median JAK2V617F allele burden for the comparisons.

DETAILED DESCRIPTION

I. Definitions

Figure 10A:
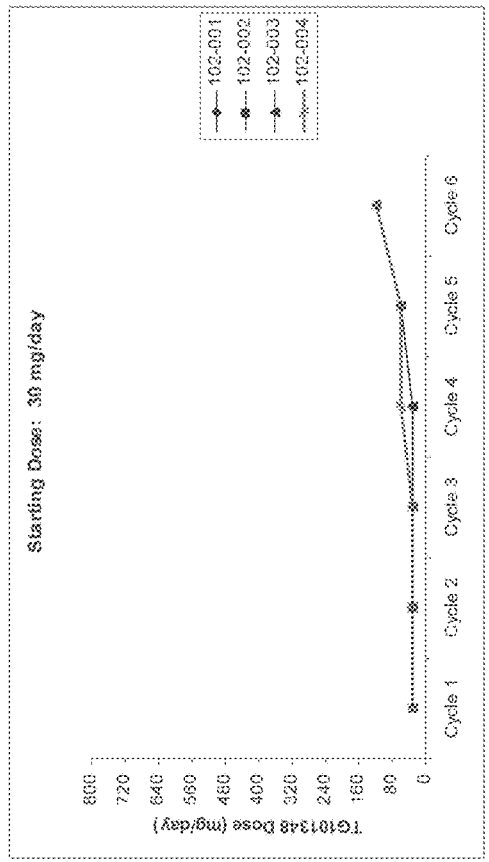
FIGS. 10A-10G show distribution of TG101348 doses at the end of each cycle for subjects who initiated dosing at 30 mg/day, 60 mg/day, 120 mg/day, 240 mg/day, 360 mg/day, 520 mg/day, and 800 mg/day, respectively, (n=25).
Figure 10B:
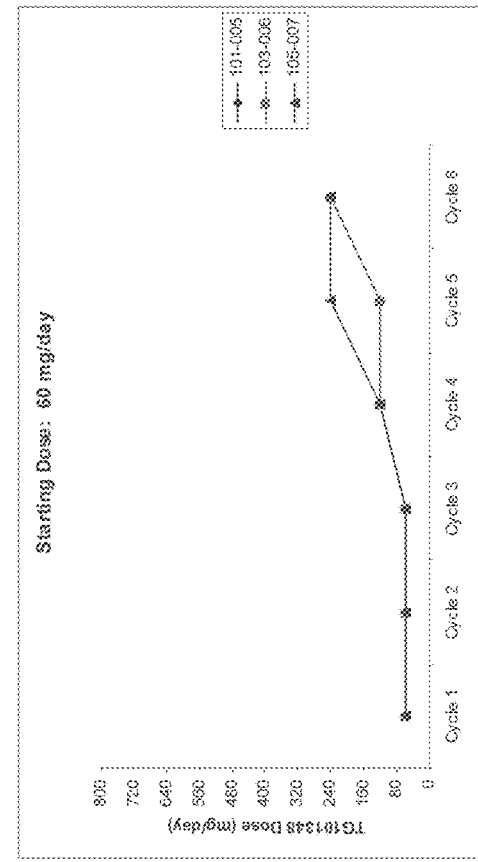
Figures 10C, 10D:
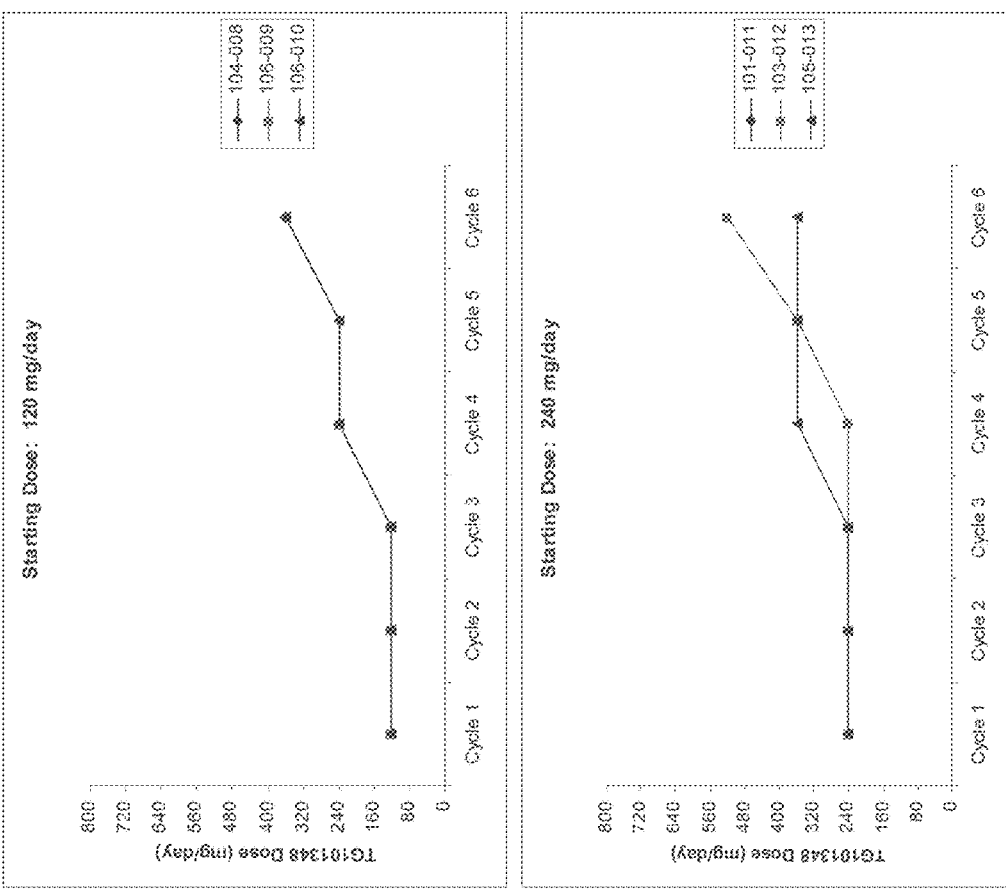
Figure 10E:
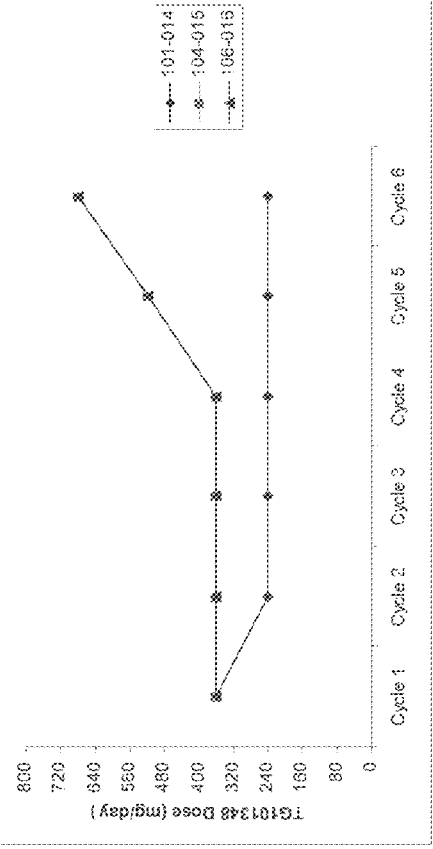
Figure 10F:
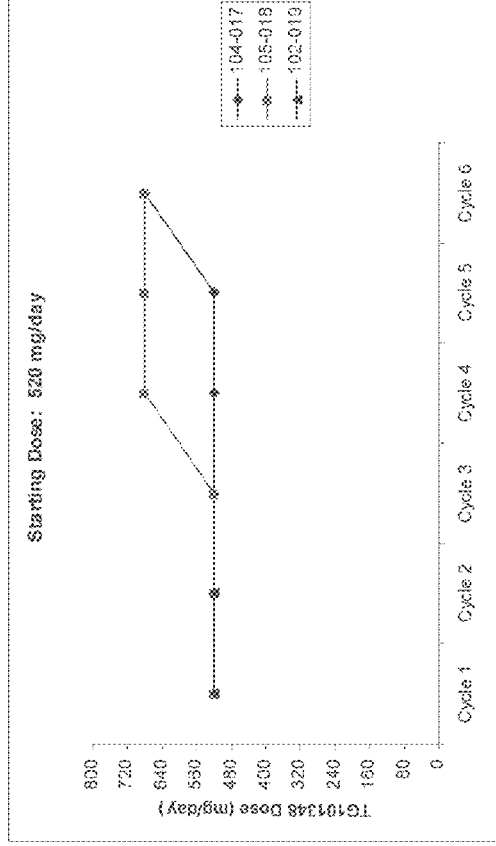
Figure 10G:
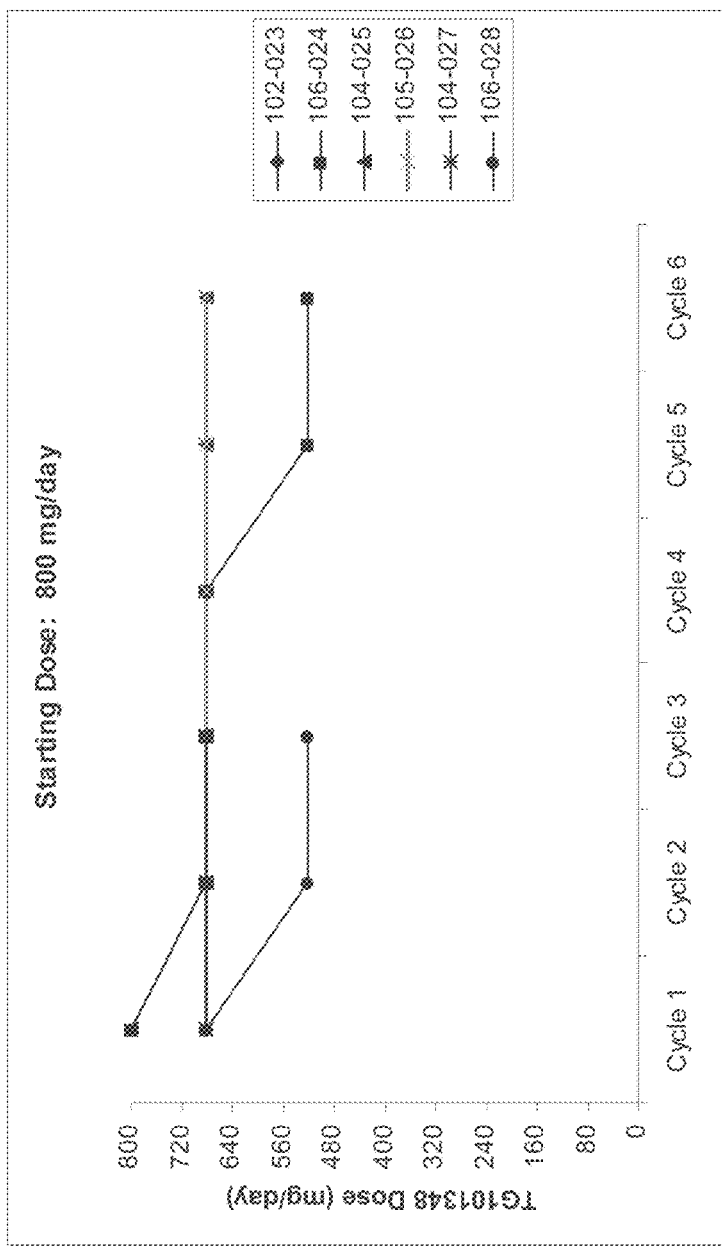

As used herein, "treatment" or "treating" is an approach for obtaining beneficial or desired results including clinical results. Beneficial or desired clinical results can include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals. In some embodiments, for the treatment of myelofibrosis, beneficial clinical results include one or more of reduction of splenomegaly, improvement in constitutional symptoms (such as early satiety, fatigue, night sweats, cough, and pruritus), reduction of leukocytosis, reduction of thrombocytosis, decrease of JAK2V617F allele burden, reduction of bone marrow fibrosis, and/or reduction of bone marrow cellularity.

As used herein, "delaying development of a disease" means to defer, hinder, slow, retard, stabilize, and/or postpone development of the disease (such as myelofibrosis) or symptoms of the disease, and can include "progression free survival". This delay can be of varying lengths of time, depending on the history of the disease and/or individual being treated. As is evident to one skilled in the art, a sufficient or significant delay can, in effect, encompass prevention, in that the individual does not develop the disease.

As used herein, an "effective dosage" or "effective amount" of drug, compound, or pharmaceutical composition is an amount sufficient to effect beneficial or desired results. For prophylactic use, beneficial or desired results can include, for example, one or more results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results can include, include, for example one or more clinical results such as decreasing one or more symptoms and pathological conditions resulting from or associated with the disease, increasing the quality of life of those suffering from the disease, decreasing the dose of other medications required to treat the disease, enhancing effect of another medication such as via targeting, delaying the progression of the disease, and/or prolonging survival. In the case of myelofibrosis, an effective amount of a drug may have the effect in reducing one or more of splenomegaly, improving constitutional symptoms (such as early satiety, fatigue, night sweats, cough, and pruritus), reducing leukocytosis, reducing thrombocytosis, decreasing JAK2V617F allele burden, reducing bone marrow fibrosis, and/or reducing bone marrow cellularity. An effective dosage can be administered in one or more administrations. An effective dosage of drug, compound, or pharmaceutical composition can be, for example, an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "ameliorating" bone marrow cellularity or bone marrow fibrosis refers to reducing the level of bone marrow cellularity or bone marrow fibrosis in a subject compared to the level of bone marrow cellularity or bone marrow fibrosis prior to commencing treatment with the compound provided herein. The reduction of bone marrow cellularity or bone marrow fibrosis can be at least by 5, 10, 20, 30, 40, 50, 60, 70, 80, or 90%.

As used herein, "in conjunction with" refers to administration of one treatment modality in addition to another treatment modality. As such, "in conjunction with" can refer to administration of one treatment modality before, during or after administration of the other treatment modality to the individual.

As used herein, a "patient" or a "subject" refers to a mammal including a human, a dog, a horse, a cow or a cat, etc.

The term "pharmaceutically acceptable" refers to the fact that the carrier, diluent or excipient must be compatible with the other ingredients of the formulation and can be administered to a subject.

As used herein, "pharmaceutically acceptable salts" refer to derivatives of the disclosed compounds wherein the parent compound is modified by making acid or base salts thereof.

As used herein and in the appended claims, the singular forms "a," "an," and "the" include plural reference unless the context clearly indicates otherwise.

Reference to "about" a value or parameter herein includes (and describes) embodiments that are directed to that value or parameter per se. For example, description referring to "about X" includes description of "X."

It is understood that aspects and variations of the compositions and methods provided herein can include "consisting" and/or "consisting essentially of" aspects and variations.

II. Compounds and Pharmaceutical Compositions

Provided herein is a compound which is N-tert-butyl-3-[(5-methyl-2-{[4-(2-pyrrolidin-1-ylethoxy)phenyl]amino}-pyrimidin-4-yl)amino]benzenesulfonamide or a pharmaceutically acceptable salt thereof or a hydrate thereof. Also provided herein are pharmaceutical compositions comprising N-tert-butyl-3-[(5-methyl-2-{[4-(2-pyrrolidin-1-ylethoxyphenyl]amino}pyrimidin-4-yl)amino]benzenesulfonamide or a pharmaceutically acceptable salt thereof or a hydrate thereof, and a pharmaceutically acceptable excipient or carrier. The compound and the pharmaceutical compositions described herein can be used for treating or delaying development of myelofibrosis in a subject. N-tert-Butyl-3-[(5-methyl-2-{[4-(2-pyrrolidin-1-ylethoxy)phenyl]amino} pyrimidin-4-yl)amino]benzenesulfonamide has the following chemical structure:

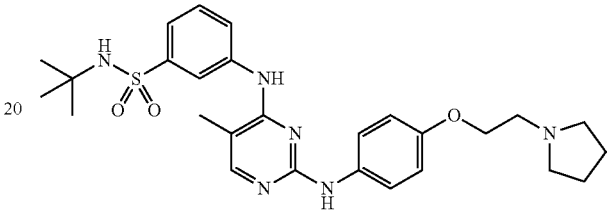

The compound provided herein may be formulated into therapeutic compositions as natural or salt forms. Pharmaceutically acceptable non-toxic salts include the base addition salts (formed with free carboxyl or other anionic groups) which may be derived from inorganic bases such as, for example, sodium hydroxide, potassium hydroxide, ammonium hydroxide, calcium hydroxide, or ferric hydroxide, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric acid, sulfuric acid, or phosphoric acid, or organic acids such as acetic acid, citric acid, p-toluenesulfonic acid, methanesulfonic acid, oxalic acid, tartaric acid, mandelic acid, and the like.

Salts of the compounds provided herein can include amine salts formed by the protonation of an amino group with inorganic acids such as hydrochloric acid, hydrobromic acid, hydroiodic acid, sulfuric acid, phosphoric acid, and the like. Salts of the compounds provided herein can also include amine salts formed by the protonation of an amino group with suitable organic acids, such as p-toluenesulfonic acid, acetic acid, methanesulfonic acid and the like. Additional excipients which are contemplated for use in the practice of the compositions and methods provided herein are those available to those of ordinary skills in the art, for example, those found in the United States Pharmacopeia Vol. XXII and National Formulary Vol. XVII, U.S. Pharmacopeia Convention, Inc., Rockville, Md. (1989), the relevant contents of which are incorporated herein by reference.

In addition, the compounds provided herein can include polymorphs. The compound described herein may be in alternative forms. For example, the compound described herein may include a hydrate form. As used herein, "hydrate" refers to a compound provided herein which is associated with water in the molecular form, i.e., in which the H—OH bond is not split, and may be represented, for example, by the formula $R.H_2O$, where R is a compound provided herein. A given compound may form more than one hydrate including, for example, monohydrates ($R.H_2O$)

or polyhydrates (R.nH$_2$O wherein n is an integer greater than 1) including, for example, dihydrates (R.2H$_2$O), trihydrates (R.3H$_2$O), and the like, or fractional hydrates, such as, for example, R.n/2H$_2$O, R.n/3H$_2$O, R.n/4H$_2$O and the like wherein n is an integer.

The compounds described herein may also include acid salt hydrate forms. As used herein, "acid salt hydrate" refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

In some embodiments, the compound is N-tert-butyl-3-[(5-methyl-2-{[4-(2-pyrrolidin-1-ylethoxy)phenyl]amino}pyrimidin-4-yl)amino]benzenesulfonamide dihydrochloride monohydrate and has the following chemical structure:

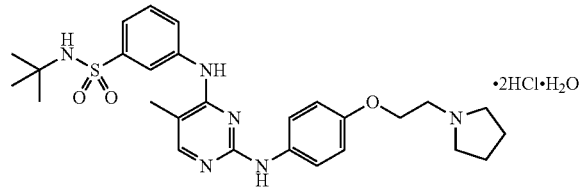 [SMILES: Cc1cnc(Nc2ccc(OCCN3CCCC3)cc2)nc1Nc1cccc(S(=O)(=O)NC(C)(C)C)c1]

The pharmaceutical compositions for the administration of the compound described herein, either alone or in combination with other therapeutic agents, may conveniently be presented in dosage unit form and may be prepared by any of the methods well known in the art of pharmacy and methods described in Examples 4, 5 and 6. Such methods can include bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. The pharmaceutical compositions containing the active ingredient may be in a form suitable for oral use, for example, as hard or soft capsules. The suitable capsule shell may be hard gelatin or hydroxypropylmethyl cellulose ("HPMC").

Provided herein are formulations comprising (i) a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, (ii) one or more excipients, and (iii) one or more lubricants. The formulations may be in capsule form and administered orally. The formulations may be in unit dosage form. In some embodiments, the excipient is lactose (such as Fast-Flo), mannitol (such as Parteck M200), microcrystalline cellulose ("MCC") (such as Avicel PH102), MCC (such as ProSolv 90 HD). In some embodiments, the lubricant is magnesium stearate, sodium stearyl fumarate (such as Pruv), or sodium laurel fumarate. In some embodiments, the microcrystalline cellulose is silicified microcrystalline cellulose. In some embodiments, the capsule is hard gelatin capsule.

In some embodiments, there is provided a capsule suitable for oral administration comprising an admixture of (i) a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, (ii) an excipient (e.g., microcrystalline cellulose such as silicified microcrystalline cellulose), and (iii) a lubricant (e.g., sodium stearyl fumarate), wherein the admixture is contained in the capsule. Methods known in the art and described herein may be used for making the capsules. See, e.g., Example 3. Microcrystalline cellulose may be used as a filler and/or diluent in the capsules provided herein. Sodium stearyl fumarate may be used as a lubricant in the capsules provided herein. In some embodiments, the microcrystalline cellulose is silicified microcrystalline cellulose. For example, silicified microcrystalline cellulose may be composed of microcrystalline cellulose and colloidal silicon dioxide particles. In some embodiments, the silicified microcrystalline cellulose is a combination of 98% microcrystalline cellulose and 2% colloidal silicon dioxide.

In some embodiments, the capsule contains about 10 mg to about 680 mg of the compound, wherein the specified weight is the free base moiety weight of the compound. In some embodiments, the capsule contains about 10 mg to about 650 mg (or about 10 mg to about 550 mg or about 10 mg to about 500 mg), wherein the specified weight is the free base moiety weight of the compound. In some embodiments, the capsule contains about 100 mg to about 600 mg (or about 200 mg to about 550 mg or about 300 mg to about 500 mg), wherein the specified weight is the free base moiety weight of the compound. In some embodiments, the capsule contains about 10 mg, about 20 mg, about 40 mg, about 100 mg, about 150 mg, about 200 mg, about 250 mg, about 300 mg, about 350 mg, about 400 mg, about 450 mg, about 500 mg, about 550 mg, about 600 mg, or about 650 mg of the compound, wherein the specified weight is the free base moiety weight of the compound. In some embodiments, the capsule is a hard gelatin capsule. In some embodiments, the compound is N-tert-butyl-3-[(5-methyl-2-([4-(2-pyrrolidin-1-ylethoxy)phenyl]amino pyrimidin-4-yl)amino]benzenesulfonamide dihydrochloride monohydrate.

In some embodiments, the weight ratio of the compound to excipient (e.g., microcrystalline cellulose such as silicified microcrystalline cellulose) in the capsule is between about 1:1.5 to about 1:15 (e.g., between about 1:5 to about 1:10, between about 1:5 to about 1:12, or between about 1:10 to about 1:15), wherein the weight of the compound is the free base moiety weight of the compound. In some embodiments, the weight ratio of the compound to lubricant (e.g., sodium stearyl fumarate) in the capsule is between about 5:1 to about 50:1 (e.g., between about 5:1 to about 10:1, between about 5:1 to about 25:1, between about 5:1 to about 40:1, between about 7:1 to about 34:1, or between about 8:1 to about 34:1), wherein the weight of the compound is the free base moiety weight of the compound.

In some embodiments, the capsule contains about 5% to about 50% (e.g., about 5% to about 10% or about 5% to about 35%) compound of the total fill weight of the capsule, wherein the weight of the compound is the free base moiety weight of the compound. In some embodiments, the capsule contains about 40% to about 95% (e.g., about 50% to about 90% or about 60% to about 90%) excipient (e.g., microcrystalline cellulose such as silicified microcrystalline cellulose) of the total fill weight of the capsule. In some embodiments, the capsule contains about 0.2% to about 5% (e.g., about 0.2% to about 2% or about 0.5% to about 1.5%, or about 0.5%, about 1%, or about 1.5%) lubricant (e.g., sodium stearyl fumarate) of the total fill weight of the capsule.

Also provided herein are unit dosage forms comprising an admixture of (i) a compound which is N-tert-butyl-3-[(5-methyl-2-[4-(2-pyrrolidin-1-ylethoxy)phenyl]amino pyrimidin-4-yl)amino]benzenesulfonamide or a pharmaceutically acceptable salt thereof or a hydrate thereof, (ii) an excipient (such as microcrystalline cellulose), and (iii) a lubricant (such as sodium stearyl fumarate). Any one of the capsules described herein may be used in a unit dosage form. In some embodiments, the unit dosage form is for treating myelofibrosis. In some embodiments, the treatment is according to a method described herein.

In some embodiments, the unit dosage form comprises an admixture of (i) about 10 mg to about 680 mg (or about 10 mg to about 500 mg) of a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, wherein the specified weight is the free base moiety weight of the compound, (ii) a microcrystalline cellulose, and (iii) sodium stearyl fumarate. In some embodiments, the compound in the admixture is about 10 mg to about 500 mg, wherein the specified weight is the free base moiety weight of the compound.

In some embodiments, the unit dosage form is in the form of a capsule, and the admixture is contained in the capsule. In some embodiments, the unit dosage form comprises about 10 mg, about 20 mg, about 40 mg, about 100 mg, about 150 mg, about 200 mg, about 250 mg, about 300 mg, about 350 mg, about 400 mg, about 450 mg, about 500 mg, about 550 mg, about 600 mg, or about 650 mg of the compound, wherein the specified weight is the free base moiety weight of the compound. In some embodiments, the compound is N-tert-butyl-3-[(5-methyl-2-{[4-(2-pyrrolidin-1-ylethoxy)phenyl]amino}pyrimidin-4-yl)amino]benzenesulfonamide dihydrochloride monohydrate. In some embodiments, the admixture comprises (i) about 10 mg (or about any of 40 mg, 100 mg, 200 mg, 300 mg, 400 mg, or 500 mg) of the compound, (ii) a microcrystalline cellulose, and (iii) sodium stearyl fumarate, wherein the specified weight is the free base moiety weight of the compound. In some embodiments, the compound is N-tert-butyl-3-[(5-methyl-2-{[4-(2-pyrrolidin-1-ylethoxy)phenyl]amino}pyrimidin-4-yl)amino]benzenesulfonamide dihydrochloride monohydrate.

In some embodiments, the weight ratio of the compound to excipient (e.g., microcrystalline cellulose such as silicified microcrystalline cellulose) in the unit dosage form is between about 1:1.5 to about 1:15 (e.g., between about 1:5 to about 1:10, between about 1:5 to about 1:12, or between about 1:10 to about 1:15), wherein the weight of the compound is the free base moiety weight of the compound. In some embodiments, the weight ratio of the compound to lubricant (e.g., sodium stearyl fumarate) in the unit dosage form is between about 5:1 to about 50:1 (e.g., between about 5:1 to about 10:1, between about 5:1 to about 25:1, between about 5:1 to about 40:1, between about 7:1 to about 34:1, or between about 8:1 to about 34:1), wherein the weight of the compound is the free base moiety weight of the compound. In some embodiments, the microcrystalline cellulose is silicified microcrystalline cellulose. In some embodiments, the silicified microcrystalline cellulose is a combination of 98% microcrystalline cellulose and 2% colloidal silicon dioxide.

In some embodiments, the lubricant (e.g., sodium stearyl fumarate) is about 0.1% to about 10%, about 0.5% to about 5%, about 0.5% to about 3%, about 0.5% to about 2%, about 0.75% to about 1.5% of the capsule fill weight. In some embodiments, the lubricant (e.g., sodium stearyl fumarate) is at least about any one of 0.1%, 0.25%, 0.5%, 0.75%, 1%, 1.25%, 1.5%, 1.75%, 2%, 2.5%, 3%, 3.5%, 4%, 4.5%, or 5% of the capsule fill weight. In some embodiments, the lubricant (e.g., sodium stearyl fumarate) is about any one of 0.1%, 0.25%, 0.5%, 0.75%, 1%, 1.25%, 1.5%, 1.75%, 2%, 2.5%, 3%, 3.5%, 4%, 4.5%, or 5% of the capsule fill weight.

In some embodiments, the weight ratio of a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof to an excipient (e.g., microcrystalline cellulose such as silicified microcrystalline cellulose) in a capsule or unit dosage form is about 40:60 to about 10:90. In some embodiments, the weight ratio of the compound to an excipient (e.g., microcrystalline cellulose such as silicified microcrystalline cellulose) in a capsule of unit dosage form is about any one of 95:5, 90:10, 85:15, 80:20, 75:25, 70:30, 65:35, 60:40, 55:45, 50:50, 45:55, 40:60, 35:65, 30:70, 25:75, 20:80, 15:85, 10:90, or 5:95. In some embodiments, the weight ratio of the compound to an excipient (e.g., microcrystalline such as silicified microcrystalline cellulose) is about 1:1.5 to about 1:9.5, such as about any of 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, or 1:9.5. In some embodiments, the compound is N-tert-butyl-3-[(5-methyl-2-{[4-(2-pyrrolidin-1-ylethoxy)phenyl]amino}pyrimidin-4-yl)amino]benzenesulfonamide dihydrochloride monohydrate.

In some embodiments, the capsule contains about 5% to about 50% (e.g., about 5% to about 10% or about 5% to about 35%) compound of the total weight of the admixture, wherein the weight of the compound is the free base moiety weight of the compound. In some embodiments, the capsule contains about 40% to about 95% (e.g., about 50% to about 90% or about 60% to about 90%) microcrystalline cellulose (such as silicified microcrystalline cellulose) of the total weight of the admixture. In some embodiments, the capsule contains about 0.2% to about 5% (e.g., about 0.2% to about 2% or about 0.5% to about 1.5%, or about 0.5%, about 1%, or about 1.5%) sodium stearyl fumarate of the total weight of the admixture.

In some embodiments, the capsule or unit dosage form contains an admixture of about 12 mg of N-tert-butyl-3-[(5-methyl-2-{[4-(2-pyrrolidin-1-ylethoxy)phenyl]amino}pyrimidin-4-yl)amino]benzenesulfonamide dihydrochloride monohydrate, about 122 mg of silicified microcrystalline cellulose, and about 1 mg of sodium stearyl fumarate. In some embodiments, the capsule or unit dosage form contains an admixture of about 47 mg of N-tert-butyl-3-[(5-methyl-2-{[4-(2-pyrrolidin-1-ylethoxy)phenyl]amino}pyrimidin-4-yl)amino]benzenesulfonamide dihydrochloride monohydrate, about 448 mg of silicified microcrystalline cellulose, and about 5 mg of sodium stearyl fumarate. In some embodiments, the capsule or unit dosage form contains an admixture of about 117 mg of N-tert-butyl-3-[(5-methyl-2-{[4-(2-pyrrolidin-1-ylethoxy)phenyl]amino}pyrimidin-4-yl)amino]benzenesulfonamide dihydrochloride monohydrate. In some embodiments, the capsule or unit dosage form contains an admixture of about 235 mg of N-tert-butyl-2-{([4-(2-pyrrolidin-1-ylethoxy)

phenyl]amino}pyrimidin-4-yl)amino]benzenesulfonamide dihydrochloride monohydrate, about 357 mg of silicified microcrystalline cellulose, and about 6.00 mg of sodium stearyl fumarate.

Also provided herein are oral solution formulations comprising a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof. In some embodiments, the oral solution formulation further comprises methylcellulose. In some embodiments, the oral solution formulation further comprises methylcellulose and Tween 80. In some embodiments, the oral solution formulation comprises the compound at about 1 mg/ml to about 25 mg/ml, about 2 mg/ml to about 20 mg/ml, about 3 mg/ml to about 15 mg/ml, about 5 mg/ml to about 10 mg/ml. In some embodiments, the oral solution formulation comprises the compound at about any one of 2 mg/ml, 3 mg/ml, 4 mg/ml, 5 mg/ml, 6 mg/ml, 6.25 mg/ml, 6.5 mg/ml, 7 mg/ml, 8 mg/ml, 9 mg/ml, 10 mg/ml, or 12.5 mg/ml, or 15 mg/ml. In some embodiments, the oral solution formulation comprises about 0.1% to about 5%, 0.2% to about 3%, about 0.25% to about 2%, about 0.25% to about 1%, or about 0.5% by weight of methylcellulose. In some embodiments, the oral solution formulation comprises about 0.01% to about 0.5%, 0.02% to about 0.3%, about 0.025% to about 0.2%, about 0.025% to about 0.1%, or about 0.05% by weight of Tween 80.

In some embodiments, the capsule does not comprise an absorption enhancer. In some embodiments, the capsule comprises an absorption enhancer (e.g., Vitamin E TPGS, Gelucire 44/14, Pluronic F127, or glyceryl monostearate).

A capsule or unit dosage form provided may comprise one or more of the following properties: (1) upon administration to a subject such as human subject, the Cmax of the compound is achieved within about 2 to about 4 hours post-dose; (2) upon administration to a human subject, the elimination half life of the compound is about 16 to about 34 hours; (3) the mean AUC of the compound increases more than proportionally with increasing doses ranging from about 30 mg to about 800 mg per day; (4) the accumulation of the compound is about 1.25 to about 4.0 fold at steady state when the compound is dosed once daily.

Also provided are methods of preparing a capsule drug product comprising a) blending a lubricant with a compound that is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof to generate granules and b) mixing the granules of a) with an excipient. In some embodiments, the lubricant is sodium stearyl fumarate. In some embodiments, the excipient is microcrystalline cellulose such as silicified microcrystalline cellulose. Such method may be used to prepare a capsule or unit dosage form described herein. The weight (such as weight ratio or weight percentage) and components regarding the compound, excipient, and/or lubricant may be according to any described herein.

III. Methods of Treatment and Prevention of Myelofibrosis

Provided herein are methods for treating, delaying development, and/or preventing myelofibrosis in a subject comprising administering to the subject an effective amount of a compound which is N-tert-butyl-3-[(5-methyl-2-{[4-(2-pyrrolidin-1-ylethoxy)phenyl]amino}pyrimidin-4-yl)amino] benzenesulfonamide or a pharmaceutically acceptable salt thereof or a hydrate thereof (e.g., N-tert-butyl-3-[(5-methyl-2-{[4-(2-pyrrolidin-1-ylethoxy)phenyl]amino}pyrimidin-4-yl)amino]benzenesulfonamide dihydrochloride monohydrate). In some embodiments, the subject has myelofibrosis. In some embodiments, the subject is at risk of developing myelofibrosis. In some embodiments, the subject is a human subject. Any one of the formulations described herein such as capsule or unit dosage forms described herein may be used to treat a subject with myelofibrosis. In some embodiments, the compound is in an admixture of (i) a compound which is N-tert-butyl-3-[(5-methyl-2-{([4-(2-pyrrolidin-1-ylethoxy)phenyl]amino}pyrimidin-4-yl)amino]benzenesulfonamide or a pharmaceutically acceptable salt thereof or a hydrate thereof, (ii) an excipient (such as microcrystalline cellulose), and (iii) a lubricant (such as sodium stearyl fumarate).

Myelofibrosis that may be treated by the compounds described herein includes primary myelofibrosis (MF) and secondary myelofibrosis (e.g., myelofibrosis arising from antecedent polycythemia vera (post-PV MF) or essential thrombocythemia (post-ET MF)). Myelofibrosis that may be treated by the compounds described herein also includes myelofibrosis of high risk, intermediate risk such as intermediate risk level 2. Methods for diagnosing various types of myelofibrosis are known in the art. See, e.g., Cervantes et al., Blood 2009. In some embodiments, the subject with myelofibrosis has spleen of at least 5 cm below costal margin as measured by palpation.

In some embodiments, the subject has a point mutation from valine 617 to phenylalanie in the Janus kinase 2 (JAK2 kinase) (JAK2V617F) if the subject is a human, or a point mutation corresponding to the valine 617 to phenylalanie in the Janus kinase 2 (JAK2 kinase) if the subject is not a human. In some embodiments, the subject is negative for the valine 617 to phenylalanine mutation of JAK2 if the subject is a human, or negative for a mutation corresponding to the valine 617 to phenylalanie in the Janus kinase 2 (JAK2 kinase) if the subject is not a human. Whether a subject is positive or negative for JAK2V617F can be determined by a polymerase chain reaction ("PCR") analysis using genomic DNA from bone marrow cells or blood cells (e.g., whole blood leukocytes). The PCR analysis can be an allele-specific PCR (e.g., allele-specific quantitative PCR) or PCR sequencing. See Kittur J et al., Cancer 2007, 109(11): 2279-84 and McLornan D et al., Ulster Med J. 2006, 75(2): 112-9, each of which is expressly incorporated herein by reference.

In some embodiments, the subject treated with the methods described herein has previously received another myelofibrosis therapy or treatment. In some embodiments, the subject is a non-responder to the other myelofibrosis therapy or has a relapse after receiving the other myelofibrosis therapy. The previous therapy may be a JAK2 inhibitor (e.g. INCB018424 (also known as ruxolitinib, available from Incyte), CEP-701 (lestaurtinib, available from Cephalon), or XL019 (available from Exelixis)) (See Verstovsek S., Hematology Am Soc Hematol Educ Program. 2009:636-42) or a non-JAK2 inhibitor (such as hydroxyurea). In some embodiments, the subject has received ruxolitinib treatment for primary myelofibrosis, post-polycythemia vera myelofibrosis (Post-PV MF), post-essential thrombocythemia myelofibrosis (Post-ET MF), polycythemia vera, or essential thrombocythemia for at least 14 days and discontinued the treatment for at least 30 days. In some embodiments, the previous therapy is a treatment with a compound described herein and the previous therapy has been discontinued upon indication of one or more elevated levels of amylase, lipase, aspartate aminotransferase (AST), alanine aminotransferase (ALT), and/or creatinine in the serum from the subject, and/or upon indication of a hematologic condition selected from the group consisting of anemia, thrombocytopenia, and neutropenia. In some embodiments, the dose of the compound in the second treatment is the same or lower than the dose in the previous therapy.

The subject may be treated orally and/or daily. The subject (such as a human) may be treated by administering at a dose of about 240 mg per day to about 680 mg per day (or about 300 mg per day to about 500 mg per day), wherein the specified weight is the free base moiety weight of the compound. In some embodiment, the compound is administered at a dose of about any of 240 mg/day, 250 mg/day, 300 mg/day, 350 my/day, 400 mg/day, 450 mg/day, 500 mg/day, 550 mg/day, 600 mg/day, 650 mg/day, or 680 mg/day. The compound may be in a capsule and/or a unit dosage form described herein. In some embodiments, the compound administered is in an admixture with a microcrystalline cellulose and sodium stearyl fumarate, and the admixture is in a capsule. In some embodiments, the compound is administered orally.

Also provided herein are methods for ameliorating one or more symptoms associated with myelofibrosis. For example, the treatment using the compound described herein is effective in reducing spleen size, ameliorating constitutional symptoms (such as early satiety, fatigue, night sweats, cough, and pruritus), reducing leukocytosis, reducing thrombocytosis, decreasing JAK2V617F allele burden, reducing bone marrow fibrosis, improving pruritus, improving cachexia, and/or reducing bone marrow cellularity. The reduction, decrease, amelioration, or improvement can be at least by 5, 10, 20, 30, 40, 50, 60, 70, 80, or 90% compared to the level prior to commencing treatment with the compound provided herein. In some embodiment, the spleen becomes non-palpable in the subject after treatment. In some embodiments, the subject has complete resolution of leukocytosis and/or thrombocytosis after treatment. In some embodiments, the subject has complete resolution of pruritus after treatment.

In some embodiments, the compound is administered to the subject daily for at least 1 cycle, at least 2 cycles, at least 3 cycles, at least 4 cycles, at least 5 cycles, or at least 6 cycles of a 28-day cycle. In some embodiments, the compound is administered to the subject daily for at least 6 cycles of a 28-day cycle, at least 8 cycles of a 28-day cycle, at least 10 cycles of a 28-day cycle, at least 12 cycles of a 28-day cycle, at least 15 cycles of a 28-day cycle, at least 18 cycles of a 28-day cycle, or at least 24 cycles of a 28-day cycle. In some embodiments, the compound is administered to the subject daily for at least one month, at least two month, at least three month, at least four month, at least five month, at least six month, at least eight month, or at least one year. In some embodiments, the compound is administered once a day.

In some embodiments, upon administration of a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof to a subject such as human subject, the Cmax of the compound is achieved within about 1 to about 5 hours, about 1.5 to about 4.5 hours, about 2 to about 4 hours, or about 2.5 to about 3.5 hours post-dose. In some embodiments, upon administration of the compound to a human subject, the elimination half life of the compound is about 12 to about 40 hours, about 16 to about 34 hours, or about 20 to about 30 hours. In some embodiments, the mean AUC of the compound increases more than proportionally with increasing doses ranging from about 30 mg to about 800 mg per day. In some embodiments, the accumulation of the compound is about 1.1 to about 5 fold, about 1.25 to about 4.0 fold, about 1.5 to about 3.5 fold, about 2 to about 3 fold at steady state when the compound is dosed once daily.

In some embodiments, the method comprises instructing the subject to ingest the effective amount of the compound on an empty stomach. In some embodiments, the methods further comprise instructing the subject to avoid ingesting agents that are at least moderate inducers or inhibitors of CYP3A4. In some embodiments, the subject does not receive concomitant treatment with or use of drugs to herbal agents known to be at least moderate inhibitors or inducers of CYP3A4. Based on in vitro evaluations, N-tert-butyl-3-[(5-methyl-2-{[4-(2-pyrrolidin-1-ylethoxy)phenyl]amino}pyrimidin-4-yl)amino]benzenesulfonamide is metabolized by human CYP3A4. Agents that may increase N-tert-butyl-3-[(5-methyl-2-{[4-(2-pyrrolidin-1-ylethoxy)phenyl]amino}pyrimidin-4-yl)amino]benzenesulfonamide plasma concentrations (i.e., CYP3A4 inhibitors) or decrease N-tert-butyl-3-[(5-methyl-2-{[4-(2-pyrrolidin-1-ylethoxy)phenyl]amino}pyrimidin-4-yl)amino]benzenesulfonamide plasma concentrations (i.e., CYP3A4 inducers), including herbal agents and foods (e.g. grapefruit/grapefruit juice), should be avoided in subjects being treated as described herein. In addition, in vitro data have indicated that N-tert-butyl-3-[(5-methyl-2-{[4-(2-pyrrolidin-1-ylethoxy)phenyl]amino}pyrimidin-4-yl)amino]benzenesulfonamide inhibits CYP3A4 in a time-dependent fashion. Agents that are sensitive substrates for metabolism by CYP3A4 should be used with caution as coadministration with N-tert-butyl-3-[(5-methyl-2-{[4-(2-pyrrolidin-1-ylethoxy)phenyl]amino}pyrimidin-4-yl)amino]benzenesulfonamide may result in higher plasma concentrations of the coadministered agent. A list of clinically relevant substrates of CYP3A4 include alfentanil, Cyclosporine, Diergotamine, ethinyl estradiol, ergotamine, fentanyl, pimozide, quinidine, sirolimus, tacrolimus, clarithromycin erythromycin, telithromycin, alprazolam, diazepam, midazolam, triazolam, indinavir, ritonavir, saquinavir, prokinetic, cisapride, astemizole, chlorpheniramine, amlodipine, diltiazem, felodipine, nifedipine, verapamil, atorvastatin, cerivastatin, lovastatin, simvastatin, aripiprazole, gleevec, halopericol, sildenafil, tamoxifen, taxanes, trazodone, and Vincristine. A list of clinically relevant inducers of CYP3A4 include carbamazepine, phenobarbital, phenyloin, pioglitazone, rifabutin, rifampin, St. John's wort, and troglitazone. A list of clinically relevant inhibitors of CYP3A4 include indinavir, nelfinavir, ritonavir, clarithromycin, itraconazole, ketoconazole, nefazodone, erythromycin, grapefruit juice, verapamil, diltiazem, cimetidine, amiodarone, fluvoxamine, mibefradil, and Troleandomycin. See reference Flockhart et al., http://medicine.iupui.edu/clinpharm/ddis/clinicaltable.aspx., 2009.

Also provided herein are methods of monitoring treatment of myelofibrosis to a subject, comprising (a) administering to the subject an effective amount of a compound which is N-tert-butyl-3-[(5-methyl-2-{[4-(2-pyrrolidin-1-ylethoxy) phenyl]amino}pyrimidin-4-yl)amino]benzenesulfonamide or a pharmaceutically acceptable salt thereof or a hydrate thereof; (b) monitoring a hematologic parameter and/or a non-hematologic parameter in the subject; and (c) determining if the subject should continue or discontinue with the treatment. In some embodiments, the hematologic parameter is selected from the group consisting of anemia, thrombocytopenia, and neutropenia. In some embodiments, the non-hematologic parameter is an enzyme or molecule in the blood or serum wherein an elevated level of the enzyme or molecule is indicative of tissue or organ damage. In some embodiments, the serum enzyme or molecule can be, for example, amylase, lipase, aspartate aminotransferase (AST), alanine aminotransferase (ALT), creatinine, alkaline phosphatase, and calcium. Methods of monitoring these parameters are known in the art and are described herein. See Examples 1-3. In some embodiments, the method further comprises administering to the subject an effective amount of the compound described herein after the subject has been discontinued with the treatment for at least 2 week, at least 3 weeks, or at least 4 weeks. In some embodiments, the previous treatment has been discontinued without prior dose reduction.

Also provided herein are methods of monitoring treatment of myelofibrosis to a subject, comprising administering to the subject an effective amount of a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, and discontinuing the treatment upon indication of elevated levels of one or more enzymes or molecules selected from the group consisting of amylase, lipase, aspartate aminotransferase (AST), alanine aminotransferase (ALT), and creatinine and/or decreased level of calcium in the blood or serum of the subject without prior dose reduction. Also provided herein are methods of monitoring treatment of myelofibrosis to a subject, comprising administering to the subject an effective amount of a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, and discontinuing the treatment upon indication of one or more hematologic conditions selected from the group consisting of anemia, thrombocytopenia, and neutropenia without prior dose reduction. In some embodiments, the treatment is discontinued when one or more of the parameters (including hematologic and non-hematologic parameters) are grade 3 or 4 events.

Grade 3 or 4 adverse events for hematologic and non-hematologic parameters are known in the art and shown in the Table below. See, e.g. C Common Terminology Criteria for Adverse Events (CTCAE), Version 4.0, Published: May 28, 2009 (v4.03: Jun. 14, 2010).

| RESPONSE (hematologic and non-hematologic) | Definition | Grade 3 | Grade 4 |
|---|---|---|---|
| Hyperlipasemia | A finding based on laboratory test results that indicate an increase in the level of lipase in a biological specimen. | >2.0-5.0 × ULN* | >5.0 × ULN |
| Serum amylase | A finding based on laboratory test results that indicate an increase in the levels of amylase in a serum specimen. | >2.0-5.0 × ULN | >5.0 × ULN |
| Alanine aminotransferase increased | A finding based on laboratory test results that indicate an increase in the level of alanine aminotransferase (ALT or SGPT) in the blood specimen. | >5.0-20.0 × ULN | >20.0 × ULN |
| Aspartate aminotransferase increased | A finding based on laboratory test results that indicate an increase in the level of aspartate aminotransferase (AST or SGOT) in a blood specimen. | >5.0-20.0 × ULN | >20.0 × ULN |
| Blood creatinine increased | A finding based on laboratory test results that indicate increased levels of creatinine in a biological specimen. | >3.0 baseline; >3.0 | 6.0 × ULN >6.0 × ULN |
| Blood alkaline phosphatase increased | A finding based on laboratory test results that indicate an increase in the level of alkaline phosphatase in a blood specimen. | >5.0-20.0 × ULN | >20.0 × ULN |
| Hypocalcemia | A disorder characterized by laboratory test results that indicate a low concentration of calcium (corrected for albumin) in the blood. | Corrected serum calcium of <7.0-6.0 mg/dL; <1.75-1.5 mmol/L; Ionized calcium <0.9-0.8 mmol/L; hospitalization indicated | Corrected serum calcium of <6.0 mg/dL; <1.5 mmol/L; Ionized calcium <0.8 mmol/L; life-threatening consequences |
| Anemia | A disorder characterized by a reduction in the amount of hemoglobin in 100 ml of blood. Signs and symptoms of anemia | Hgb <8.0 g/dL; <4.9 mmol/L; <80 g/L; transfusion indicated | Life-threatening consequences; urgent intervention indicated |

| RESPONSE (hematologic and non-hematologic) | Definition | Grade 3 | Grade 4 |
|---|---|---|---|
| | may include pallor of the skin and mucous membranes, shortness of breath, palpitations of the heart, soft systolic murmurs, lethargy, and fatigability. | | |
| Thrombocytopenia | a platelet count below the normal range for the population ([+ or −] 2 standard deviations). In most laboratories, a normal platelet count is between 150,000 to 450,000/μL | 25,000 to <50,000/μL | below 25,000/μL |
| Neutropenia | A finding based on laboratory test results that indicate a decrease in number of neutrophils in a blood specimen. | <1000-500/mm3; <1.0-0.5 × $10^9$/L | <500/mm3; <0.5 × $10^9$/L |

*"ULN" refers to upper limit of normal.

IV. Articles of Manufactures and Kits

Also provided herein are articles of manufacture or kits containing a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof. In some embodiments, the article of manufacture or the kit further includes instructions for using the compounds described herein in the methods provided herein. In some embodiments, the article of manufacture or the kit further comprises a label or a package insert providing the instructions. In some embodiments, the compound is in a capsule and/or a unit dosage form described herein.

In some embodiments, the article of manufacture or kit may further comprise a container. Suitable containers include, for example, bottles, vials (e.g., dual chamber vials), syringes (such as single or dual chamber syringes) and test tubes. The container may be formed from a variety of materials such as glass or plastic, and the container may hold the compound, for example in the formulation to be administered. The article of manufacture or the kit may further comprise a label or a package insert, which is on or associated with the container, may indicate directions for reconstitution and/or use of the compound. In some embodiments, the package insert or the label is in a position which is visible to prospective purchasers.

The label or package insert may further indicate that the compound is useful or intended for treating or preventing myelofibrosis in a subject. In some embodiments, the package insert or the label indicates that the compound can be used for ameliorating bone marrow cellularity and/or bone marrow fibrosis. In some embodiments, the package insert or the label indicates that the compound can be used for treating myelofibrosis in a subject, wherein the subject is negative for the valine 617 to phenylalanine mutation of human JAK2 (JAK2V617F) or negative for the mutation corresponding to the valine 617 to phenylalanine mutation of human JAK2. In some embodiments, the package insert or the label indicates that the compound can be used for treating myelofibrosis in a subject, and that subject should discontinue the treatment upon indication of elevated levels of one or more of amylase, lipase, aspartate aminotransferase (AST), alanine aminotransferase (ALT), creatinine, and/or alkaline phosphatase and/or decreased level of calcium in the serum of the subject, and/or upon indication of one or more of anemia, thrombocytopenia, and/or neutropenia. In some embodiments, the package insert or the label further indicates that the compound can be discontinued without prior dose reduction.

In some embodiments, there is provided a kit or article of manufacture comprising (a) an admixture of (i) a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, (ii) excipient (e.g., microcrystalline cellulose such as silicified microcrystalline cellulose), and (iii) lubricant (e.g., sodium stearyl fumarate), and (b) a package insert or a label indicating that the admixture is useful for treating myelofibrosis in a subject. In some embodiments, there is provided a kit or article of manufacture comprising (a) a compound which is N-tert-butyl-3-[(5-methyl-2-{[4-(2-pyrrolidin-1-ylethoxy)phenyl]amino}pyrimidin-4-yl)amino]benzenesulfonamide or a pharmaceutical salt thereof or a hydrate thereof, and (b) a package insert or a label indicating that the compound can be used for treating myelofibrosis in a subject, wherein the subject has previously received another myelofibrosis therapy with a JAK2 inhibitor which is not N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof.

In some embodiments, the package insert or a label indicates that, upon administration of the compound to a human subject, the Cmax of the compound is achieved within about 1 to about 5 hours, about 1.5 to about 4.5 hours, about 2 to about 4 hours, or about 2.5 to about 3.5 hours post-dose. In some embodiments, the package insert or a label indicates that, upon administration of the compound to a human subject, the elimination half life of the compound is about 12 to about 40 hours, about 16 to about 34 hours, or about 20 to about 30 hours. In some embodiments, the mean AUC of the compound increases more than proportionally with increasing doses ranging from about 30 mg to about 800 mg per day. In some embodiments, the accumulation of the compound is about 1.1 to about 5 fold, about 1.25 to about 4.0 fold, about 1.5 to about 3.5 fold, about 2 to about 3 fold at steady state when the compound is dosed once daily.

In some embodiments, the package insert or the label instructs the subject to ingest the effective amount of the compound on an empty stomach. In some embodiments, the package insert or the label instructs the subject to avoid ingesting agents that are at least moderate inducers or inhibitors of CYP3A4. In some embodiments, the inducer or inhibitor of CYP3A4 is any one of the inducers or inhibitors of CYP3A4 described herein.

Also provided are uses of a compound in the manufacture of a medicament for treating myelofibrosis in a subject, wherein the compound is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof. In some embodiments, the use is according to a method described herein. In some embodiments, the compound is in an admixture of (i) the compound, (ii) an excipient (e.g., microcrystalline cellulose such as silicified microcrystalline cellulose), and (iii) a lubricant (e.g., sodium stearyl fumarate). In some embodiments, the compound is administered orally. In some embodiments, the use is according to a method described herein. In some embodiments, there is provided use of a compound in the manufacture of a medicament for treating myelofibrosis in a subject, wherein the compound is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, wherein the subject is negative for the valine 617 to phenylalanine mutation of human Janus Kinase 2 (JAK2) or negative for the mutation corresponding to the valine 617 to phenylalanine mutation of human JAK2. In some embodiments, there is provided use of a compound in the manufacture of a medicament for treating myelofibrosis in a subject, wherein the compound is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, wherein the subject has previously received another myelofibrosis therapy. In some embodiments, the previous therapy comprises a JAK2 inhibitor which is not N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof.

Also provided is a compound for treating myelofibrosis in a subject, wherein the compound is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof. In some embodiments, the treatment is according to a method described herein. In some embodiments, the compound is in an admixture of (i) the compound, (ii) an excipient (e.g., microcrystalline cellulose such as silicified microcrystalline cellulose), and (iii) a lubricant (e.g., sodium stearyl fumarate). In some embodiments, the compound is administered orally. In some embodiments, the treatment is according to a method described herein. In some embodiments, there is provided a compound for treating myelofibrosis in a subject, wherein the compound is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, wherein the subject is negative for the valine 617 to phenylalanine mutation of human Janus Kinase 2 (JAK2) or negative for the mutation corresponding to the valine 617 to phenylalanine mutation of human JAK2. In some embodiments, there is provided a compound for treating myelofibrosis in a subject, wherein the compound is N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof, wherein the subject has previously received another myelofibrosis therapy. In some embodiments, the previous therapy comprises a JAK2 inhibitor which is not N-tert-butyl-3-[(5-methyl-2-{[4-(2-pyrrolidin-1-ylethoxy)phenyl]amino}pyrimidin-4-yl)amino]benzenesulfonamide or a pharmaceutically acceptable salt thereof or a hydrate thereof.

The following are examples of the methods and compositions provided herein. It is understood that various other embodiments may be practiced, given the general description provided above.

EXAMPLES

Example 1 Evaluation of TG101348 in Myelofibrosis

As used herein, "TG101348" refers to N-tert-butyl-3-[(5-methyl-2-{[4-(2-pyrrolidin-1-ylethoxy)phenyl]amino}pyrimidin-4-yl)amino]benzenesulfonamide dihydrochloride monohydrate. The subjects in this study were administered with capsule form of TG101348 as described in Example 5. TG101348 was evaluated in a Phase I study for the treatment of myelofibrosis. This study was ongoing at the time the data were collected.

Background:

TG101348 is a potent, orally bioavailable, JAK2-selective small molecule inhibitor, that was evaluated in a Phase I study for the treatment of myelofibrosis. The dose-limiting toxicity was asymptomatic grade 3 or 4 amylasemia/lipasemia that was reversible, and the maximum tolerated dose ("MTD") was 680 mg. The most frequent non-hematological toxicities were mild nausea, vomiting, and/or diarrhea that were easily controlled or resolved spontaneously. Grade 3/4 neutropenia and thrombocytopenia were observed in 14% and 25% of patients, respectively. TG101348 had activity in reducing spleen size, leukocyte count, and JAK2V617F ("VF") allele burden. This example describes the results with a focus on the data from the dose confirmation cohort who initiated treatment at a dose of 680 mg/day.

Results:

Fifty nine patients (median age=66 years; range 43-86) were treated—28 in the dose escalation phase, and 31 in the dose confirmation phase. Overall, 44 patients had PMF, 12 post-PV MF, and 3 post-ET MF; 86% were VF-positive. Median palpable spleen size was 18 cm and 22 patients were red blood cell ("RBC") transfusion-requiring at study enrollment. After a median follow-up of 12 weeks (range<1-76), 18 (31%) patients discontinued treatment due to toxicity (n=7; thrombocytopenia=3, neutropenia=1), comorbidities (n=5), withdrawal of consent (n=4), or non-compliance/lack of response (1 each). The remaining 41 patients were at the following dose levels when the data in this example were collected: 680 mg (n=14), 520-600 mg (n=16), 360-440 mg (n=10), and 240 mg (n=1). The cumulative drug exposure to the time when the data in this example were collected was 362 patient-months; exposure at or above MTD (≥680 mg) was 154 patient-months. Forty patients (68%) started treatment at ≥680 mg.

Toxicity:

TG101348 was well tolerated. Of the patients who started at ≥680 mg, Gr3/4 neutropenia was observed in 15/0% and Gr3/4 thrombocytopenia in 20/10%. Twenty four (60%) patients did not require RBC transfusions at baseline (median hemoglobin ("Hgb")=9.6 g/dL; range 7.4-13.1); of these, 42% and 8% of patients developed Grade 3 ("Gr3") and Grade 4 ("Gr4") anemia, respectively. The majority of patients who started at ≥680 mg developed mild nausea (1 Gr3), vomiting (1 Gr3), and/or diarrhea (3 Gr3) that were self-limited or easily controlled. Other non-hematological toxicities included Grade 1/2 ("Gr1/2") transaminitis (38%), Gr1/2 serum creatinine elevation (38%), and asymptomatic hyperlipasemia (33%).

Efficacy:

Thirty three patients who started at ≥680 mg completed at least 3 cycles of treatment; at 3 months, reduction in palpable spleen size (baseline median=18 cms; range 6-32) was at least 50% in 22 (67%) patients; the spleen became non-palpable in 9 (27%) patients. All 21 patients with leukocytosis at baseline (WBC range 11 to 203×10$^9$/L) who started at ≥680 mg experienced a marked reduction in their WBC count (range 4 to 90); 70% had a normal WBC count at their last follow-up visit. Overall, 48 of the 51 VF-positive patients completed at least 1 cycle and were evaluable for response in VF allele burden; at last available follow-up, the median decrease in granulocyte mutant allele burden was 48%; 21 (44%) patients had a ≥50% reduction, and in the group who started treatment at ≥680 mg, 48% have had a ≥50% reduction. Of those evaluable, there was clinically significant benefit or resolution of constitutional symptoms, including early satiety, fatigue, cough, pruritus, and night sweats.

Conclusions:

TG 101348 was well tolerated in patients with myelofibrosis. Spleen and leukocyte responses were frequent, observed early, and produced substantial clinical benefit for patients. These responses were associated with significant decrease in VF allele burden and pointed to activity of TG101348 against the malignant clone in myelofibrosis.

Example 2 Evaluation of TG101348 in Myelofibrosis

The subjects in this study were administered with capsule form of TG101348. TG101348 was evaluated in a Phase I study for the treatment of myelofibrosis. This study is also described in Example 1. This example describes data available at the time of data collection.

This study was an open-label, multicenter, and dose-escalation study with expanded cohort dose confirmation at MTD. The primary objective of this study was to determine safety/tolerability, DLT, MTD, and pharmacokinetics of TG101348 in subjects with MF. The secondary objective of this study was to evaluate preliminary clinical and pharmacodynamic activity.

The key eligibility criteria for subjects included: Myelofibrosis (PMF or post-PV/ET MF); High-risk or intermediate-risk with symptomatic splenomegaly/unresponsive to available therapy; ECOG performance status ≤2; ANC ≥1×10$^9$/L; Platelet count ≥50×10$^9$/L; Serum creatinine ≤2 mg/dL; Total bilirubin ≤2 mg/dL; AST/ALT ≤3× upper limit of normal.

The subject disposition for this study is included in Table 1.

TABLE 1

| Subject Disposition | | |
|---|---|---|
| | MTD* | Overall |
| Enrolled | 40 | 59 |
| Included in safety analysis | 40 | 59 |
| Included in drug activity analysis | 37 | 55 |
| Discontinued | 11 (28%) | 15 (25%) |
| Reasons for discontinuation | | |
| Adverse event | 5 | 6 |
| Subject withdrew consent | 4 | 6 |
| Investigator discretion | 2 | 3 |
| Median (range) treatment duration | 24 weeks (1-24 weeks) | 24 weeks (0.3-84 weeks)** |

*Includes all subjects who initiated treatment at 680 or 800 mg/day.
**Includes continued treatment in extension study.

The demographic and baseline characteristics for the subjects are included in Table 2.

TABLE 2

| Demographic and Baseline Characteristics | | |
|---|---|---|
| | MTD (n = 40) | Overall (N = 59) |
| Age (median; years) | 65 (43-85) | 64 (43-85) |
| Male | 22 (55%) | 34 (58%) |
| JAK-2$^{V617F}$ positive | 35 (88%) | 51 (86%) |
| PMF | 31 (78%) | 44 (75%) |
| Post-PV MF | 6 (15%) | 12 (20%) |
| Post-ET MF | 3 (8%) | 3 (5%) |
| High risk | 20 (50%) | 26 (44%) |
| Palpable splenomegaly | 39 (98%) | 58 (98%) |
| Transfusion dependent | 16 (40%) | 22 (37%) |

This study was a dose-escalation study with expanded cohort dose confirmation at MTD. Below describes the data with a focus on the dose confirmation cohort who initiated treatment at a dose of 680 mg/day.

The decrease in palpable spleen size by cycle for subjects treated with TG101348 680 mg/day (starting dose) (N=37) is shown in FIG. 1. The baseline spleen size was: median=18 cm; range=6-32 cm. 49% of subjects achieved clinical improvement based on reduction of palpable splenomegaly (IWG response) (56% of subjects by 12 weeks; 100% of subjects by 20 weeks). There was no relapse or disease progression at the time of data collection.

The effect of TG101348 on leukocytosis is shown in FIG. 2. The baseline WBC count was >11×10$^9$/L. 73% of subjects had normal WBC counts at their follow-up visit. The effect of TG101348 on thrombocytosis is shown in FIG. 3 (baseline platelet count>450×10$^9$/L). TG101348 was able to reduce platelet counts. The effects of TG101348 on constitutional symptoms (baseline versus last visit) are shown in FIG. 4. TG101348 was able to improve the MF-associated constitutional symptoms. TG101348 had no significant changes on cytokine levels (see FIG. 5, all values shown are medians). FIG. 6 shows the effect of TG101348 on V617F allele burden in subjects with baseline>20% (N=22). FIG. 6 shows that TG101348 was able to decrease JAK2 V617F allele burden in 59% of the subjects with baseline>20%.

FIG. 7 shows the effects of TG101348 on bone marrow cellularity in a 76-year-old male with V617F negative PMF. The starting dose was 30 mg/day and the dose at follow-up was 520 mg/day. FIG. 7 shows that TG101348 was able to reduce bone marrow cellularity in this subject from 60% bone marrow cellularity at baseline to 5-10% bone marrow cellularity after 18 cycles. FIG. 8 shows the effect of TG101348 on bone marrow fibrosis in a 56-year-old male with V617F negative PMF. The starting dose was 240 mg/day and the dose at follow-up was 440 mg/day. FIG. 8 shows that TG101348 was able to reduce bone marrow fibrosis in this subject from 3+ at baseline to 0 after 18 cycles.

The treatment-emergent grade 3 & 4 hematologic toxicities in MTD Subjects (N=40) is shown in Table 3. The treatment-emergent non-hematologic adverse events (reported for at least 5 subjects) in MTD Subjects (N=40) is shown in Table 4.

TABLE 3

Treatment-Emergent Grade 3 & 4 Hematologic Toxicities in MTD Subjects (N = 40)

| Neutropenia (N = 40) | | Thrombocytopenia (N = 40) | | Anemia (N = 24)* New Transfusion |
|---|---|---|---|---|
| Grade 3 | Grade 4 | Grade 3 | Grade 4 | Requirement on Study‡ |
| 6 (15%) | 0 | 8 (20%) | 5 (13%) | 16 (67%) |

*Subjects who were not transfusion dependent at baseline.
‡Transfusion on at least 2 occasions for hemoglobin ("Hb") <10 g/dL.

TABLE 4

Treatment-Emergent Non-Hematologic Adverse Events in MTD Subjects (N = 40)

| Event | Grade 1 | Grade 2 | Grade 3 | Grade 4 |
|---|---|---|---|---|
| Gastrointestinal disorders | | | | |
| Diarrhea | 21 (53%) | 4 (10%) | 5 (13%) | 0 |
| Nausea | 20 (50%) | 6 (15%) | 2 (5%) | 0 |
| Vomiting | 20 (50%) | 7 (18%) | 1 (3%) | 0 |
| Constipation | 6 (15%) | 1 (3%) | 0 | 0 |
| Abdominal pain | 5 (13%) | 0 | 0 | 0 |
| Other | | | | |
| Anorexia | 7 (18%) | 0 | 1 (3%) | 0 |
| Edema peripheral | 7 (18%) | 1 (3%) | 0 | 0 |
| Fatigue | 2 (5%) | 3 (8%) | 1 (3%) | 0 |
| Contusion | 5 (13%) | 0 | 0 | 0 |
| Headache | 4 (10%) | 1 (3%) | 0 | 0 |
| Proteinuria | 2 (5%) | 3 (8%) | 0 | 0 |

The grade ≥2 treatment-emergent non-hematologic laboratory findings in MTD subjects (N=40) is shown in Table 5.

TABLE 5

Grade ≥2 Treatment-Emergent Non-Hematologic Laboratory Findings in MTD Subjects (N = 40)

| Finding | Grade 2 | Grade 3 | Grade 4 |
|---|---|---|---|
| Creatinine increased | 11 (28%) | 0 | 0 |
| Hypocalcemia | 8 (20%) | 3 (8%) | 0 |
| AST increased | 5 (13%) | 1 (3%) | 0 |
| ALT increased | 8 (20%) | 2 (5%) | 0 |
| Hyperkalemia | 3 (8%) | 2 (5%) | 1 (3%) |
| Hyperlipasemia | 4 (10%) | 3 (8%) | 2 (5%) |
| Hyperamylasemia | 0 | 1 (3%) | 1 (3%) |

Laboratory findings were transient and reversible, and resolved spontaneously or following dose interruption and/or reduction.

FIG. 9 shows various measurements in a subject with JAK2V617F-positive PMF that started at TG101348 680 mg/day. TG101348 was able to reduce the palpable spleen size from 9 cm to 0 cm and led to complete resolution of pruritus in this subject.

Conclusions:

TG101348 was generally well tolerated, with manageable, grade 1 gastrointestinal effects, especially at higher doses. The data indicated no long-term toxicities. The expected on-target myelosuppressive effect appeared to be mostly limited to erythropoiesis, which may be attenuated at lower, but still effective, doses. TG101348 had remarkable activity in MF-associated splenomegaly: ~two-thirds achieved ≥50% reduction in palpable splenomegaly; ~30% had complete response. TG101348 had significant anti-myeloproliferation activity with virtually all treated subjects experiencing complete resolution of leukocytosis and thrombocytosis. TG101348 had remarkable activity against MF-associated constitutional symptoms, pruritus and cachexia. TG101348 induced a significant decrease in JAK2V617F allele burden in a substantial proportion of treated subjects. TG101348 had minimal effect on serum levels of proinflammatory cytokines; this was consistent with the absence of immediate adverse cytokine-rebound phenomenon upon study drug discontinuation. Without wishing to be bound by any theory, the activity of TG101348 appeared to be a direct consequence of its JAK2 inhibitory activity and not an indirect effect from non-specific anti-cytokine activity. Furthermore, the preliminary observations showed reduction in BM cellularity and reticulinfibrosis with extended treatment.

Example 3 Evaluation of TG101348 in Myelofibrosis

The subjects in this study were administered with capsule form of TG101348.

Study Design:

The study constituted a Phase 1, dose-escalation trial (MF-TG101348-001). This study is also described in Examples 1 and 2. Study eligible patients were ≥18 years of age with high- or intermediate-risk primary myelofibrosis (PMF), post-PV MF, or post-ET MF (Tefferi A et al., Leukemia 22:14-22, 2008). Additional eligibility criteria and participating centers are listed in Table 6. All patients provided written informed consent. The primary endpoints were determination of safety and tolerability, dose-limiting toxicity ("DLT"), maximum tolerated dose ("MTD") and pharmacokinetic ("PK") behavior of TG101348. The secondary endpoint was assessment of therapeutic activity.

TABLE 6

Detailed enrollment criteria for MF-TG101348-001

| Inclusion Criteria | Exclusion Criteria |
|---|---|
| 1. Diagnosis of MF (PMF, post-PV MF, or post-ET MF) according to the revised WHO criteria.* | 1. Any chemotherapy, immunomodulatory drug therapy, immunosuppressive therapy, corticosteroids >10 mg/day prednisone or equivalent, or growth factor treatment within 14 days (28 days in the case of darbepoetin) prior to initiation of TG101348. |
| 2. High-risk MF (defined by Mayo PSS), or Mayo PSS intermediate-risk MF** accompanied by symptomatic splenomegaly and/or unresponsive to available therapy. | 2. Major surgery or radiation therapy within 28 days prior to initiation of TG101348. |
| 3. At least 18 years of age. | 3. Concomitant treatment with agents known to inhibit or induce CYP3A4, unless approved by the sponsor. |
| 4. Body weight ≥50 kg. | 4. Known hypersensitivity to any ingredients in the study drug formulation. |
| 5. ECOG performance status ≤2. | 5. Active infection requiring antibiotics. |
| 6. Within 4 days prior to initiation of TG101348: ANC ≥1 × 10$^9$/L Platelet count ≥50 × 10$^9$/L Serum creatinine ≤2.0 mg/dL Total bilirubin ≤2.0 mg/dL AST or ALT ≤3 times the ULN (unless clinically compatible with hepatic EMH) | 6. Uncontrolled CHF (NYHA Classification 3 or 4), angina, MI, CVA, coronary/peripheral artery bypass graft surgery, TIA, or pulmonary embolism within 3 months prior to initiation of study drug. |
| 7. Life expectancy ≥12 weeks. | 7. Cardiac dysrhythmias requiring ongoing treatment, bundle branch block on ECG or QRS duration >120 ms, or prolongation of the QTc (Fridericia) interval to >450 ms for males or >470 ms for females. |
| 8. Negative serum pregnancy test result for women of childbearing potential. | 8. Pregnant or lactating females. |
| 9. Absence of active malignancy other than MF, with the exception of adequately treated basal cell carcinoma and squamous cell carcinoma of the skin. | 9. Women of childbearing potential, unless surgically sterile for at least 3 months (i.e., hysterectomy), postmenopausal for at least 12 months (FSH >30 U/mL), unless they agree to use effective, dual contraceptive methods (i.e., oral, injectable, or barrier method with male partner using a condom) while on study drug. |
| 10. Provide written informed consent to participate. | 10. Men who partner with a woman of childbearing potential, unless they agree to use effective, dual contraceptive methods (i.e., a condom, with female partner using oral, injectable, or barrier method) while on study drug. |
| 11. Willing to comply with scheduled visits, treatment plans, laboratory assessments, and other study-related procedures. | 11. Known HIV- or AIDS-related illness. |
| | 12. Clinically active hepatitis B or C. |
| | 13. Any severe, acute or chronic medical, neurological, or psychiatric condition or laboratory abnormality that may increase the risk associated with study participation or study drug administration, may interfere with the informed consent process and/or with compliance with the requirements of the study, or may interfere with the interpretation of study results and, in the investigator's opinion, would make the patient inappropriate for entry into this study. |

Abbreviations: AIDS = acquired immunodeficiency syndrome; ALT = alanine aminotransferase; ANC = absolute neutrophil count; AST = aspartate aminotransferase; CHF = congestive heart failure; CVA = cerebrovascular accident; ECG = electrocardiogram; ECOG = Eastern Cooperative Oncology Group; EMH = extramedullary hematopoiesis; FSH = follicle stimulating hormone; HIV = human immunodeficiency virus; MF = myelofibrosis; MI = myocardial infarction; NYHA = New York Heart Association; PSS = prognostic scoring system; TIA = transient ischemic attack; WBC = white blood cell.
*Tefferi and Vardiman. Leukemia. 2008 January; 22(1): 14-22
**High-risk disease requires two and intermediate-risk disease requires one of the following prognostic factors: hemoglobin <10 g/dL, WBC count <4 or >30 × 10$^9$/L, platelet count <100 × 10$^9$/L, absolute monocyte count ≥1 × 10$^9$/L.

Patients were assigned to one of 8 dose cohorts, ranging from 30 to 800 mg per day, using standard 3+3 cohort design. TG101348 was administered orally once daily, with a treatment plan for continuous daily therapy for 24 weeks (6×28-day cycles). Intra-subject dose escalation was permitted after completion of at least 3 cycles of treatment at the starting dose. Once DLT was identified, a dose-confirmation cohort initiated treatment at the MTD. Treatment beyond 6 cycles was allowed on an extension study (MF-TG101348-002; NCT00724334) if deemed beneficial to the patient and if well tolerated.

Assessment of Toxicity and Response:

Safety assessments were performed weekly during cycle 1, every other week during cycles 2 and 3, and every 4 weeks thereafter. Toxicity was graded in accordance with the National Cancer Institute Common Terminology Criteria for Adverse Events (NCI-CTCAE) version 3.0.

Responses were measured every 4 weeks per International Working Group for MPN Research and Treatment (IWG-MRT) criteria (Tefferi A et al., Blood 108:1497-1503, 2006). Assessment of bone marrow histology was performed at baseline and every 24 weeks of therapy. Changes in JAK2V617F allele burden in the granulocyte fraction of peripheral blood were measured as previously described (Kittur J et al., Cancer 109:2279-2284, 2007); the assessments were at baseline and every 4 weeks during the first 6 cycles, and every $6^{th}$ cycle of therapy in the extension study.

(Table 7). Forty-four subjects had PMF, 12 post-PV MF, and 3 post-ET MF; 86% were JAK2V617F-positive. The median duration of disease was 3.4 years (range 0.06 to 25.8). At study enrollment, the median palpable spleen size was 18 cm below the left costal margin (83% had a palpable spleen size >10 cm), median hemoglobin level was 9.2 g/dL (range 6.6 to 15.2) and 21 (36%) subjects were red cell transfusion-dependent by IWG-MRT criteria.

TABLE 7

Demographic and Baseline Subject Characteristics

| Characteristic | TG101348 Starting Dose (mg/day) | | | | | | | | MTD Cohort n = 40 | All Doses n = 59 |
| --- | --- | --- | --- | --- | --- | --- | --- | --- | --- | --- |
| | 30 n = 4 | 60 n = 3 | 120 n = 3 | 240 n = 3 | 360 n = 3 | 520 n = 3 | 680 n = 34 | 800 n = 6 | | |
| Age - years | 63.5 | 64.0 | 63.0 | 68.0 | 66.0 | 57.0 | 63.5 | 69.0 | 65.1 (10.47)† | 64.5 (9.70)† |
| Range | 55-76 | 56-66 | 53-71 | 55-79 | 61-71 | 50-66 | 43-83 | 50-85 | 43-85 | 43-85 |
| Gender | | | | | | | | | | |
| Male | 2 | 3 | 1 | 2 | 2 | 2 | 18 | 4 | 22 (55.0%) | 34 (57.6%) |
| Female | 2 | 0 | 2 | 1 | 1 | 1 | 16 | 2 | 18 (45.0%) | 25 (42.4%) |
| Race | | | | | | | | | | |
| White | 3 | 2 | 3 | 3 | 3 | 2 | 29 | 6 | 35 (87.5%) | 51 (86.4%) |
| Black, African American | 0 | 0 | 0 | 0 | 0 | 0 | 1 | 0 | 1 (2.5%) | 1 (1.7%) |
| Asian | 1 | 1 | 0 | 0 | 0 | 0 | 3 | 0 | 3 (7.5%) | 5 (8.5%) |
| Other | 0 | 0 | 0 | 0 | 0 | 1 | 1 | 0 | 1 (2.5% | 2 (3.4%) |
| Diagnosis | | | | | | | | | | |
| PMF | 3 | 2 | 1 | 3 | 2 | 2 | 27 | 4 | 31 (77.5%) | 44 (74.6%) |
| Post-PV MF | 1 | 1 | 2 | 0 | 1 | 1 | 6 | 0 | 6 (15.0%) | 12 (20.3%) |
| Post-ET MF | 0 | 0 | 0 | 0 | 0 | 0 | 1 | 2 | 3 (7.5%) | 3 (5.1%) |
| Risk Category (Mayo PSS) | | | | | | | | | | |
| High | 0 | 0 | 1 | 2 | 0 | 3 | 14 | 6 | 20 (50.0%) | 26 (44.1%) |
| Not high* | 4 | 3 | 2 | 1 | 3 | 0 | 20 | 0 | 20 (50.0%) | 33 (55.9%) |
| $JAK2^{V617F}$ Positive | 3 | 3 | 3 | 2 | 3 | 2 | 29 | 6 | 35 (87.5%) | 51 (86.4%) |
| Transfusion Dependent | 1 | 1 | 0 | 1 | 0 | 2 | 13 | 3 | 16 (40.0%) | 21 (35.6%) |
| Spleen Size >10 cm | 3 | 3 | 3 | 2 | 3 | 2 | 28 | 5 | 33 (82.5%) | 49 (83.1%) |

Abbreviations: ET, essential thrombocythemia; JAK, Janus kinase; MF, myelofibrosis; PMF, primary myelofibrosis; PV, polycythemia vera; PSS, prognostic scoring system.
*Equivalent to symptomatic/treatment refractory intermediate-risk disease.
†Mean (standard deviation)

Pharmacokinetics:
The concentration-time curves of TG101348 in plasma were evaluated by a non-compartmental analysis (with the use of WinNonlin® software, version 5.2).

Cytokine Assessment:
Samples for cytokine measurement were collected at baseline and every 4 weeks thereafter. Cytokine levels were measured using multiplexed sandwich ELISAs (Millipore, St. Charles, Mo.).

Results
Enrollment of Patients:
A total of 59 subjects were enrolled; 28 in the dose-escalation phase and 31 in the dose-confirmation phase In the dose-escalation phase, the starting dose of TG101348 was 30 mg/day and subsequent dose levels were 60, 120, 240, 360, 520, 680 and 800 mg/day (Table 7). At 800 mg/day, 2 of 6 patients experienced DLT; consequently, the MTD was declared at 680 mg/day. In the dose-confirmation phase, all patients started treatment at the MTD. The "MTD cohort" (n=40; Table 7) included patients who received 680 mg/day as their starting dose (dose-escalation cohort, n=3; dose-confirmation cohort, n=31) and those whose drug dose was decreased from 800 mg/day (n-=6) to 680 mg/day after MTD was declared.

Figure 11:
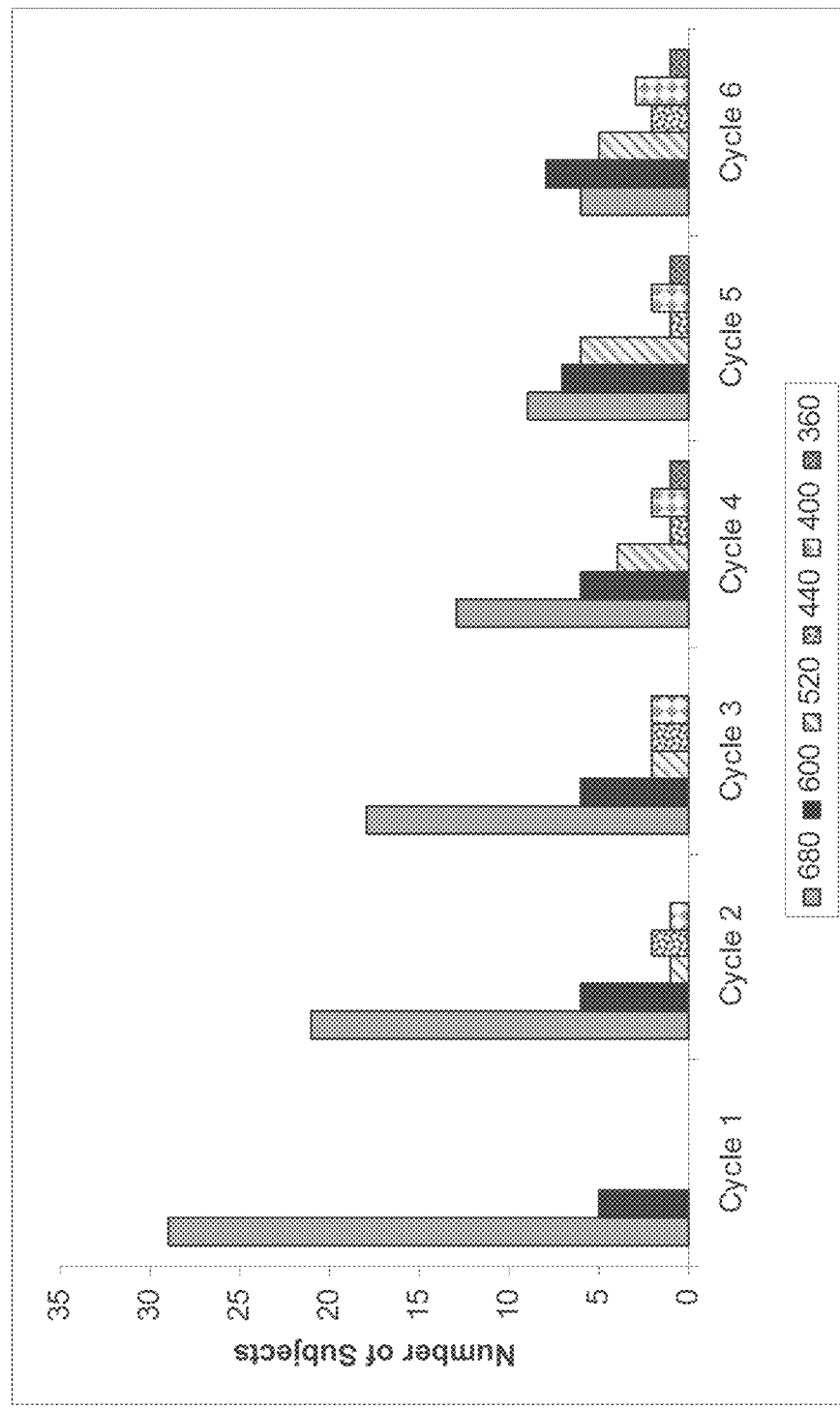
FIG. 11 shows distribution of TG101348 doses at the end of each cycle for subjects who initiated dosing at 680 mg/day (n=34).

The median (range) exposure to TG101348 for the overall (n=59) and MTD (n=40) cohorts was 155 (2-172) and 147 (8-171) days, respectively. TG101348 doses at the end of each cycle per dose cohort are illustrated in FIGS. 10 and 11. In the MTD cohort, 28 subjects (70%) required dose-reduction during the first 6 cycles; the primary reasons were: cytopenia(s) (20%), gastrointestinal adverse events (12.5%), amylase/lipase elevation (10%), ALT elevation (7.5%), investigator discretion (7.5%), or other adverse events (12.5%). The median cycle at dose-reduction for the MTD cohort was cycle 3 (range 1-7); the median (range) dose at the end of cycle 3 was 680 mg/day (360-680 mg/day); and 520 mg/day (360-680 mg/day) at the end of cycle 6.

Forty three (73%) subjects, including 28 (70%) from the MTD cohort, continued treatment on the extension study; at entry into the extension study, 31 (72%) subjects were receiving <680 mg/day of the drug (median 520 mg/day; range 120-680 mg/day). At data cutoff, the median (range) cumulative exposure to TG101348 for the 43 subjects was 380 days (170-767). The number of treatment cycles completed ranged from 7-29; 39 subjects (66%), including 27 (68%) from the MTD cohort completed 12 treatment cycles. At data cutoff, 28%, and 14% of subjects who entered the extension study had completed 18 and 24 treatment cycles, respectively. The median (range) treatment dose during the extension phase was 440 mg/day (120-680 mg/day).

Figure 12A:
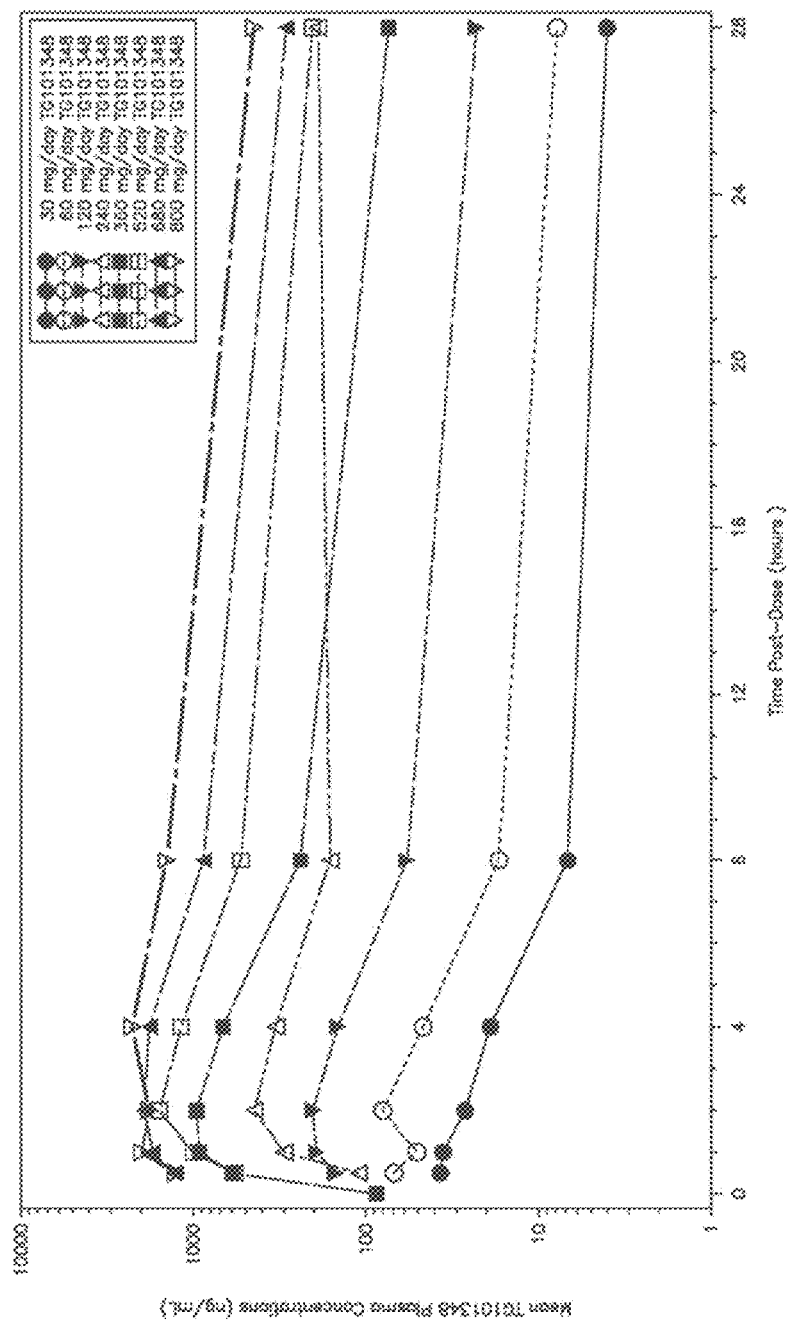
FIG. 12A shows plot of mean plasma TG101348 concentrations versus time on a semi-log scale (Cycle 1, Day 1).
Figure 12B:
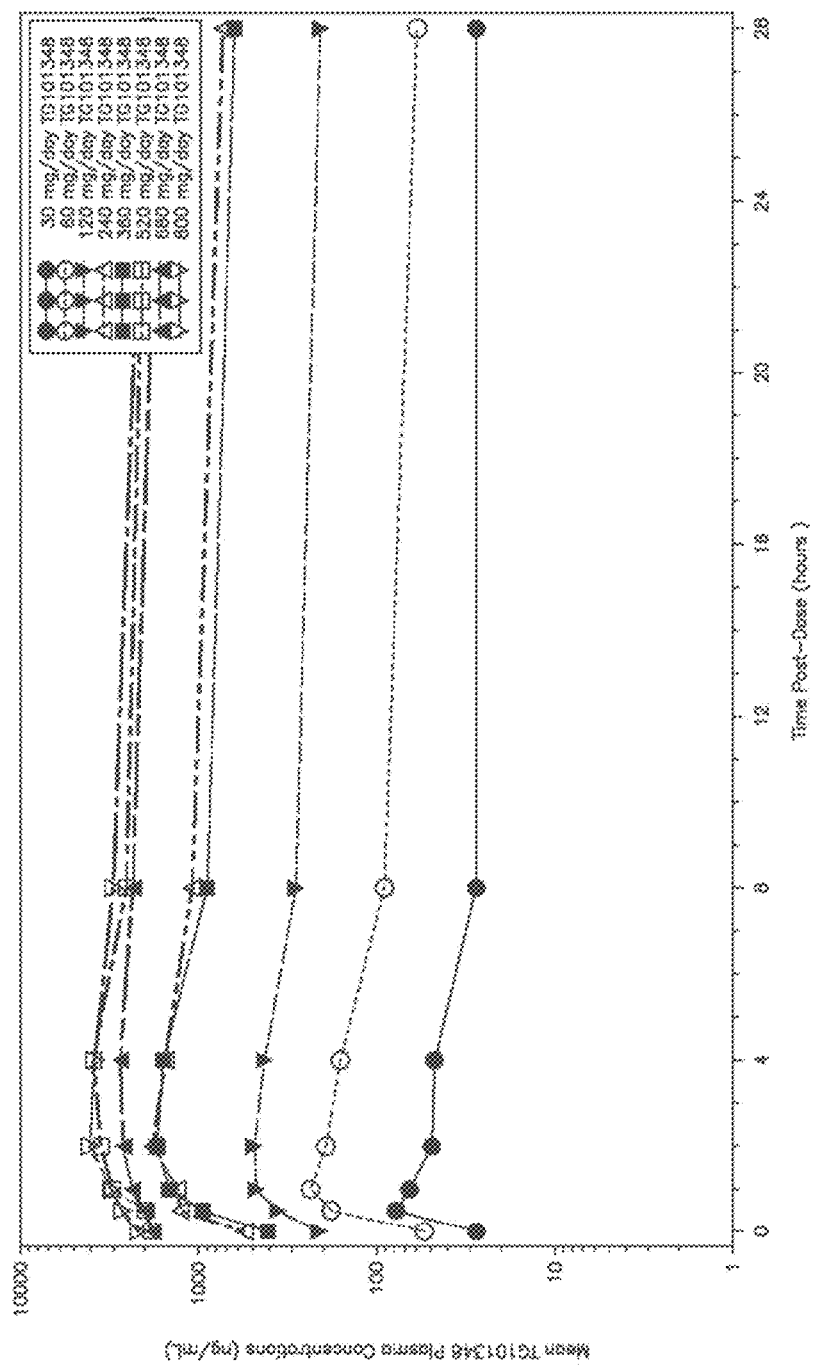
FIG. 12B shows plot of mean plasma TG101348 concentrations versus time on a semi-log scale (Cycle 1, Day 28).
Figure 18:
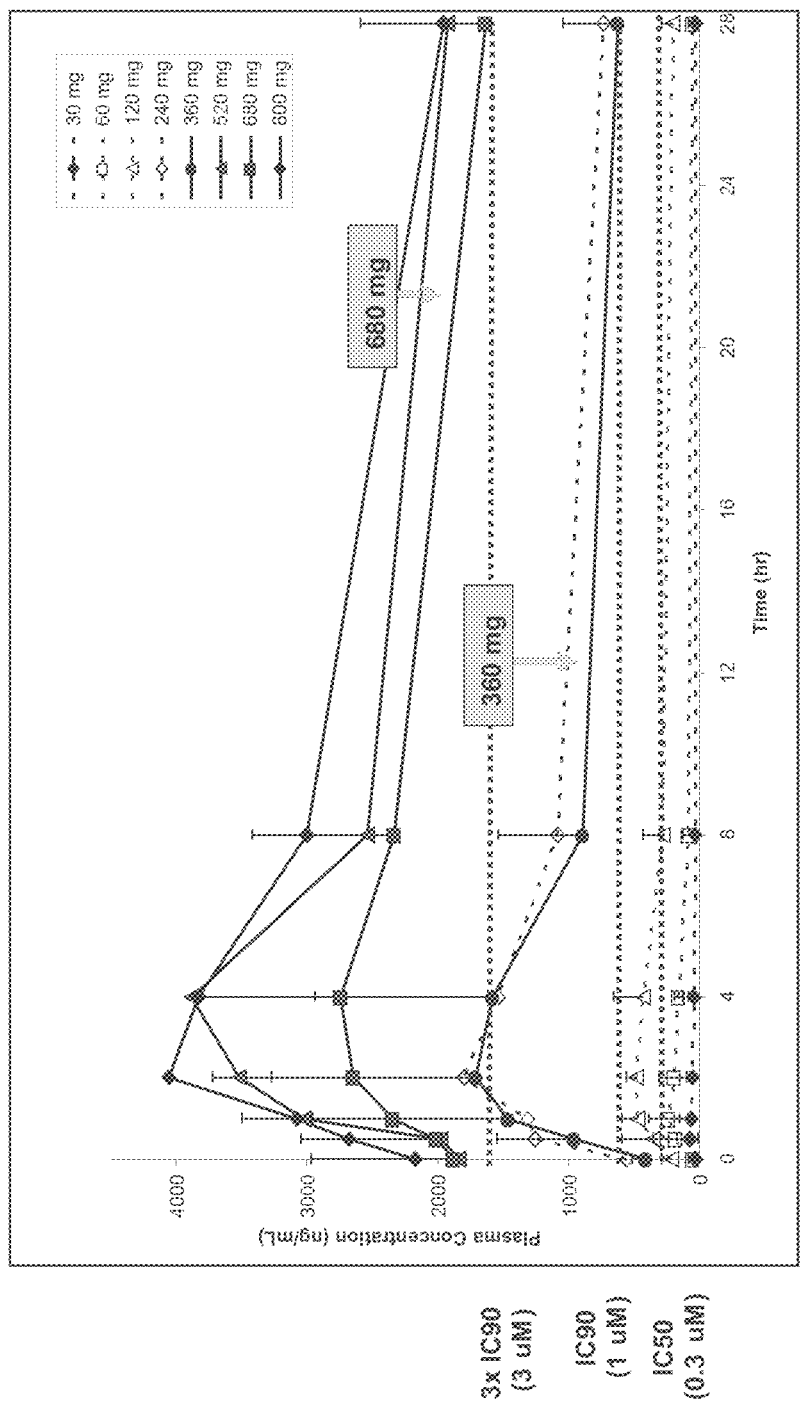
FIG. 18 shows a plot of mean plasma TG101348 concentrations versus time on a linear plot after once daily oral doses (Cycle 1; Day 28).

Pharmacokinetics:

Peak plasma concentration of TG101348 was achieved 1-4 hours after dosing. TG101348 showed greater than dose-proportional increases in plasma PK parameters ($C_{max}$ and $AUC_{0-4}$) (Table 8 and FIG. 12). Mean steady-state $C_{max}$ and $AUC_{0-t}$ values increased approximately 54- and 88-fold, respectively, over a 27-fold increase in dose. The terminal phase half-life at steady state remained similar across all doses (16 to 34 hours), consistent with linear drug elimination. FIG. 18 shows a plot of mean plasma TG101348 concentrations versus time on a linear plot after once daily oral doses (Cycle 1; Day 28). The figure shows the IC50, IC90, and 3 times IC90 (3×IC90) values for TG101348 in relation to the plasma concentration of TG101348 over time. A dose of 520 mg/day exhibited a plasma concentration TG101348 that was above 3×IC90 over the course of at least 24 hours after the dose was administered. A dose of 360 mg/day exhibited a Cmax above 3×IC90 and a plasma concentration of TG101348 that was above IC90 over the course of at least 24 hours after the dose was administered.

Safety Profile:

The DLT in 2 of 6 patients treated at 800 mg/day was asymptomatic grade 3 or 4 hyperamylasemia (with or without hyperlipasemia) that was reversible. The most common non-hematologic adverse events at least possibly related to TG101348 included predominantly grade 1 nausea, diarrhea and vomiting; grade 3 events were reported overall/in the MTD cohort for 3%/5%, 10%/13%, and 3%/3% of subjects, respectively, and there were no Grade 4 events (Table 9). These adverse events were dose-dependent, with grade 3 occurrences observed almost exclusively with a TG101348 starting dose of ≥680 mg/day. The gastrointestinal symptoms were largely self-limited or controlled by symptomatic treatment and/or dose reduction. Other adverse events (Grades 3/4; overall/MTD cohort) included asymptomatic increases in serum lipase (10%/15%), AST (2%/3%), ALT (7%/8%), creatinine (0%/0%) and alkaline phosphatase (0%/0%) (Table 9).

TABLE 9

Treatment-Emergent Non-Hematologic Adverse Events Considered at Least Possibly Related to TG101348 and Reported for ≥10% of Subjects

| Adverse Events | MTD Cohort (n = 40) | | All Subjects (n = 59) | |
|---|---|---|---|---|
| | Severity Grade 1-2 | Severity Grade 3- | Severity Grade 1- | Severity Grade 3-4 |
| Gastrointestinal disorders | | | | |
| Nausea | 31 | 2 (5.0%) | 39 | 2 (3.4%) |
| Diarrhea | 25 | 5 | 32 | 6 (10.2%) |
| Vomiting | 27 | 1 (2.5%) | 32 | 2 (3.4%) |
| Abdominal pain | 4 (10.0%) | 0 | 6 (10.2%) | 0 |
| General disorders | | | | |
| Anorexia | 6 (15.0%) | 0 | 8 (13.6%) | 0 |
| Edema peripheral | 4 (10.0%) | 0 | 6 (10.2%) | 0 |
| Abnormal laboratory values | | | | |
| Hyperlipasemia | 9 (22.5%) | 6 | 10 | 6 (10.2%) |
| Alanine aminotransferase increased | 9 (22.5%) | 3 (7.5%) | 11 | 4 (6.8%) |
| Aspartate aminotransferase increased | 13 | 1 (2.5%) | 15 | 1 (1.7%) |
| Blood creatinine increased | 11 | 0 | 14 | 0 |

TABLE 8

Mean (SD) plasma pharmacokinetic parameters following multiple daily doses of TG101348 (Cycle 1, Day 28) in MF-TG101348-001

| Parameter | Dose/Day | | | | | | | |
|---|---|---|---|---|---|---|---|---|
| | 30 mg (n = 3) | 60 mg (n = 3) | 120 mg (n = 3) | 240 mg (n = 3) | 360 mg (n = 3) | 520 mg (n = 3) | 680 mg (n = 27) | 800 mg (n = 5) |
| $C_{max}$ (ng/mL) | 81.85 (95.630) | 257.33 (121.138) | 556.67 (135.500) | 1796.67 (648.254) | 1717.33 (1558.705) | 3886.67 (3560.707) | 3064.07 (1129.671) | 4380.00 (1764.809) |
| $T_{max}$* (hr) | 2.00 (0.5, 4.0) | 1.00 (1.0, 4.0) | 2.00 (0.5, 4.0) | 2.00 (2.0, 2.1) | 2.00 (2.0, 4.0) | 4.00 (4.0, 4.0) | 4.00 (0.0, 8.3) | 2.25 (2.0, 4.0) |
| $AUC_{(0-t)}$ (hr*ng/mL) | 806.76 (806.973) | 2426.53 (1048.264) | 7645.69 (2810.740) | 26193.40 (11767.460) | 23879.05 (16898.162) | 61749.22 (57240.295) | 55111.68 (25702.038) | 70840.97 (32668.886) |
| $T_{1/2}$ (hr) | 20.94 (7.039) | 15.68 (3.464) | 24.42 (8.434) | 20.77 (6.238) | 21.39 (7.090) | 20.94 (5.006) | 33.71 (33.674) | 23.99 (9.674) |
| λz (1/hr) | 0.0354 (0.01016) | 0.0456 (0.00918) | 0.0305 (0.00932) | 0.0352 (0.00903) | 0.0353 (0.01309) | 0.0343 (0.00723) | 0.0301 (0.01421) | 0.0331 (0.01321) |

*$T_{max}$ is presented as median (min, max)

SD indicates standard deviation; $C_{max}$, peak plasma concentration; $T_{max}$, the time to the maximal concentration; $AUC_{(0-t)}$, area under the concentration-time curve from time zero to the last measurable concentration; $T_{1/2}$, terminal half-life; and λz, the elimination rate constant.

TABLE 9-continued

Treatment-Emergent Non-Hematologic Adverse Events
Considered at Least Possibly Related to TG101348
and Reported for ≥10% of Subjects

|  | MTD Cohort (n = 40) | | All Subjects (n = 59) | |
|---|---|---|---|---|
| Adverse Events | Severity Grade 1-2 | Severity Grade 3- | Severity Grade 1- | Severity Grade 3-4 |
| Blood alkaline phosphatase increased | 9 (22.5%) | 0 | 10 | 0 |
| Hypocalcemia | 6 (15.0%) | 1 (2.5%) | 7 (11.9%) | 1 (1.7%) |
| Skin and subcutaneous tissue disorders | | | | |
| Skin exfoliation | 8 (20.0%) | 0 | 8 (13.6%) | 0 |
| Dry skin | 6 (15%) | 0 | 6 (10.2%) | 0 |

Grade 3/4 hematological adverse events considered related to TG101348 included anemia (35% of 37 subjects who were not transfusion dependent at baseline), thrombocytopenia (24%) and/or neutropenia (10%) (Table 10). The majority of treatment-emergent cytopenias were noted in the first three cycles of treatment. Of the 13 subjects who developed grade 3/4 anemia (all in the MTD cohort), 67% entered the study with grade 2 anemia. Emergence of transfusion requirement was significantly lower for subjects who initiated treatment at 240-520 mg/day (33%) as opposed to 680 mg/day (72%). Of the 14 subjects with grade 3/4 thrombocytopenia, 4 and 5 subjects entered the study with grade 1 and 2 thrombocytopenia, respectively.

TABLE 10

Treatment-Emergent Hematologic Adverse Events
Considered at Least Possibly Related to TG101348
and Reported for ≥10% of Subjects

|  | MTD Cohort (n = 40) | | All Subjects (n = 59) | |
|---|---|---|---|---|
|  | Severity Grade 1-2 | Severity Grade 3-4 | Severity Grade 1-2 | Severity Grade 3-4 |
| Anemia* | 2 (8.3%) | 13 (54.2%) | 3 (8.1%) | 13 (35.1%) |
| Thrombocytopenia | 8 (20.0%) | 11 (27.5%) | 10 (17.0%) | 14 (23.7%) |
| Neutropenia | 2 (5.0%) | 4 (10.0%) | 2 (3.4%) | 6 (10.2%) |

*Events reported only for subjects who were not transfusion dependent at study entry (MTD Cohort, n = 24; All Subjects, n = 37) are presented.

At data cutoff, no unique safety findings have emerged with continued dosing of TG101348 beyond 6 cycles of therapy.

Serious adverse events considered at least possibly related to TG101348 occurred in 8 subjects and included asymptomatic hyperlipasemia, thrombocytopenia/neutropenia, depression, tumor lysis syndrome, cerebrovascular accident, and dehydration (Table 11). One subject discontinued treatment due to Grade 4 thrombocytopenia; all other events were reversible and subjects were able to resume treatment at a lower dose after resolution of the adverse event.

TABLE 11

Serious Adverse Events Assessed by Investigators as at Least Possibly Related to Therapy (MF-TG101348-001 and MF-TG101348-002)

| Subject # | Event | Starting Dose/Dose at Event (mg/day) | Onset From Start of Dosing (days) | CTCAE Severity Grade | Action Taken With Study Drug | Outcome |
|---|---|---|---|---|---|---|
| 105-013 | Thrombocytopenia | 240/360 | 215 | 4 | None | Recovered/resolved |
|  | Thrombocytopenia | 240/360 | 247 | 4 | Permanently discontinued | Not recovered/not resolved |
|  | Hyperlipasemia | 240/0 | 356 | 4 | None | Recovered/resolved |
| 104-015 | Depression | 360/520 | 256 | 3* | Permanently discontinued | Not recovered/not resolved |
| 106-024 | Nausea | 800/680 | 87 | 2 | Stopped temporarily | Recovered/resolved |
|  | Vomiting | 800/680 | 87 | 2 | Stopped temporarily | Recovered/resolved |
|  | Diarrhea | 800/680 | 87 | 3 | Stopped temporarily | Recovered/resolved |
|  | Dehydration | 800/680 | 87 | 2 | Stopped temporarily | Recovered/resolved |
|  | Tumor lysis syndrome | 800/440 | 366 | 3 | Stopped temporarily | Recovered/resolved |
|  | Dehydration | 800/400 | 474 | 3 | None | Recovered/resolved |
| 106-033 | Pleuritic pain | 680/680 | 8 | 2 | Stopped temporarily | Recovered/resolved |
| 106-045 | Dehydration | 680/440 | 170 | 3 | Stopped temporarily | Recovered/resolved |
| 101-047 | Neutropenia | 680/680 | 52 | 2 | Stopped temporarily | Recovered/resolved |
| 105-056 | Cerebrovascular accident | 680/680 | 22 | 4 | Stopped temporarily | Recovered/resolved |
|  | Gallbladder pain | 680/520 | 95 | 3 | Stopped temporarily | Recovered/resolved with sequelae |
| 105-059 | Hyperlipasemia | 680/680 | 8 | 3 | Stopped temporarily | Recovered/resolved |
|  | Hyperlipasemia | 680/520 | 28 | 3 | Stopped temporarily | Recovered/resolved |
|  | Cardiac arrest | 680/360 | 42 | 5 | Permanently discontinued | Fatal |

*Subject died (suicide) approximately 12 weeks after discontinuation of study drug.

One subject presented with severe pulmonary hypertension and right heart failure during cycle 4 (at 240 mg/day); the event was considered unrelated to TG101348 per the investigator.

Fifteen (25%) subjects discontinued treatment during the first 6 cycles of therapy (Table 12). Reasons for discontinuation included treatment-related adverse events (n=6); investigator decision/intercurrent illness (n=3) or withdrawal of consent (n=6). Eight of 43 subjects (19%) discontinued treatment during the extension study, including 3 because of adverse events following a total of 24 to 46 weeks on therapy (Table 12).

TABLE 12

Subjects discontinuing study due to death, toxicity, withdrawal of consent, or intercurrent illness MF-TG101348-001 Reasons for Discontinuation (Table 12 A)

| Subject | Starting Dose (mg/day) | Dose at Termination (mg/day) | Duration of Treatment (days) | Reason |
|---|---|---|---|---|
| 102-002 | 30 | 30 | 2 | Investigator discretion - previously undiagnosed cardiac condition with long $QT_c$ interval |
| 106-009 | 120 | 240 | 109 | Patient withdrew consent |
| 101-011 | 240 | 240 | 100 | Patient withdrew consent |
| 102-019 | 520 | 520 | 42 | Adverse event - neutropenia (grade 3; probably related) |
| 102-023 | 800 | 680 | 70 | Investigator discretion - recurrent Waldenstrom's macroglobulinemia |
| 104-027 | 800 | 680 | 77 | Adverse event - thrombocytopenia (grade 4; possibly related) |
| 106-028 | 800 | 520 | 44 | Adverse event - thrombocytopenia (grade 4; possibly related) |
| 104-029 | 680 | 680 | 44 | Adverse event - endocarditis (grade 3; not related), embolic stroke (grade 3; not related) |
| 101-032 | 680 | 680 | 8 | Investigator discretion - Acquired factor VIII inhibitor |
| 101-040 | 680 | 520 | 24 | Adverse events - diarrhea (grade 3; possibly related) |
| 103-043 | 680 | 360 | 68 | Patient withdrew consent |
| 103-046 | 680 | 680 | 26 | Patient withdrew consent |
| 102-051 | 680 | 600 | 108 | Patient withdrew consent |
| 102-054 | 680 | 680 | 75 | Patient withdrew consent |
| 105-059 | 680 | 360 | 27 | Adverse event - cardiac arrest (grade 5; possibly related) |

MF-TG101348-002 Reasons for Discontinuation (Table 12B)

| Subject | Starting Dose (mg/day) | Dose at Termination (mg/day) | Cumulative Duration of Treatment (days) | Reason |
|---|---|---|---|---|
| 101-005 | 60 | 360 | 196 | Investigator discretion - lack of response to treatment |
| 106-010 | 120 | 520 | 185 | Investigator discretion |
| 105-013 | 240 | 360 | 321 | Adverse event - thrombocytopenia (grade 4; probably related) |
| 104-015 | 360 | 520 | 257 | Adverse event - depression (grade 3; possibly related) |
| 106-016 | 360 | 680 | 527 | Investigator discretion - lack of response to treatment |
| 104-017 | 520 | 200 | 309 | Investigator discretion - disease progression |
| 105-021 | 680 | 520 | 357 | Patient withdrew consent |
| 101-047 | 680 | 320 | 233 | Adverse event - elevated creatinine (grade 2; possibly related) |

Three subjects had disease progression (doses at study start and discontinuation are indicated): one each with progressive hepatosplenomegaly and ascites with superimposed endocarditis (cycle 2; 680 and 520 mg/day), accelerated myelofibrosis (cycle 13; 520 and 200 mg/day), and leukemic transformation (cycle 2; 520 and 520 mg/day).

Responses are shown below.

Figure 13:
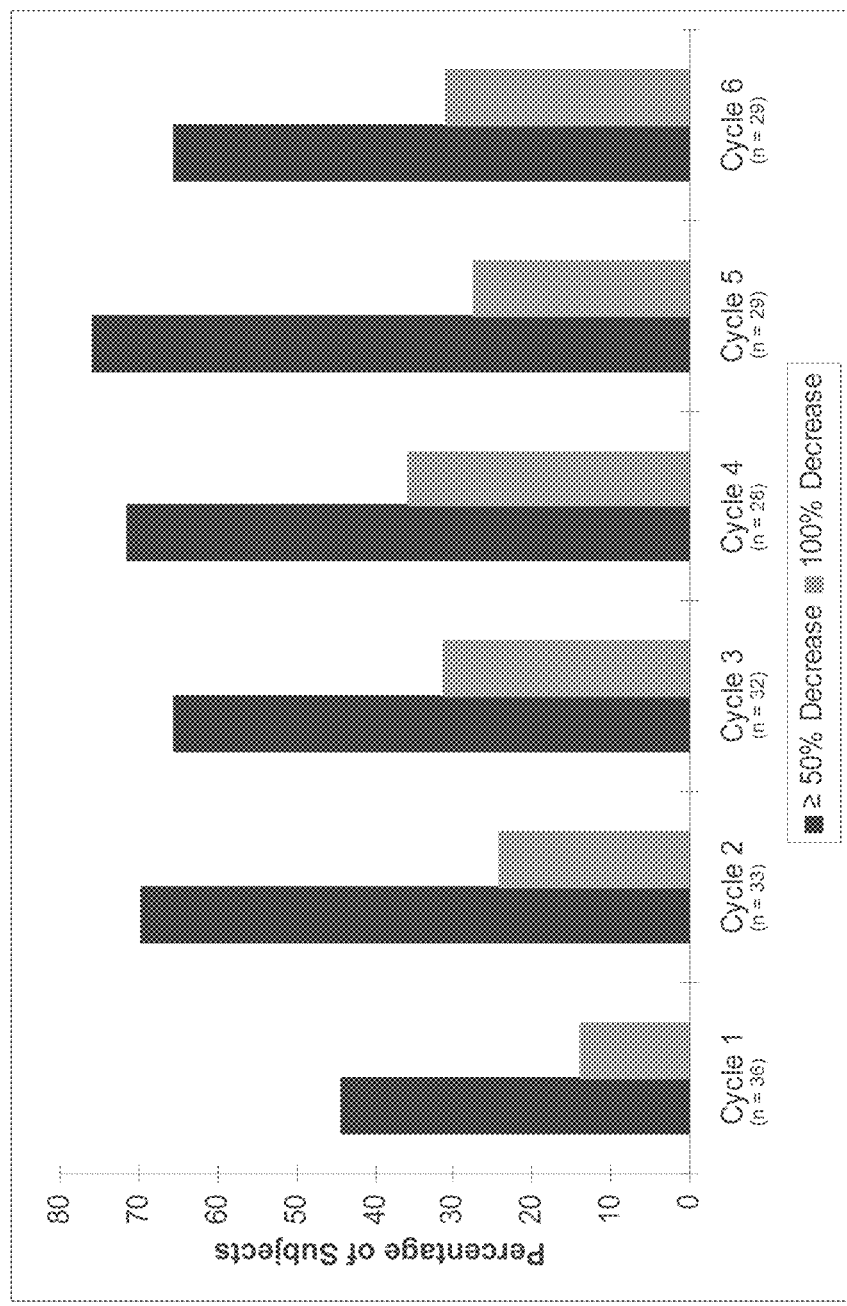
FIG. 13 shows splenomegaly response to TG101348 therapy. This figure shows decrease in palpable spleen size from baseline by cycle for subjects in the maximum tolerated dose cohort (n=37). The proportion of subjects with ≥50% and 100% decrease in palpable splenomegaly is shown. For subjects who completed 6 cycles of treatment, 90% had a ≥25% reduction in palpable spleen size, 66% had a ≥50% reduction, and in 31% the spleen became non palpable.

Splenomegaly:

The onset of spleen response was rapid, and generally seen within the first 2 cycles. By cycle 6, 36 subjects (61%) had experienced a minimum 25% decrease in palpable spleen size, including 65% in the MTD cohort (intent-to-treat analysis). By this time-point, a ≥50% decrease in palpable spleen size persistent for at least 8 weeks (i.e. Clinical Improvement ("CI") per IWG-MRT criteria) had been observed in 39% and 45% of subjects overall and in the MTD cohort, respectively. Spleen responses per treatment cycle for the MTD cohort are shown in FIG. 13. Three of 4 subjects (75%) with JAK2V617F-negative MF who completed 6 cycles of treatment achieved CI. The lowest starting dose at which CT was observed was 240 mg/day. The median time (range) to CI across doses was 141 days (41 to 171), and 113 days (41-170) for the MTD cohort. By cycle 12, spleen responses (CI) were observed in 48% and 50% of subjects, for the overall and MTD cohorts, respectively. The mean (standard deviation) duration of spleen response per IWG-MRT criteria was 315 (±129) days and 288 (±76) days for the overall and MTD cohorts, respectively.

Constitutional Symptoms:

Thirty five subjects in the MTD cohort endorsed the presence and severity of early satiety, fatigue, night sweats, cough, and pruritus on an 11-point scale (0=absence of symptoms to 10=worst imaginable symptoms) at baseline and at the end of at least one cycle. Symptoms were categorized as "absent" (score=0), "mild" (score=1-3), "moderate" (score=4-7), or "severe" (score=8-10).

Figure 14A:
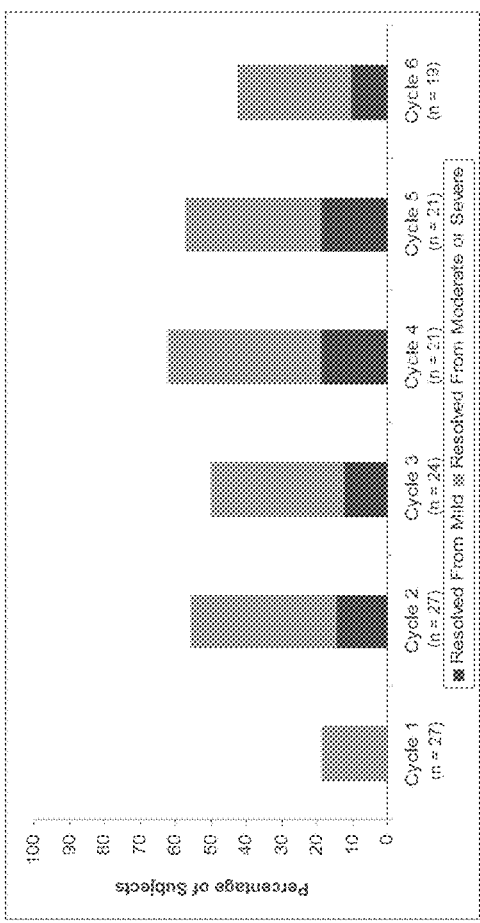
Figure 14B:
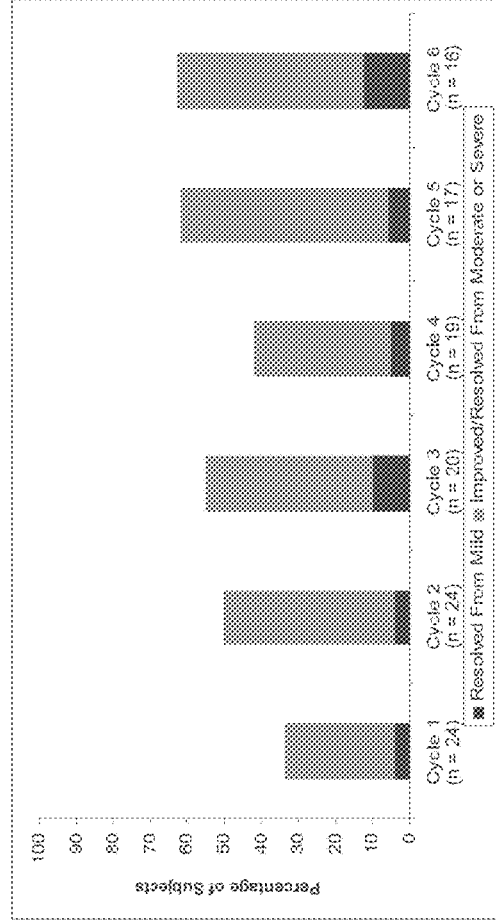

Early satiety was reported by 29 (85%) subjects at baseline. After 2 cycles of treatment (n=27), 56% reported complete resolution of this symptom (FIG. 14A). Fatigue was reported at baseline by 26 (76%) subjects. After 6 cycles (n=16), 63% reported improvement and 25% complete resolution of this symptom (FIG. 14B). Night sweats were reported at baseline by 14 (40%) subjects. After 1 cycle, 64% of subjects had complete resolution of this symptom; after 6 cycles, this proportion had increased to 89% (n=9) (FIG. 14C). Cough was reported at baseline by 13 (37%) subjects. After 1 cycle (n=12), 75% reported improvement and 67% complete resolution of this symptom. Pruritus was reported by 8 (23%) subjects at baseline. After 1 cycle, 75% had improvement, with 50% reporting complete resolution. Responses in constitutional symptoms were durable in most instances.

Body Weight:

At the end of 6 and 12 cycles, the median body weight was stable relative to baseline for the overall and MTD cohorts (Table 13).

normal platelet count; following 12 cycles, 7 of 8 subjects (88%) across doses and all 6 subjects in the MTD cohort had a normal platelet count.

Figures 16A, 16B:
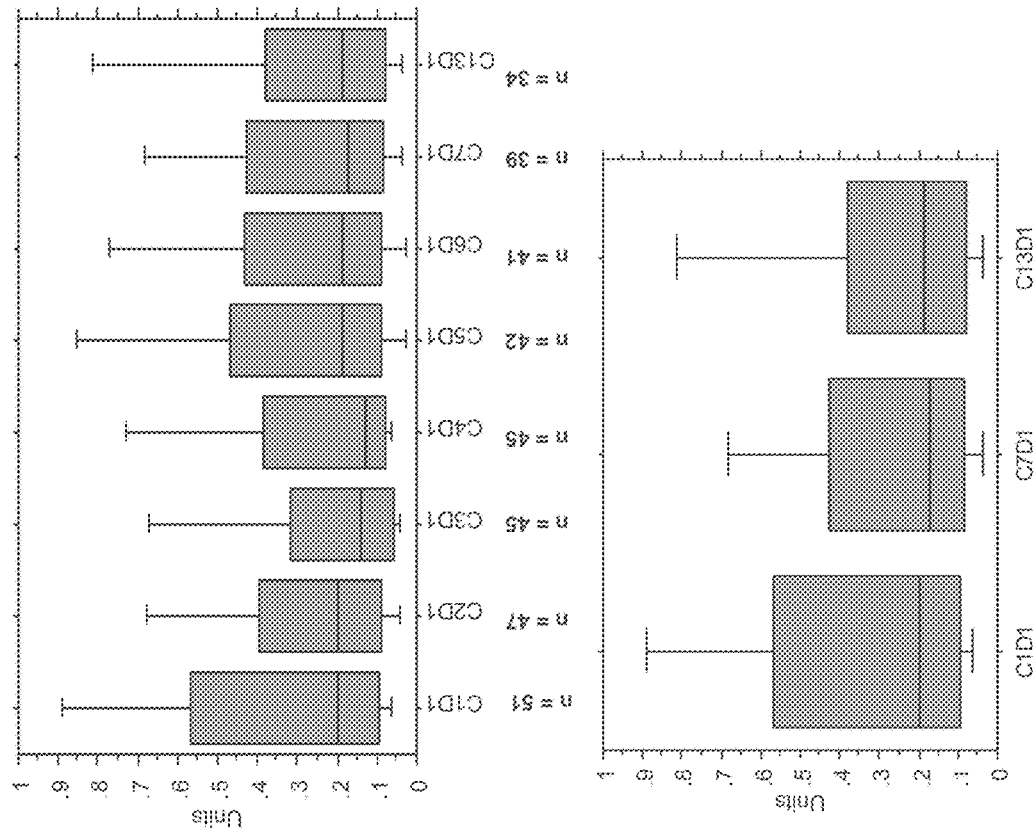
FIGS. 16A-16D show effect of TG101348 therapy on JAK2V617F allele burden. Box plot representation of JAK2V617F allele burden data for all mutation-positive subjects (n=51; figures A and B) and for the subgroup with baseline allele burden>20% (n=23.
Figure 16C:
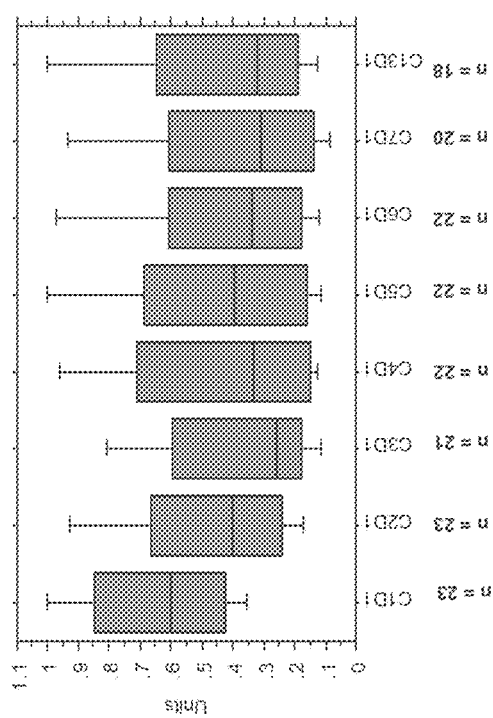
Figure 16D:
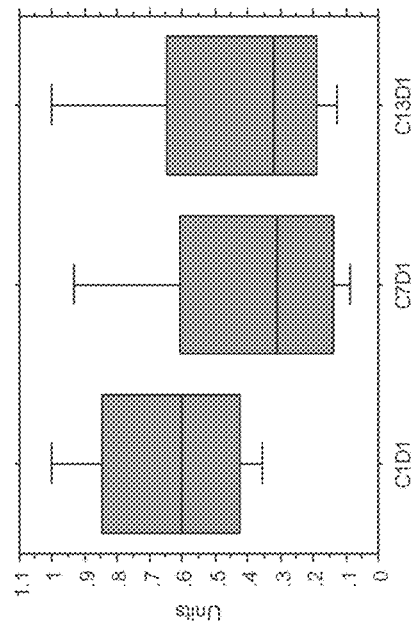
Figure 17A:
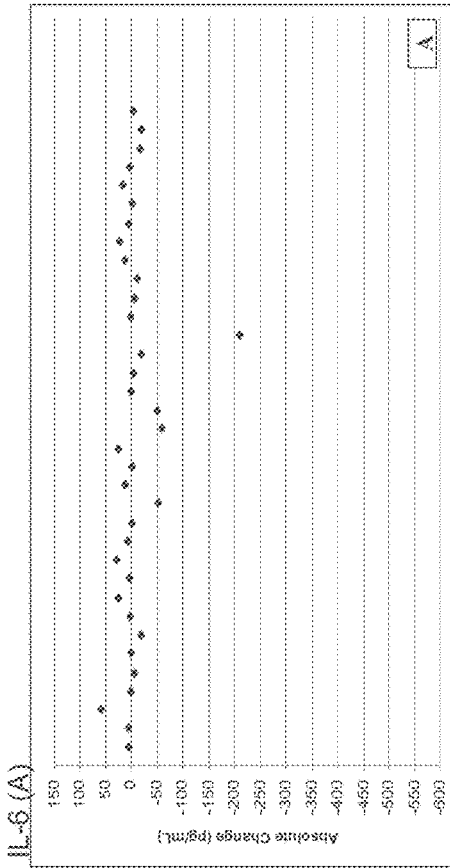
FIG. 17 shows absolute changes in pro-inflammatory cytokine levels from baseline at cycle 6: IL-6 (A), TNF-α (B), IL-8 (C), and IL-2 (D). Absolute differences in IL-6 (−4719 pg/mL) and IL-2 (−1827 pg/mL) are omitted from FIGS. 17A and 17D, respectively, for 1 subject (101-039) because they skewed presentation of data for other subjects.
Figure 17B:
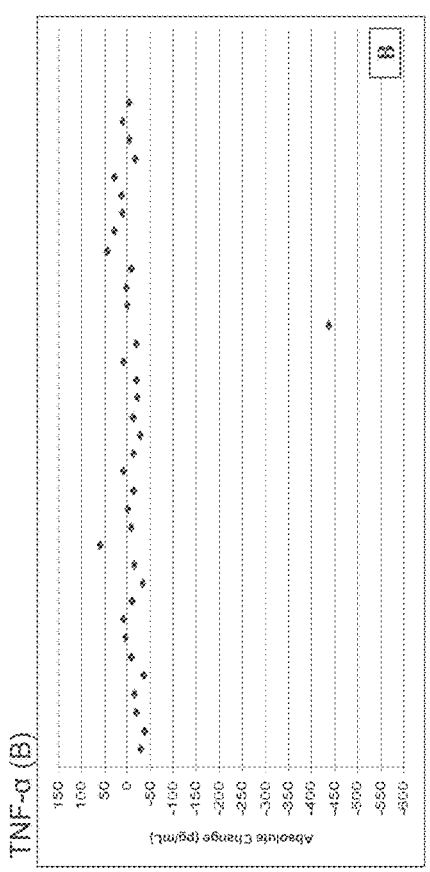
Figure 17C:
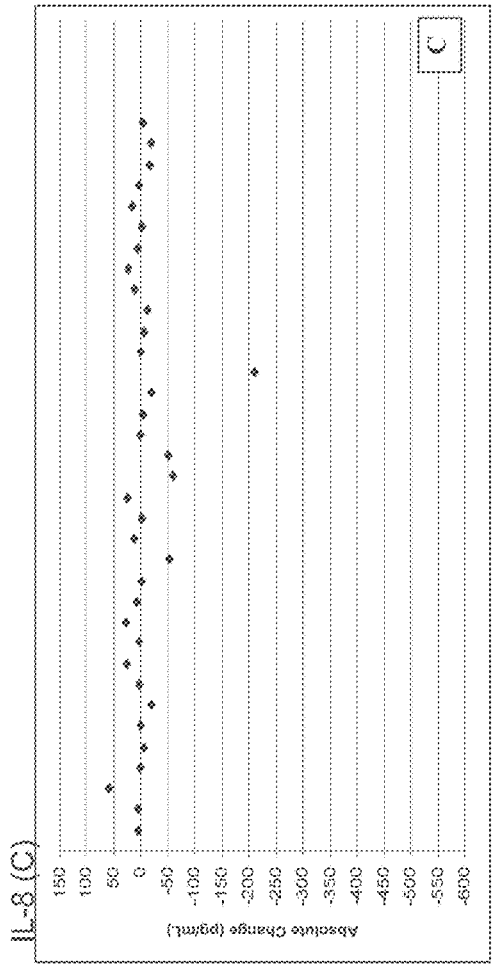
Figure 17D:
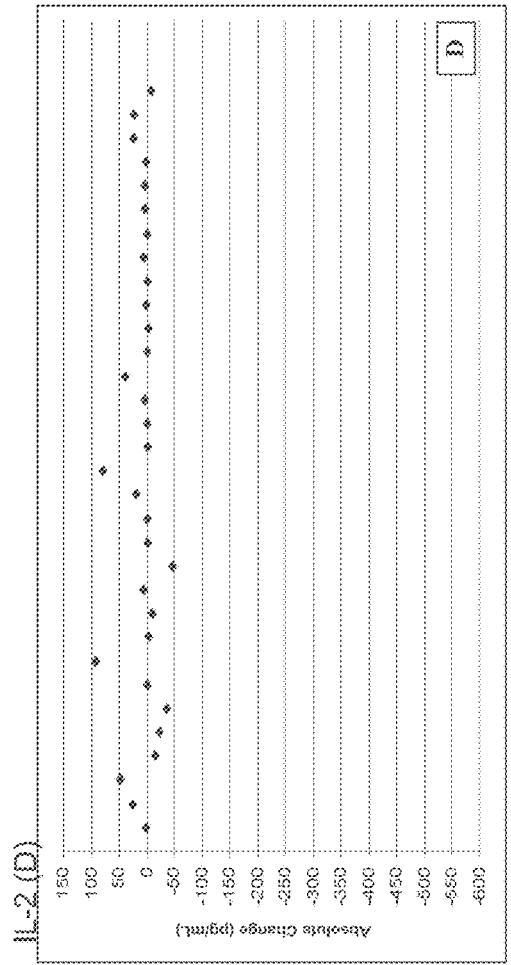

JAK2V617F Allele Burden:

Fifty-one subjects (86%) were JAK2V617F-positive, with a median (range) allele burden of 20% (3%-100%); of these, 23 (45%) had a "significant" allele burden (defined as ≥20% at baseline) with a median (range) of 60% (23%-100%). For the overall mutation-positive subjects, there was a significant decrease in the JAK2V617F allele burden after 6 cycles (p=0.04) and 12 cycles of treatment (p=0.01) (FIGS. 16A and 16B). After 6 and 12 cycles of treatment, the median (range) allele burden was 17% (0%-100%) and 19% (0%-100%), respectively. Similarly, for the 23 subjects with baseline JAK2V617F allele burden of ≥20%, there was a significant and even more pronounced decrease in the JAK2V617F allele burden after 6 cycles (p=0.00$^2$) and 12 cycles of treatment (p=0.002) (FIGS. 16C and 16D). After 6 and 12 cycles of treatment, the median (range) allele burden was 31% (4%-100%) and 32% (7%-100%), respectively. After 6 cycles, 16 of 20 subjects (80%) with baseline allele burden>20% who reached this time-point exhibited a median 61% (range 6% to 96%) decrease, and 9 subjects (45%) had a ≥50% decrease in JAK2V617F allele burden. In contrast, 4 subjects (20%) exhibited an increase (18%, 21%, 30%, and 58%). Eighteen subjects (78%) of the group with allele burden ≥20% completed 12 cycles of treatment with a median 50% (range 29% to 82%) decrease, and 7 (39%) subjects had a ≥50% decrease in JAK2V617F. Three (17%) subjects exhibited an increase in allele burden (7%, 18%, and 22%), and 2 others with 100% allele burden at baseline exhibited no change.

TABLE 13

Change in weight during study treatment

| | Weight (kg) | | | | | |
|---|---|---|---|---|---|---|
| | Baseline | | 6 Cycles | | 12 Cycles | |
| | Overall (n = 57) | MTD Cohort (n = 38) | Overall (n = 43) | MTD Cohort (n = 28) | Overall (n = 36) | MTD Cohort (n = 26) |
| Median (range) | 75.6 (48.2-105.2) | 77.7 (48.2-96.1) | 76.9 (51.4-105.8) | 77.7 (51.4-97.6) | 76.1 (49.8-106.8) | 76.5 (49.8-99.5) |
| Change from baseline Median (range) | n/a | n/a | 0.4 (−11.7-8.9) | 0.6 (−9.2-8.9) | 0.7 (−10.7-13.7) | 0.35 (−10.7-13.7) | kg indicates kilograms; n, number, and MTD, maximum tolerated dose

Figure 15:
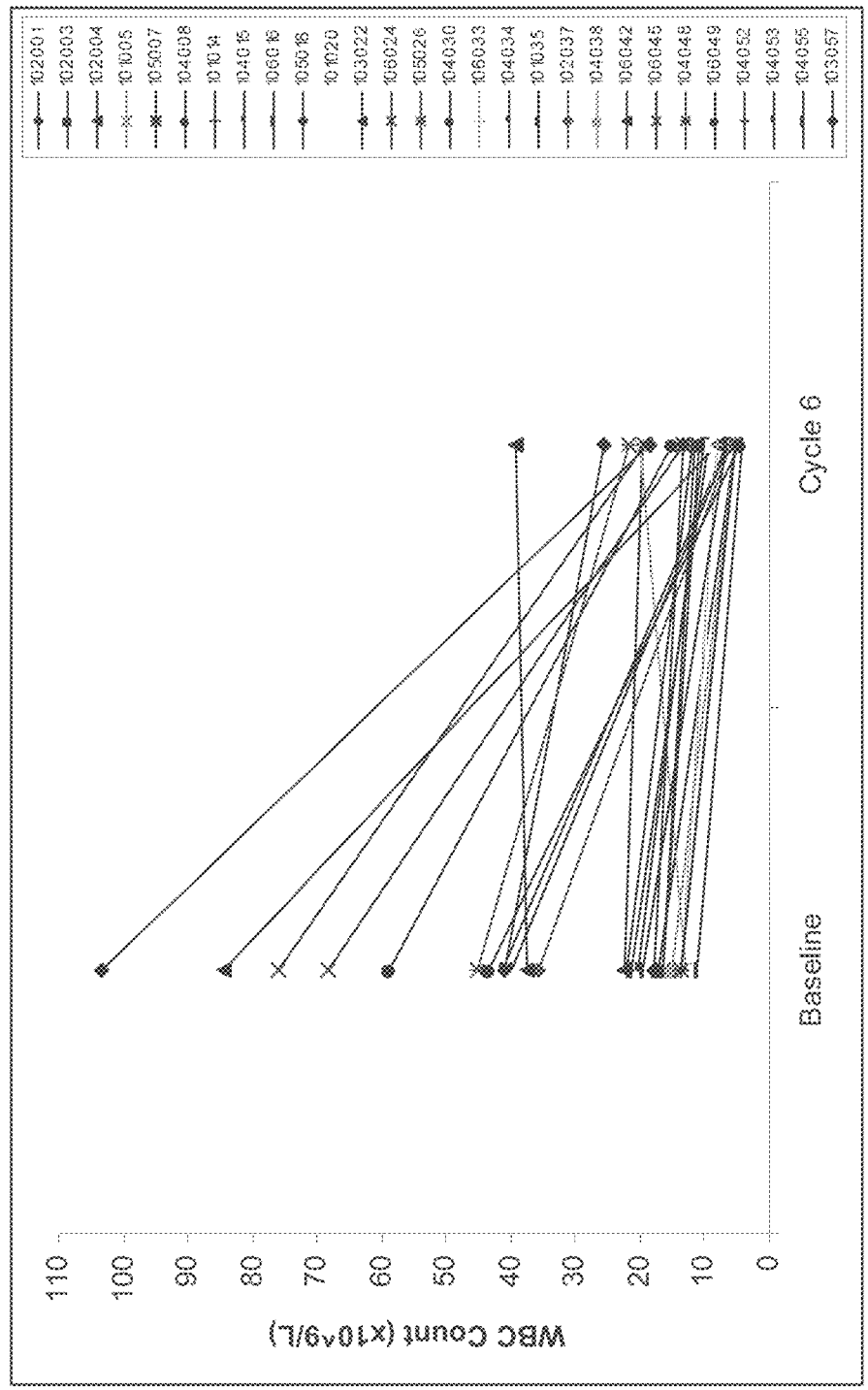
FIG. 15 shows response of leukocytosis to TG101348 therapy. Changes in white blood cell (WBC) count after 6 cycles for subjects who entered the study with leukocytosis (WBC count>11×10$^9$/L). Following 6 cycles, 16 subjects across doses (57%) and 13 subjects in the MTD cohort (72%) achieved a normal WBC count, with durable benefit.

Leukocytosis and Thrombocytosis:

Leukocytosis (WBC count>11×10$^9$/L) was present at baseline in 33 subjects (56%), 28 of whom completed 6 cycles of treatment; of these, 18 were in the MTD cohort. Following 6 cycles, 16 subjects across doses (57%) and 13 subjects in the MTD cohort (72%) achieved a normal WBC count (FIG. 15); following 12 cycles, 14 of 25 (56%) across doses and 10 of 17 (59%) in the MTD cohort had normal WBC counts.

Thrombocytosis (platelet count>450×10$^9$/L) was noted at baseline for 10 (17%) subjects across doses and 7 (19%) in the MTD cohort (n=37), all of whom completed 6 cycles of therapy. At this time point, 90% and 100% of subjects across doses and in the MTD cohort, respectively, achieved a Discussion:

A significant proportion of patients treated in this study experienced rapid, substantial, and durable control of symptomatic splenomegaly, leukocytosis, thrombocytosis, and constitutional symptoms. In addition, there was also evidence for a significant reduction in genomic disease burden that indicates potential for disease modifying activity. There were responses in MF patients who were JAK2V617F negative. It is unknown whether the subjects in this study have other mutations in the JAK-STAT signal transduction pathway such as MPL, LNK or as yet unknown alleles (Pardanani A D et al., Blood 108:3472-3476, 2006; Oh S T et al., Blood First Edition Paper, prepublished online Apr. 19, 2010; DOI 101182/blood-2010-02-270108 2010; Pardanani A et al., Leukemia In press: 2010).

The clinical study results show that TG101348 therapy can be discontinued without prior dose reduction or tapering. Subjects that were discontinued (whether or not recontinued at a later date) did not experience "cytokine rebound". This indicates that the treatment may be discontinued without prior dose reduction.

Cytokine rebound in the context of myelofibrosis is a phenomenon that has occurred in patients receiving therapy other than TG101348 therapy and were discontinued for any reason. In some cases, the discontinued patients experienced severe symptoms including acute spleen size enlargement and relapse of constitutional symptoms. In some cases, the discontinued patients experienced life-threatening hemodynamic disturbances (Wadleigh and Tefferi, Clinical Advances in Hematology & Oncology, 8:557-563, 2010).

Of note, among small molecule inhibitors of the JAK-STAT pathway in MF, TG101348 appeared to be unique in its ability to induce a significant and sustained decrease in JAK2V617F mutant allele burden. Without wishing to be bound by any theory, it appeared that the effect of JAK2 inhibition on disease burden was the basis for evidence of clinical efficacy in myelofibrosis with TG101348, as opposed to an indirect anti-cytokine effect that may play a major role in responses to JAK family antagonists that have off-target activity for JAK1 as well as for JAK2. In support of this, there were no consistent changes in levels of pro-inflammatory cytokines (interleukin ("IL")-6, IL-2, IL-8, and TNF-α) relative to baseline during the course of TG101348 treatment (FIG. 17). In contrast, and consistent with the on-target activity of TG101348 for JAK2, increases in serum EPO and to a lesser extent TPO levels relative to baseline were observed after treatment initiation (data not shown).

The DLT (asymptomatic hypercramylasemia, sometimes with hyperlipasemia) for TG101348 was observed with other small molecule inhibitors including nilotinib (Kantarjian H M et al., Blood 110:3540-3546, 2007). Gastrointestinal adverse events were frequent in this study but accounted for treatment discontinuation in only one subject. These symptoms occurred as early as after the first administered dose, and demonstrated a clear dose-dependent relationship. The myelosuppressive effects of TG101348 were also dose-dependent.

While the MTD (680 mg/day) of TG101348 was the most efficacious dose, it was also associated with the highest incidence of adverse events. Therefore, a lower starting dose (e.g. 400-500 mg/day) may provide an optimal risk/benefit balance. Furthermore, because myelofibrosis is a heterogeneous disease, a dynamic dosing schedule may maximize the opportunity for identifying a patient-specific optimal dose.

These observations suggest that, in addition to MF, TG101348 may also have a potential role for the treatment of PV and ET.

Example 4 Synthesis of TG101348

Example 4.1 N-tert-Butyl-3-(2-chloro-5-methyl-pyrimidin-4-ylamino)-benzenesulfonamide (Intermediate)

Example 4.1(a)

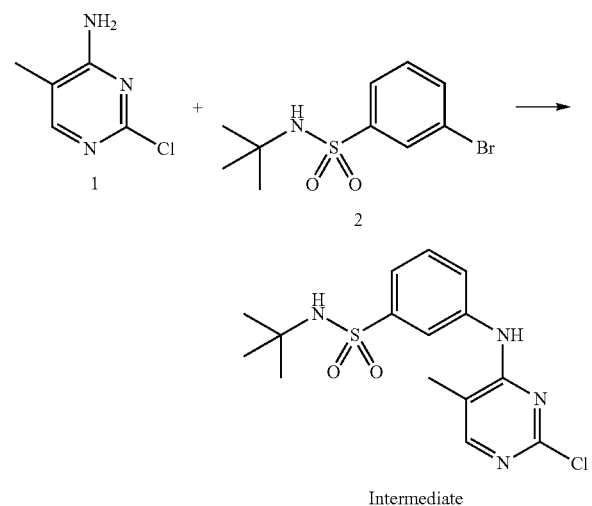

A mixture of 2-chloro-5-methyl-pyrimidin-4-ylamine (1) (0.4 g, 2.8 mmol), 3-bromo-N-tert-butyl-benzenesulfonamide (2) (1.0 g, 3.4 mmol), $Pd_2(dba)_3$ (0.17 g, 0.19 mmol), Xantphos (0.2 g, 3.5 mmol) and cesium carbonate (2.0 g, 6.1 mmol) was suspended in dioxane (25 mL) and heated at reflux under the argon atmosphere for 3 h. The reaction mixture was cooled to room temperature and diluted with DCM (30 mL). The mixture was filtered and the filtrate concentrated in vacuo. The residue was dissolved in EtOAc and hexanes added until solid precipitated. After filtration, the title compound (1.2 g, 98%) was obtained as a light brown solid. It was used in the next step without purification. MS (ES+): m/z 355 (M+H)$^+$.

Example 4.1(b)

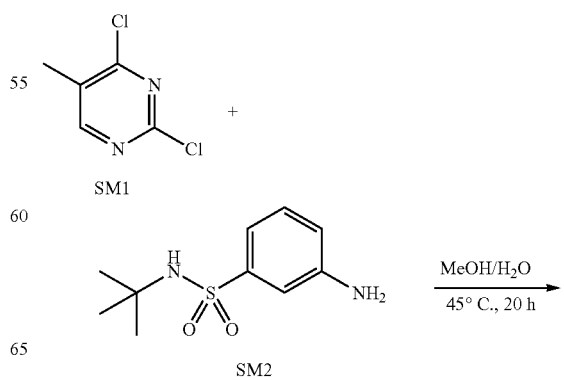

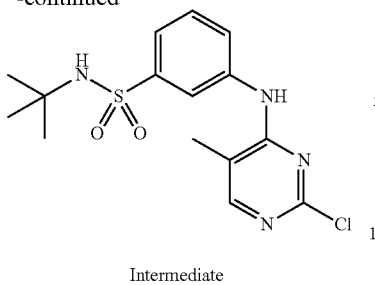

Intermediate

The Intermediate was synthesized from 2,4-dichloro-5-methylpyrimidine (SM1) and N-t-butyl-3-aminobenzenesulfonamide (SM2) in the following steps: (1) Mix MeOH (6.7 UOa) and SM1 (Combi Blocks) (UOa); (2) Add SM2 (1.15 UOa, 082 eq) and H2O (8.5 UOa); (3) Heat 45° C., 20 h, N$_2$, IPC CPL SM2<2%; (4) Cool 20° C.; (5) Centrifuge, N$_2$; (6) Wash H$_2$O (2.1 UOa)+MeOH (1.7 UOa); (7) Mix solid in H$_2$O (4.3 UOa)+MeOH (3.4 UOa); (8) Centrifuge, N$_2$; (9) Wash H$_2$O (2.1 UOa)+MeOH (1.7 UOa); and (10) Dry 45° C., vacuum, 15 h. Obtained Intermediate, mass 49.6 kg (UOb); Yield 79%; OP: 99.6%.

Example 4.2 N-tert-Butyl-3-[(5-methyl-2-{[4-(2-pyrrolidin-1-ylethoxy)phenyl]amino}pyrimidin-4-yl)amino]benzenesulfonamide

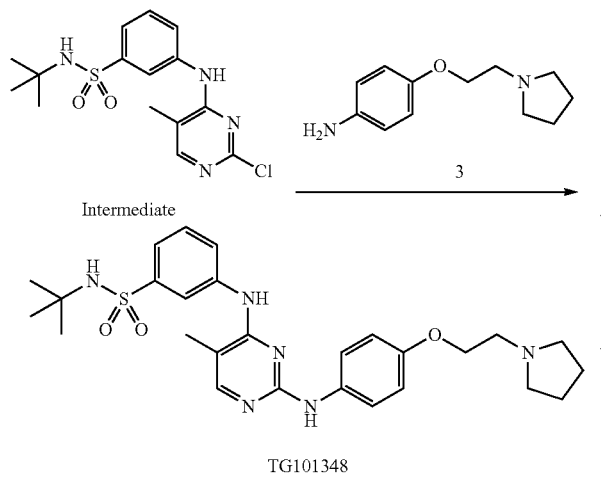

TG101348

Example 4.2(a)

A mixture of N-tert-Butyl-3-(2-chloro-5-methyl-pyrimidin-4-ylamino)-benzenesulfonamide (Intermediate) (0.10 g, 0.28 mmol) and 4-(2-pyrrolidin-1-yl-ethoxy)-phenylamine (3) (0.10 g, 0.49 mmol) in acetic acid (3 mL) was sealed in a microwave reaction tube and irradiated with microwave at 150° C. for 20 min. After cooling to room temperature, the cap was removed and the mixture concentrated. The residue was purified by HPLC and the corrected fractions combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the resulting solid dissolved in minimum amount of EtOAc and hexanes added until solid precipitated. After filtration, the title compound was obtained as a white solid (40 mg, 27%). $^1$H NMR (500 MHz, DMSO-d$^6$): δ 1.12 (s, 9H), 1.65-1.70 (m, 4H), 2.12 (s, 3H), 2.45-2.55 (m, 4H), 2.76 (t, J=5.8 Hz, 2H), 3.99 (t, J=6.0 Hz, 2H), 6.79 (d, J=9.0 Hz, 2H), 7.46-7.53 (m, 4H), 7.56 (s, 1H), 7.90 (s, 1H), 8.10-8.15 (m, 2H), 8.53 (s, 1H), 8.77 (s, 1H). MS (ES+): m/z 525 (M+H)$^+$.

Example 4.2(b)

N-tert-Butyl-3-[(5-methyl-2-{[4-(2-pyrrolidin-1-ylethoxy)phenyl]amino}pyrimidin-4-yl)amino]benzenesulfonamide dihydrochloride monohydrate was prepared from 4-[2-(1-pyrrolidinyl)ethoxy]aniline dihydrochloride (SM3) and Intermediate following steps (A) and (B).

Step (A), preparation of free base of SM3 (3) from SM3, comprised steps (1)-(9): (1) Solubilize NaOH (0.42 UOb) in H2O (9 UOb); (2) Cool <20° C., N2; (3) Add TBME (6 UOb) then SM3 (Malladi Drugs) (1.06 UOb); (4) Mix>20 nm then stop; (5) Drain Aq Ph then extract by TBME (3 UOb); (6) Combine Or Ph; (7) Concentrate, vacuum, T<40° C., to an Oil; (8) Solubilize in IPA (2.5 UOb); and (9) Calculate dry extract 23%.

Step (B) comprised the steps (1)-(6): (1) Mix IPA (10.5 UOb) and Intermediate (UOb); (2) Add free base of SM3 (0.75 UOb, 1.33 eq/interm); (3) add HCl conc (0.413 UOb); (4) Heat 70° C., 20 h, N$_2$, IPC CPL Interm<2%; (5) Cool<20° C.; (2) Centrifuge, N$_2$; (3) Wash IPA (3 UOb); (4) Dry 50° C., vacuum, 26 h; (5) De-lump in Fitzmill; and (6) polybag (×2)/poly drum. Obtained TG101348 dihydrochloride monohydrate, mass 83.8 kg; Yield 98%; OP: 99.5%.

Example 5 Capsule Form of TG101348 and Process of Making TG101348

TG101348 drug products were provided as 10 mg, 40 mg, and 200 mg capsule strengths, where weights are specified for the amount of active (i.e., free base) moiety of TG101348. The quantitative composition of each strength of TG101348 drug product capsule is shown in Table 14.

TABLE 14

List of all components and unit formula for 10 mg, 40 mg, and 200 mg strengths of TG101348 drug product capsules

| Component and Quality Standard (and Grade, if Applicable) | Function | TG101348 10 mg Capsule | TG101348 40 mg Capsule | TG101348 200 mg Capsule |
|---|---|---|---|---|
| TG101348 (drug substance)* | Active ingredient | 11.73 mg | 46.90 mg | 234.80 mg |
| Silicified Microcrystalline Cellulose (Prosolv SMCC 90HD ®)† | Filler/Diluent | 121.92 mg | 448.10 mg | 356.70 mg |
| Sodium Stearyl Fumarate (Pruv ®) | Lubricant | 1.35 mg | 5.00 mg | 6.00 mg |
| Total Capsule Fill Weight | NA | 135.00 mg | 500.00 mg | 597.50 mg |
| Hard Gelatin Capsule | Container | 1 capsule (white opaque, size | 1 capsule (white opaque, size | 1 capsule (Swedish orange, |

TABLE 14-continued

List of all components and unit formula for 10 mg, 40 mg, and 200 mg strengths of TG101348 drug product capsules

| Component and Quality | | Unit Formula | | |
|---|---|---|---|---|
| Standard (and Grade, if Applicable) | Function | TG101348 10 mg Capsule | TG101348 40 mg Capsule | TG101348 200 mg Capsule |
| | | 3, each capsule is 48 ± 3 mg) | 00, each capsule is 118 ± 7 mg) | opaque, size 00, each capsule is 118 ± 7 mg) |

*Adjusted to obtain full potency based on the purity of the TG101348 drug substance lot used.
†Adjusted to accommodate all component weights so as to ensure the total capsule fill weight is constant.
USP = United States Pharmacopoeia; NF = National Formulary; EP = European Pharmacopoeia; JP = Japanese Pharmacopoeia; NA = not applicable.

The components that were used in the manufacturing process for each capsule strength, on a per batch basis, are shown in Table 15.

TABLE 15

List of all components for manufacturing of the dosage forms

| | Strength (Label Claim) | | |
|---|---|---|---|
| | TG101348 10 mg Capsule | TG101348 40 mg Capsule | TG101348 200 mg Capsule |
| Batch Size | 1,620.000 g | 6,000.000 g | 5,975.000 g |
| Component and Quality Standard (and Grade, if Applicable) | Quantity per Batch (g) | Quantity per Batch (g) | Quantity per Batch (g) |
| INTRAGRANULAR COMPONENTS | | | |
| TG101348* | 140.780 | 562.800 | 2,348.175 |
| Silicified Microcrystalline Cellulose (Prosolv SMCC 90HD)† | 214.160 | 856.800 | 3,567.075 |
| Sodium Stearyl Fumarate (Pruv) | 3.560 | 14.400 | 59.750 |
| EXTRAGRANULAR COMPONENTS | | | |
| Silicified Microcrystalline Cellulose (Prosolv SMCC 90HD) | 1248.860 | 4,520.400 | Not included |
| Sodium Stearyl Fumarate (Pruv) | 12.640 | 45.600 | Not included |
| TOTAL OF INTRAGRANULAR COMPONENTS + EXTRAGRANULAR COMPONENTS | | | |
| Total Batch Weight | 1,620.000 g | 6,000.000 g | 5,975.000 g |
| CAPSULE SHELLS | | | |
| Capsule Shell Type | Hard gelatin | Hard gelatin | Hard gelatin |
| Capsule Size | Size 3 | Size 00 | Size 00 |
| Capsule Color | White, opaque | White, opaque | Swedish orange, opaque |
| Total Batch Scale (Capsules) | 12,000 | 12,000 | 10,000 |

*Adjusted to obtain full potency based on the purity of the TG101348 drug substance lot used.
†Adjusted to accommodate all component weights so as to ensure the total batch weight is constant.

The process for making TG101348 capsules is described below:

A. Dry granulation of intragranular components (implemented for all three drug product strengths): 1. TG101348 and intragranular sodium stearyl fumarate were blended within a V-blender for 5 minutes. 2. The blend was passed through a conical mill equipped with a round 18-mesh screen and round impeller. The blend was recharged into the V-blender. 3. Intragranular silicified microcrystalline cellulose was sifted through a 20-mesh screen and added to the blender. The mixture was blended for 15 minutes. 4. The blend was passed through a roller compactor. 5. The roller compacted ribbons were passed through a conical mill equipped with a round 16-mesh screen and round impeller. 6. The milled material was blended within the V-blender for 5 minutes. 7. In-process check (IPC) samples were withdrawn from the V-blender using a sample thief. Samples were subjected to potency analysis.

B. Addition of extragranular components (implemented for 10 mg and 40 mg capsules): 1. Where potency of granules (from Step 7 in A) was outside 98-102% (w/w) nominal, extragranular silicified microcrystalline cellulose was adjusted accordingly. 2. The V-blender was charged with TG101348 di-HCl monohydrate/silicified microcrystalline cellulose/sodium stearyl fumarate granules (from A). 3. The extragranular silicified microcrystalline cellulose was sifted through a 20-mesh screen and added to the V-blender. 4. The Extragranular sodium stearyl fumarate was added to the V-blender. 5. The intragranular and extragranular components were blended for 15 minutes. 6. IPC samples were withdrawn from the V-blender using a sample thief and analyzed for potency.

C. Capsule-filling (implemented for all three drug product strengths): 1. If potency (from Step 7 in A for the 200 mg capsules, or Step 6 in B for the 10 mg and 40 mg capsules)

was outside 98-102% (w/w) nominal, the capsule fill weight was adjusted accordingly. 2. The prepared material was encapsulated using automatic capsule filling machine. The prepared capsules were bottled and stores at 20-28° F. (68-82° C.) and ambient humidity.

Content uniformity and dissolution were examined. HPLC method validation was performed using a one-analyst, one-run-per-analyst design, and satisfied all required criteria for specificity, sensitivity, precision, accuracy, linearity, and sample stability. Specificity was evaluated and confirmed by comparing peak resolution between TG101348 and all of its related compounds, intermediates, and degradants (established from forced degradation studies). The limit of quantitation and limit of detection was established at 0.10 µg/mL and 0.03 µg/mL TG101348, respectively. Precision for content uniformity was evaluated via six injections of the mg and 200 mg strength capsules, prepared at the target assay concentration. RSD results were 3.7% and 5.8% for the 10 mg and 200 mg strength capsules, respectively. Precision for dissolution was evaluated via six injections at each dissolution timepoint of the 10 mg and 200 mg strength capsules. Relative standard deviation ("RSD") results for all strengths and corresponding time points were well within the acceptance criteria (±10%) specified in the validation protocol. Accuracy (defined by the recovery of the analyte spiked into a placebo solution for the 10 mg and 200 mg strength capsules) was evaluated at 70%, 100%, and 130% of the target assay standard concentration. Recovery values for all measurements were within the acceptance criteria (93%-105%) specified in the validation protocol. Linearity was demonstrated over the range of 50% to 120% of the target assay standard concentration, and exhibited an r2 of 1.00. Sample stability and method robustness were also demonstrated during method validation.

Example 6 Formulation Study for TG101348

The formulation study for N-tert-Butyl-3-[(5-methyl-2-{[4-(2-pyrrolidin-1-ylethoxy)phenyl]amino}pyrimidin-4-yl)amino]benzenesulfonamide di-HCl monohydrate salt was conducted.

N-tert-Butyl-3-[(5-methyl-2-{[4-(2-pyrrolidin-1-ylethoxy)phenyl]amino}pyrimidin-4-yl)amino]benzenesulfonamide di-HCl Monohydrate Salt Compatibility with Capsule Shells It was unknown whether the caustic/acidic nature of N-tert-Rutyl-3-[(5-methyl-2-{[4-(2-pyrrolidin-1-ylethoxy)phenyl]amino}pyrimidin-4-yl)amino]benzenesulfonamide di-HCl monohydrate salt (TG101348 di-HCl monohydrate) would be incompatible with capsules due to the potential caustic/acidic nature of a di-HCl salt.

Hard gelatin and hydroxypropylmethyl cellulose (HPMC) capsule shells (size #00250) were filled with 250 mg of TG101348 di-HCl monohydrate. The filled capsules were placed on accelerated stability (40° C./75% relative humidity (RH) and 25° C./60% RH). The capsules were packaged into 30 mL (1 oz) amber high density polyethylene (HDPE) bottles. A summary of the formulations and accelerated stability protocol for the stability study is shown in Table 16.

TABLE 16

| Formulations | (i) Size #00 Hard Gelatin (White Opaque) Capsule Filled with 250 mg [1] (ii) Size #00 Hard HPMC (White Opaque) Capsule Filled with 250 mg [1] |
|---|---|
| Lot Numbers | 191-031A: Gelatin capsule fills stored at 25° C./60% RH 191-031B: Gelatin capsule fills stored at 40° C./75% RH 191-031C: HPMC capsule fills stored at 25° C./60% RH 191-031D: HPMC capsule fills stored at 40° C./75% RH |

| Storage Condition | Timepoint (weeks) | | | |
|---|---|---|---|---|
| | t = 0 | t = 1 weeks | t = 2 weeks | t = 3 weeks |
| 40° C./75% RH | 1 capsule | 1 capsule | 1 capsule | 1 capsule |
| 25° C./60% RH | | 1 capsule | 1 capsule | 1 capsule |
| Comments | | | | |
| Storage | Nalgene 30 mL (1 oz) Amber Wide Mouth, HDPE Store capsules for each formulation at each condition in the same bottle | | | |
| Appearance/ Assay/ Impurities | 1 capsules per pull | | | |

[1] a free base assay content of 83.78%. 250 mg of TG101348 is equivalent to 209.45 mg of free base.

It was found that TG101348 di-HCL monohydrate was compatible with hard gelatine capsules. No appreciable changes in attributes (appearance, assay, impurities) were observed over the timepoints of the study (t=1, 2, and 3 weeks).

Drug Substance Blend Compatibility with Fillers and Lubricants

A matrix of formulation blends was designed to study the compatibility of TG101348 di-HCl monohydrate with four fillers and two lubricants (Table 17). Blends were prepared at a scale of 2.5 g each by prescreening all components through a 500 µm sieve, blending all components except the lubricant using a Turbula T2B blender for 10 min at 22 rpm, screening the blend through a 500 µm sieve, blending for 10 min, adding lubricant (weight adjusted) and blending for 5 min. The blends were manufactured and stored in 30 mL amber HDPE bottles under primary (60° C./ambient humidity) and backup conditions (40° C./75% RH, 25° C./60% RH, and 5° C.). A summary of the accelerated stability protocol is shown in Table 18. No appreciable changes in attributes (appearance, assay, impurities) were observed over the course of the study.

TABLE 17

| Ingredients | Formulation (% w/w) | | | | | | | | |
|---|---|---|---|---|---|---|---|---|---|
| | 1 | 2 | 3 | 4 | 5 | 6 | 7 | 8 | Control |
| TG101348 di-HCl monohydrate [1] | 50.46% | 50.46% | 50.46% | 50.46% | 50.46% | 50.46% | 50.46% | 50.46% | 100% |
| Lactose (Fast-Flo) | 48.54% | 48.54% | — | — | — | — | — | — | — |

TABLE 17-continued

| Ingredients | Formulation (% w/w) | | | | | | | | |
|---|---|---|---|---|---|---|---|---|---|
| | 1 | 2 | 3 | 4 | 5 | 6 | 7 | 8 | Control |
| Mannitol (Parteck M200) | — | — | 48.54% | 48.54% | — | — | — | — | — |
| MCC (Avicel PH102) | — | — | — | — | 49.04% | 49.04% | — | — | — |
| MCC (ProSolv 90 HD) | — | — | — | — | — | — | 49.04% | 49.04% | — |
| Magnesium Stearate | 1.0% | — | 1.0% | — | 0.5% | — | 0.5% | — | — |
| Sodium Stearyl Fumarate (Pruv) | — | 1.0% | — | 1.0% | — | 0.5% | — | 0.5% | — |

[1] Based on TG101348 with a free-base assay content of 81.26% (equivalent to 41.00% w/w free base content in the formulation).

TABLE 18

| Storage Condition | Timepoint (weeks) | | | | |
|---|---|---|---|---|---|
| | t = 0 | t = 1 weeks | t = 2 weeks | t = 4 weeks | t = 12 weeks |
| 60° C./ambient humidity | X | X | X | X | X |
| 40° C./75% RH | | ○ | ○ | ○ | ○ |
| 25° C./60% RH | | ○ | ○ | ○ | ○ |
| 5° C. | | ○ | ○ | ○ | ○ |
| Comments | | | | | |
| Storage | Nalgene 30 mL (1 oz) Amber Wide Mouth, HDPE Store blend for each formulation at each condition in the separate bottles | | | | |
| Testing | Visual appearance Assay Impurities | | | | |

○ = optional.

Powder-In-Capsule Development
Excipient Selection

Excipient compatibility testing of dry blends of TG101348 di-HCl monohydrate with four fillers (lactose, mannitol, microcrystalline cellulose (MCC) Avicel PH102, and MCC ProSolv 90 HD) and two lubricants (magnesium stearate and sodium stearyl fumarate (Pruv) (Table 17) indicated no incompatibilities. Prosolv SMCC 90HD (i.e., silicified microcrystalline cellulose) and Lactose Fast-Flo (i.e., spray dried lactose monohydrate) were selected as fillers for further testing based on properties amenable to direct dry blending processes. Magnesium stearate (vegetable grade) and Pruv were selected as lubricants for further testing. All excipients are global regulatory approved for use in solid oral dosage forms (USA, European Union, Japan).

Suitability for Dry Powder Process Development

True densities of TG101348 di-HCl monohydrate having particles of rounded/granular appearance, silicified microcrystalline cellulose (Prosolv SMCC 90HD), and sodium stearyl fumarate (Pruv) were measured using a helium pycnometer (Micromeritics Accupyc 1340). The true density of the drug substance and excipients (fillers/diluents) appeared well matched.

Capsule Formulations

A "matrix" of prototype capsule formulations for stability evaluation was designed, and is summarized in Table 19. Two dosage strengths were selected, 10 and 125 mg.

TABLE 19

| Component | Prototype Formulation | | | | | | | |
|---|---|---|---|---|---|---|---|---|
| | P1 | P2 | P3 | P4 | P5 | P6 | P7 | P8 |
| | % w/w composition | | | | | | | |
| Dry Blend | | | | | | | | |
| TG101348 di-HCl monohydrate [1] | 49.37 | 49.37 | 49.37 | 49.37 | 49.37 | 49.37 | 49.37 | 49.37 |
| Prosolv SMCC 90HD | 50.13 | 50.13 | 50.13 | 50.13 | — | — | — | — |
| Lactose Fast-Flo | — | — | — | — | 49.63 | 49.63 | 49.63 | 49.63 |
| Magnesium Stearate | 0.5 | 0.5 | 0.5 | 0.5 | 1.0 | 1.0 | 1.0 | 1.0 |
| Total | 100% | 100% | 100% | 100% | 100% | 100% | 100% | 100% |
| Capsule Fill | | | | | | | | |
| Capsule Type | Gelatin Size #00 | Gelatin Size #00 | HPMC Size #00 | HPMC Size #00 | Gelatin Size #00 | Gelatin Size #00 | HPMC Size #00 | HPMC Size #00 |

TABLE 19-continued

| | Prototype Formulation | | | | | | | |
|---|---|---|---|---|---|---|---|---|
| | P1 | P2 | P3 | P4 | P5 | P6 | P7 | P8 |
| Component | % w/w composition | | | | | | | |
| Capsule Color | White Opaque | White Opaque | White Opaque | White Opaque | White Opaque | White Opaque | White Opaque | White Opaque |
| Capsule Fill | 24.39 mg blend fill | 304.86 mg blend fill | 24.39 mg blend fill | 304.86 mg blend fill Dose | 24.39 mg blend fill | 304.86 mg blend fill | 24.39 mg blend fill | 304.86 mg blend fill |
| Dose (mg, i.e., free base) | 10 mg | 125 mg | 10 mg | 125 mg | 10 mg | 125 mg | 10 mg | 125 mg |

(1) Based on a free-base assay content of 83.05% (equivalent to 41.00% w/w free base content in the formulation).

Accelerated Stability Testing Protocol

Table 20 summarizes the accelerated stability protocol applied for the capsule prototypes. No appreciable changes in attributes (appearance, assay, impurities, in vitro dissolution) were observed over the timepoints of the study (t=1, 2, 4, and 8 weeks at 40° C./75% RH and 25° C./60% RH). Based on these results, Prototypes P2 and P6 were selected for further evaluation.

TABLE 20

| | Timepoint (weeks) | | | | |
|---|---|---|---|---|---|
| Storage Condition | t = 0 | 2 weeks | 4 weeks | 8 weeks | Contingency |
| 40° C./75% RH | 16 capsules | 5 capsules | 5 capsules | 5 capsules | 7 capsules |
| 25° C./60% RH | | 5 capsules | 5 capsules | 5 capsules | 7 capsules |
| | Comments | | | | |
| Storage | Store each pull separately into individual bottles Nalgene 30 mL (1 oz) Amber Wide Mouth, HDPE | | | | |
| Appearance/ Assay/Impurities | 2 capsules per pull | | | | |
| In vitro Dissolution | 3 capsules per pull | | | | |
| Notes | 16 capsules for t = 0 to include support for in vitro dissolution methodology development | | | | |

In Vitro Dissolution Performance Considerations

On in vitro dissolution testing, prototype formulations filled into gelatin capsule shells (P1, P2, P5, P6) demonstrated ≥85% drug release within 15 minutes. Prototypes formulations filled into HPMC capsule shells (e.g., P3, P4, P7, P8) typically demonstrated <60% drug release after 60 minutes. Prototypes in HPMC capsules were therefore not progressed beyond t=0 testing.

Absorption Enhancer Capsule Development

TG101348 is on the borderline between "low" and "high" permeability based on caco-2 permeability data. In addition, bioavailability in multiple species was typically 20-25%. Therefore, it was not known whether an "absorption enhancer" would be required in the formulation to achieve adequate bioavailability.

Excipient Selection

Based on excipient compatibility described above, silicified microcrystalline cellulose (Prosolv SMCC 90IID) was used as the primary filler/carrier excipient for the absorption enhancement formulation. Four absorption enhancement excipient candidates were selected for further testing (Table 21).

TABLE 21

| Absorption Enhancement Excipient | Excipient Manufacturer | Absorption Enhancement Mechanism |
|---|---|---|
| Vitamin E D-α-tocopheryl polyethylene glycol succinate (Vitamin E TPGS) | Eastman Chemical Company | Lipid excipient (surfactant), P-glycoprotein (PGP) inhibitor |
| Gelucire 44/14 (PEG-32 glyceryl laurate) | Gattefossé S.A. | Lipid excipient (amphiphile) |
| Pluronic F127 | BASF Chemical Company | Polymeric amphiphilic surfactant/ micellar solubilization/ P-glycoprotein (PGP) inhibitor |
| Glyceryl monostearate 40-55 | Gattefossé S.A. | Lipid excipient (emulsifier) P-glycoprotein (PGP) inhibitor |

Formulations and Manufacturing Processes

Table 22 summarizes the absorption enhancement formulations tested. Melt granulation, as opposed to a direct blend manufacturing process, was selected to produce the formulation.

TABLE 22

Absorption Enhancer Formulations

| Component | A | B | C | D |
|---|---|---|---|---|
| | % w/w composition | | | |
| Granules | | | | |
| TG101348 di-HCl monohydrate [1] | 50.17% | 50.17% | 50.17% | 50.17% |
| Vitamin E TPGS | 25.00% | — | — | — |
| Gelucire 44/14 | — | 25.00% | — | — |
| Pluronic F127 | — | — | 3.33% | — |
| Glyceryl monostearate | — | — | — | 3.33% |
| ProSolv SMCC 90HD | 24.33% | 24.33% | 46.00% | 46.00% |
| Magnesium Stearate | 0.50% | 0.50% | 0.50% | 0.50% |
| Capsule Fill | | | | |
| Capsule Type | Gelatin Size #00 | Gelatin Size #00 | Gelatin Size #00 | Gelatin Size #00 |
| Capsule Color | White Opaque | White Opaque | White Opaque | White Opaque |
| Capsule Fill | 300 mg of granules | 300 mg of granules | 300 mg of granules | 300 mg of granules |
| Dose | | | | |
| Dose (mg, i.e. free base) | 125 mg | 125 mg | 125 mg | 125 mg |

[1] Based on TG101348 with a free-base assay content of 83.05% (equivalent to 41.67% w/w free base content in the formulation).

Crossover Beagle Dog PK Study

A crossover beagle dog PK study was performed testing five formulations: an oral solution as described below, two capsule formulations without absorption enhancer and two capsule formulations with absorption enhancer.

Five beagle dogs were dosed with each formulation at a TG101348 dose of 125 mg, or approximately 11 mg/kg based on mean body weights, with a 'washout' of one week in between doses. The formulations administered are summarized in Table 23.

TABLE 23

| Phase | Dose | Formulation | Dose Strength | Dose Amount | Matrix Collected |
|---|---|---|---|---|---|
| 1 | Oral solution | Aqueous, 0.5% MC, 6.25 mg/mL | 125 mg | 20 mL | Plasma |
| 2 | Prototype Capsule P2 | Capsule fill containing dry blend of: 49.37% TG101348 Lot K-18 50.13% Prosolv SMCC 90HD 0.5% Magnesium Stearate | 125 mg | One capsule | Plasma |
| 3 | Prototype Capsule P6 | Capsule fill containing dry blend of: 49.37% TG101348 Lot K-18 49.63% Lactose Fast-Flo 1.0% Magnesium Stearate | 125 mg | One capsule | Plasma |
| 4 | Prototype Capsule A | Capsule fill containing granules composed of: 50.17% TG101348 Lot K-18 3.33% Glyceryl Monostearate 46.00% Prosolv SMCC 90HD 0.5% Magnesium Stearate | 125 mg | One capsule | Plasma |
| 5 | Prototype Capsule D | Capsule fill containing granules composed of: 50.17% TG101348 Lot K-18 25.00% Vitamin E TPGS 24.33% Prosolv SMCC 90HD 0.5% Magnesium Stearate | 125 mg | One capsule | Plasma |

All four capsule formulations displayed immediate release characteristics with a demonstration of bioequivalence to the reference solution dose. Therefore, despite the boarderline permeability in human caco-2 cells and the 20-25% bioavailability in various animal species, capsule formulations without an absorption enhancer formulation demonstrated immediate release characteristics.

Process Development

Drug Substance Particle Morphology

Different particle morphology, from rounded, granular particles (mean particle size≈25 μm), to that of small needles (mean particle size=7-10 μm) was found between different lots of the drug substance. The needle form was found to be highly static, which could negatively affect drug product manufacturing and also negatively affect drug product content uniformity.

Dry Granulation Process

The initial formulation, developed with the drug substance having rounded, granular particles with a mean particle size of 25 μm was 50:50 ratio by weight of TG101348 drug substance and filler, with 0.5% w/w lubricant. Prior to roller compaction, a blend of drug, filler, and lubricant was prepared. As described herein, the drug substance was passed through a co-mil to de-agglomerate prior to blending with formulation excipients. The drug substance having small needles demonstrated a high tendency to agglomerate on storage. After deagglomerating the drug substance having small needles, significant reagglomeration or 'clumping' would occur almost instantaneously. This reagglomeration was significantly reduced through blending the drug with lubricant prior to milling.

The initial formulation of TG101348 di-HCL monohydrate comprised about a 50:50 ratio by weight of TG101348 drug substance and filler, with 0.5% w/w lubricant. This formulation exhibited a poor flow and significant sticking to the metal rolls within the roller compactor.

The amount of magnesium stearate lubricant could be increased in the formulation, however increasing the concentration within the formulation could adversely affect drug release kinetics. The lubricant sodium laurel fumarate was also shown to be compatible with TG101348 di-HCl monodyrate and is less hygroscopic than magnesium stearate and was added (at a weight ratio of 2.0% w/w) instead of magnesium stearate which minimized sticking of the formulation to the metal rolls of the roller compactor. However, powder flow remained poor.

The ratio of TG101348 drug substance to filler was reduced from about 50:50 to about 40:60. The lubricant (Pmruv) content was also reduced to 1% w/w which provided acceptable flow and minimal sticking within the roller compactor.

Development of Multi-Dose Formulations

On capsule hand-filling trials, with aggressive tamping, into size #00 gelatin capsule shells, approximately 600 mg of granules appeared to be the maximum achievable fill. With a drug substance loading of 40% w/w in the formulation, and with the TG101348 di-HCL monohydrate batch comprising 83.78% free base content, it therefore appeared that an upper capsule strength of 200 mg strength was feasible.

The dry granulation process developed as described herein to produce a particles having intragranular TG101348 di-HCL monohydrate and sodium laurel fumarate allowed the preparation of a range of capsule dosages using dry blending processes.

The mean granule size was approximately 300 μm and the silicified microcrystalline cellulose mean particle size was approximately 100 μm. Therefore, 40 mg and 10 mg capsule strength formulations were produced through dilution of the granules with extragranular silicified microcrystalline cellulose. The general, particles sizes within a The size of the granules and the extragranular silicified microcrystalline cellulose are similar enough to allow homogeneous mixing.

40 mg strength capsules were produced using a formulation comprising comparable fill volume to the 200 mg formulation, within the same capsule shell (size #00 hard gelatin capsule). For the 10 mg strength capsules, a common blend with the 40 mg capsule strength formulation was used by filing a smaller capsule size.

Oral Solution Formulation

An oral solution formulation was developed that contained the drug substance, 0.5% methylcellulose (MC) and 0.05% Tween 80. A pH-stability study was conducted at 60° C. on formulations passed through a 0.22 μm polyethersulfone (PES) filter. No appreciable changes in attributes (appearance, assay, impurities) were observed over the course of the study (14 days). A second oral solution formulation was developed that contained the drug substance and 0.5% MC. The second oral solution formulation was used in the dog PK study.

Although the foregoing examples have been described in some detail by way of illustration and example for purposes of clarity of understanding, the descriptions and examples should not be construed as limiting the scope of the invention.

What is claimed is:

1. A capsule comprising a formulation comprising (i) a compound that is N-tert-butyl-3-[(5-methyl-2-{[4-(2-pyrrolidin-1-ylethoxy)phenyl]amino}pyrimidin-4-yl)amino]benzenesulfonamide dihydrochloride monohydrate, (ii) a microcrystalline cellulose, and (iii) sodium stearyl fumarate, wherein:
   the weight ratio of N-tert-butyl-3-[(5-methyl-2-{[4-(2-pyrrolidin-1-ylethoxy)phenyl]amino}pyrimidin-4-yl)amino]benzenesulfonamide to microcrystalline cellulose in the formulation is about 1:1.5 to about 1:9, and
   sodium stearyl fumarate is about 1% by weight of the formulation.

2. The capsule unit of claim 1, wherein the microcrystalline cellulose is silicified microcrystalline cellulose.

3. The capsule of claim 1, wherein the to formulation comprises about 117 mg of N-tert-butyl-3-[(5-methyl-2-{[4-(2-pyrrolidin-1-ylethoxy)phenyl]amino}pyrimidin-4-yl)amino]benzenesulfonamide dihydrochloride monohydrate.

4. The capsule of claim 1, wherein the formulation comprises about 235 mg of N-tert-butyl-3-[(5-methyl-2-{[4-(2-pyrrolidin-1-ylethoxy)phenyl]amino}pyrimidin-4-yl)amino]benzenesulfonamide dihydrochloride monohydrate, about 357 mg of silicified microcrystalline cellulose, and about 6 mg of sodium stearyl fumarate.

5. The capsule of claim 1, wherein the capsule is a hard gelatin capsule.

6. A method of treating myelofibrosis in a subject comprising administering a capsule comprising a formulation comprising (i) a compound that is N-tert-butyl-3-[(5-methyl-2-{[4(2-pyrrolidin-1-ylethoxy)phenyl]amino}pyrimidin-4-yl)amino]benzenesulfonamide dihydrochloride monohydrate, (ii) a microcrystalline cellulose, and (iii) sodium stearyl fumarate, wherein:
   the weight ratio of N-tert-butyl-3-[(5-methyl-2-{[4-(2-pyrrolidin-1-ylethoxy)phenyl]amino}pyrimidin-4-yl)amino]benzenesulfonamide to microcrystalline cellulose in the formulation is about 1:1.5 to about 1:9, and
   sodium stearyl fumarate is about 1% by weight of the formulation.

7. A method of preparing a capsule comprising a formulation, wherein the method comprises blending a microcrystalline cellulose and sodium stearyl fumarate with a compound that is N-tert-butyl-3-[(5-methyl-2-{[4-(2-pyrrolidin-1-ylethoxy)phenyl]amino}pyrimidin-4-yl)amino]benzenesulfonamide dihydrochloride monohydrate, wherein:
   the weight ratio of N-tert-butyl-3-[(5-methyl-2-{[4-(2-pyrrolidin-1-ylethoxy)phenyl]amino}pyrimidin-4-yl)amino]benzenesulfonamide to microcrystalline cellulose in the formulation is about 1:1.5 to about 1:9, and
   sodium stearyl fumarate is about 1% by weight of the formulation.

8. An article of manufacture comprising:
(a) a capsule comprising a formulation comprising (i) a compound that is N-tert-butyl-3-[(5-methyl-2-{[4-(2-pyrrolidin-1-ylethoxy)phenyl]amino}pyrimidin-4-yl)amino]benzenesulfonamide dihydrochloride monohydrate, (ii) a microcrystalline cellulose, and (iii) sodium stearyl fumarate,
wherein:
the weight ratio of N-tert-butyl-3-[(5-methyl-2-{[4-(2-pyrrolidin-1-ylethoxy)phenyl] amino}pyrimidin-4-yl)amino]benzenesulfonamide to microcrystalline cellulose in the formulation is about 1:1.5 to about 1:9, and
sodium stearyl fumarate is about 1% by weight of the formulation; and
(b) a package insert or a label indicating that the formulation is useful for treating myelofibrosis in a subject.

9. The capsule or claim 3, wherein the microcrystalline cellulose is silicified microcrystalline cellulose.

10. The article of manufacture of claim 8, wherein the microcrystalline cellulose is silicified microcrystalline cellulose.

11. The method of claim 7, wherein the microcrystalline cellulose is silicified microcrystalline cellulose.

12. The capsule of claim 1, wherein the weight ratio or N-tert-butyl-3-[(5-methyl-2-{[4-(2-pyrrolidin-1-ylethoxy)phenyl]amino}pyrimidin-4-yl)amino]benzenesulfonamide to microcrystalline cellulose in the formulation is about 1:1.5 to about 1:2.

13. The capsule of claim 12, wherein the formulation comprises about 117 mg of N-tert-butyl-3-[(5-methyl-2-{[4-(2-pyrrolidin-1-ylethoxy)phenyl]amino}pyrimidin-4-yl)amino]benzenesulfonamide dihydrochloride monohydrate.

14. The capsule of claim 12, wherein the formulation comprises about 235 mg of N-tert-butyl-3-[(5-methyl-2-{[4-(2-pyrrolidin-1-ylethoxy)phenyl]amino}pyrimidin-4-yl)amino]benzenesulfonamide dihydrochloride monohydrate.

15. The capsule of claim 12, wherein the microcrystalline cellulose is silicified microcrystalline cellulose.

16. The capsule of claim 15, wherein the formulation comprises about 117 mg of N-tert-butyl-3-[(5-methyl-2-{[4-(2-pyrrolidin-1-ylethoxy)phenyl]amino}pyrimidin-4-yl)amino]benzenesulfonamide dihydrochloride monohydrate.

17. The capsule of claim 15, wherein the formulation comprises about 235 mg of N-tert-butyl-3-[(5-methyl-2-{[4-(2-pyrrolidin-1-ylethoxy)phenyl]amino}pyrimidin-4-yl)amino]benzenesulfonamide dihydrochloride monohydrate.

18. The capsule of claim 4, wherein the microcrystalline cellulose is silicified microcrystalline cellulose.

19. The article of manufacture of claim 8, wherein the formulation comprises about 117 mg of N-tert-butyl-3-[(5-methyl-2-{[4-(2-pyrrolidin-1-ylethoxy)phenyl]amino}pyrimidin-4-yl)amino]benzenesulfonamide dihydrochloride monohydrate.

20. The article of manufacture of claim 19, wherein the microcrystalline cellulose is silicified microcrystalline cellulose.

21. The article of manufacture of claim 8, wherein the weight ratio of N-tert-butyl-3-[(5-methyl-2-{[4-(2-pyrrolidin-1-ylethoxy)phenyl]amino}pyrimidin-4-yl)amino]benzenesulfonamide to microcrystalline cellulose in the formulation is about 1:1.5 to about 1:2.

22. The article of manufacture of claim 21, wherein the microcrystalline cellulose is silicified microcrystalline cellulose.

23. The article or manufacture of claim 22, wherein the formulation comprises about 117 mg of N-tert-butyl-3-[(5-methyl-2-{[4-(2-pyrrolidin-1-ylethoxy)phenyl]amino)}pyrimidin-4-yl)amino]benzenesulfonamide dihydrochloride monohydrate.

24. The article of manufacture of claim 8, wherein the formulation comprises about 235 mg of N-tert-butyl-3-[(5-methyl-2-{[4-(2-pyrrolidin-1-ylethoxy)phenyl]amino}pyrimidin-4-yl)amino]benzenesulfonamide dihydrochloride monohydrate.

25. The article of manufacture of claim 22, wherein the formulation comprises about 235 mg of N-tert-butyl-3-[(5-methyl-2-{[4-(2-pyrrolidin-1-ylethoxy)phenyl]amino}pyrimidin-4-yl)amino]benzenesulfonamide dihydrochloride monohydrate.

26. The article of manufacture of claim 24, wherein the microcrystalline cellulose is silicified microcrystalline cellulose.

* * * * *

UNITED STATES PATENT AND TRADEMARK OFFICE
CERTIFICATE OF CORRECTION

| | | |
|---|---|---|
| PATENT NO. | : 10,391,094 B2 | Page 1 of 4 |
| APPLICATION NO. | : 13/888096 | |
| DATED | : August 27, 2019 | |
| INVENTOR(S) | : Arvind Jayan et al. | |

It is certified that error appears in the above-identified patent and that said Letters Patent is hereby corrected as shown below:

In the Specification

Column 2, Lines 35-37: Please replace "N-tert-butyl-3-[(5-methyl-2-{[4-(2-pyrrolidin-1-ylethoxy)phenyl]amino} pyrimidin-4-yl)amino]benzenesulfonamide" with --*N-tert*-butyl-3-[(5-methyl-2-{[4-(2-pyrrolidin-1-ylethoxy)phenyl]amino}pyrimidin-4-yl)amino]benzenesulfonamide--.

Column 3, Lines 33-35: Please replace "N-tert-butyl-3-[(5-methyl-2-{([4-(2-pyrrolidin-1-ylethoxy)phenyl]amino}pyrimidin-4-yl)amino]benzenesulfonamide" with --*N-tert*-butyl-3-[(5-methyl-2-{[4-(2-pyrrolidin-1-ylethoxy)phenyl]amino}pyrimidin-4-yl)amino]benzenesulfonamide--.

Column 8, Lines 1-3: Please replace "N-tert-butyl-3-[(5-methyl-2-{[4-(2-pyrrolidin-1-ylethoxy)phenyl]ami- no}pyrimidin-4-yl)amino]benzenesulfonamide" with --*N-tert*-butyl-3-[(5-methyl-2-{[4-(2-pyrrolidin-1-ylethoxy)phenyl]amino}pyrimidin-4-yl)amino]benzenesulfonamide--.

Column 8, Lines 6-8: Please replace "N-tert-butyl-3-[(5-methyl-2-{[4-(2-pyrrolidin-1-ylethoxy)phenyl]amino} pyrimidin-4-yl)amino]benzenesulfonamide" with --*N-tert*-butyl-3-[(5-methyl-2-{[4-(2-pyrrolidin-1-ylethoxy)phenyl]amino}pyrimidin-4-yl)amino]benzenesulfonamide--.

Column 10, Line 30: Please replace "6≥50%" with --6 ≥50%--.

Column 10, Line 39: Please replace "count>450×$10^9$/L" with --count > 450 × $10^9$/L--.

Column 10, Line 60: Please replace "baseline>20%" with --baseline > 20%--.

Column 11, Line 35: Please replace "(score=11-3)" with --(score=1-3)--.

Column 11, Line 61: Please replace "count>11×$10^9$/L" with --count >11 × $10^9$/L--.

Column 12, Line 1: Please replace "burden>20%" with --burden >20%--.

Signed and Sealed this
Fifth Day of May, 2020

Andrei Iancu
*Director of the United States Patent and Trademark Office*

CERTIFICATE OF CORRECTION (continued)
U.S. Pat. No. 10,391,094 B2

Column 12, Line 11: Please replace "burden>20%" with --burden >20%--.

Column 12, Line 14: Please replace "p=0.00$^2$" with --p=0.002--.

Column 13, Line 67 to Column 14, Line 1: Please replace "N-tert-butyl-3-[(5-methyl-2-{[4-(2-pyrrolidin-1-ylethoxy)phenyl]amino} - pyrimidin-4-yl)amino]benzenesulfonamide" with --*N-tert*-butyl-3-[(5-methyl-2-{[4-(2-pyrrolidin-1-ylethoxy)phenyl]amino}pyrimidin-4-yl)amino]benzenesulfonamide--.

Column 14, Lines 4-6: Please replace "N-tert-butyl-3-[(5-methyl-2-{[4-(2-pyrrolidin-1-ylethoxyphenyl]amino}pyrimidin-4-yl)amino]benzenesulfonamide" with --*N-tert*-butyl-3-[(5-methyl-2-{[4-(2-pyrrolidin-1-ylethoxy)phenyl]amino}pyrimidin-4-yl)amino]benzenesulfonamide--.

Column 14, Line 52: Please replace "aft" with --art--.

Column 16, Lines 43-45: Please replace "N-tert-butyl-3-[(5-methyl-2-([4-(2-pyrrolidin-1-ylethoxy)phenyl]amino pyrimidin-4-yl)amino]benzenesulfonamide" with --*N-tert*-butyl-3-[(5-methyl-2-{[4-(2-pyrrolidin-1-ylethoxy)phenyl]amino}pyrimidin-4-yl)amino]benzenesulfonamide--.

Column 17, Lines 8-10: Please replace "N-tert-butyl-3-[(5-methyl-2-[4-(2-pyrrolidin-1-ylethoxy)phenyl]amino pyrimidin-4-yl)amino]benzenesulfonamide" with --*N-tert*-butyl-3-[(5-methyl-2-{[4-(2-pyrrolidin-1-ylethoxy)phenyl]amino}pyrimidin-4-yl)amino]benzenesulfonamide--.

Column 18, Line 67 to Column 19, Line 1: Please replace "N-tert-butyl-3-[(5-methyl-2-{([4-(2-pyrrolidin-1-ylethoxy)phenyl]amino}pyrimidin-4-yl)amino]benzenesulfonamide" with --*N-tert*-butyl-3-[(5-methyl-2-{[4-(2-pyrrolidin-1-ylethoxy)phenyl]amino}pyrimidin-4-yl)amino]benzenesulfonamide--.

Column 20, Lines 10-12: Please replace "N-tert-butyl-3-[(5-methyl-2-{([4-(2-pyrrolidin-1-ylethoxy)phenyl]amino}pyrimidin-4-yl)amino]benzenesulfonamide" with --*N-tert*-butyl-3-[(5-methyl-2-{[4-(2-pyrrolidin-1-ylethoxy)phenyl]amino}pyrimidin-4-yl)amino]benzenesulfonamide--.

Column 22, Line 47: Please replace "phenyloin" with --phenytoin--.

Column 28, Line 59: Please replace "range<1-76" with --range <1-76--.

Column 29, Line 39: Please replace "TG 101348" with --TG101348--.

Column 29, Line 40: Please replace "lcukocyte" with --leukocyte--.

Column 30, Line 55: Please replace "count>450×10$^9$/L" with --count > 450 × 10$^9$/L--.

Column 30, Line 62: Please replace "baseline>20%" with --baseline > 20%--.

Column 30, Line 64: Please replace "baseline>20%" with --baseline > 20%--.

CERTIFICATE OF CORRECTION (continued)
U.S. Pat. No. 10,391,094 B2

Column 32, Line 56: Please replace "218" with --$\geq$18--.

Column 36, Line 66: Please replace "(n-=6)" with --(*n*=6)--.

Column 43, Line 54: Please replace "count>11×10$^9$/L" with --count >11 × 10$^9$/L--.

Column 43, Line 63: Please replace "count>450×10$^9$/L" with --count >450 × 10$^9$/L--.

Column 44, Line 18: Please replace "(p=0.00$^2$)" with --(p=0.002)--.

Column 44, Line 24: Please replace "burden>20%" with --burden >20%--.

Column 44, Line 29: Please replace "$\geq$20%" with -->20%--.

Column 45, Line 43: Please replace "hypercramylasemia" with --hyperamylasemia--.

Column 48, Lines 21-22: Please replace "Mix>20nm" with --Mix >20mn--.

Column 51, Line 17: Please replace "the mg" with --the 10 mg--.

Column 51, Lines 49-50: Please replace "N-tert-Rutyl-3-[(5-methyl-2-{[4-(2-pyrrolidin-1-ylethoxy)phenyl]amino}pyrimidin-4-yl)amino]benzenesulfonamide" with --*N-tert*-Butyl-3-[(5-methyl-2-{[4-(2-pyrrolidin-1-ylethoxy)phenyl]amino}pyrimidin-4-yl)amino]benzenesulfonamide--.

Column 55, Line 48: Please replace "$\geq$85%" with --> 85%--.

Column 58, Line 59: Please replace "=" with --$\approx$--.

Column 59, Line 29: Please replace "Pmruv" with --Pruv--.

In the Claims

Claim 2, Column 60, Line 25: Please delete the term "unit".

Claim 3, Column 60, Line 27: Please delete the term "to".

Claim 6, Column 60, Lines 41-43: Please replace "N-tert-butyl-3-[(5-methyl-2-{[4(2-pyrrolidin-1-ylethoxy)phenyl]amino}pyrimidin-4-yl)amino]benzenesulfonamide" with --*N-tert*-butyl-3-[(5-methyl-2-{[4-(2-pyrrolidin-1-ylethoxy)phenyl]amino}pyrimidin-4-yl)amino]benzenesulfonamide--.

Claim 9, Column 61, Line 17: Please replace "or" with --of--.

Claim 12, Column 61, Line 24: Please replace "or" with --of--.

Claim 23, Column 62, Line 25: Please replace "or" with --of--.

CERTIFICATE OF CORRECTION (continued)
U.S. Pat. No. 10,391,094 B2

Claim 23, Column 62, Lines 26-28: Please replace "N-tert-butyl-3-[(5-methyl-2-{[4-(2-pyrrolidin-1-ylethoxy)phenyl]amino)}pyrimidin-4-yl)amino]benzenesulfonamide" with --*N-tert*-butyl-3-[(5-methyl-2-{[4-(2-pyrrolidin-1-ylethoxy)phenyl]amino}pyrimidin-4-yl)amino]benzenesulfonamide--.